(12) United States Patent
Awni et al.

(10) Patent No.: US 11,484,534 B2
(45) Date of Patent: *Nov. 1, 2022

(54) METHODS FOR TREATING HCV

(71) Applicant: AbbVie Inc., North Chicago, IL (US)

(72) Inventors: Walid M. Awni, Green Oaks, IL (US); Barry M. Bernstein, Mequon, WI (US); Andrew L. Campbell, Lake Forest, IL (US); Sandeep Dutta, Lincolnshire, IL (US); Chih-Wei Lin, Vernon Hills, IL (US); Wei Liu, Mundelein, IL (US); Rajeev M. Menon, Buffalo Grove, IL (US); Sven Mensing, Mannheim (DE); Thomas J. Podsadecki, Chicago, IL (US); Tianli Wang, Lake Bluff, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/431,906

(22) Filed: Feb. 14, 2017

(65) Prior Publication Data

US 2017/0151238 A1    Jun. 1, 2017

Related U.S. Application Data

(63) Continuation-in-part of application No. PCT/US2016/041334, filed on Jul. 7, 2016, and a continuation-in-part of application No. 14/676,370, filed on Apr. 1, 2015, now Pat. No. 10,286,029, which is a continuation-in-part of application No. 14/210,870, filed on Mar. 14, 2014, now abandoned.

(60) Provisional application No. 62/266,954, filed on Dec. 14, 2015, provisional application No. 62/190,045, filed on Jul. 8, 2015, provisional application No. 62/016,459, filed on Jun. 24, 2014, provisional application No. 61/989,951, filed on May 7, 2014, provisional application No. 61/973,929, filed on Apr. 24, 2014, provisional application No. 61/783,376, filed on Mar. 14, 2013.

(51) Int. Cl.
| A61K 31/498 | (2006.01) |
| A61K 31/454 | (2006.01) |
| A61K 38/05  | (2006.01) |
| A61K 38/06  | (2006.01) |

(52) U.S. Cl.
CPC .......... *A61K 31/498* (2013.01); *A61K 31/454* (2013.01); *A61K 38/05* (2013.01); *A61K 38/06* (2013.01)

(58) Field of Classification Search
None
See application file for complete search history.

(56) References Cited

U.S. PATENT DOCUMENTS

| 3,466,159 A | 9/1969 | Warshaw et al. |
| 3,492,386 A | 1/1970 | Ohmasa et al. |
| 3,648,037 A | 3/1972 | Tew, Jr. |
| 3,680,106 A | 7/1972 | Foley |
| 3,685,984 A | 8/1972 | Layne et al. |
| 3,809,265 A | 5/1974 | Krenke et al. |
| 3,853,176 A | 12/1974 | Henrich |
| 3,937,150 A | 2/1976 | Miericke et al. |
| 5,683,999 A | 11/1997 | Jadhav et al. |
| 5,830,867 A | 11/1998 | Bhatnagar et al. |
| 5,935,982 A | 8/1999 | Dykstra et al. |
| 6,042,847 A | 3/2000 | Kerc et al. |
| 6,235,493 B1 | 5/2001 | Bissell et al. |
| 6,369,091 B1 | 4/2002 | Sircar et al. |
| 6,388,093 B1 | 5/2002 | Chamberlain et al. |
| 6,599,528 B1 | 7/2003 | Rosenberg et al. |
| 6,703,403 B2 | 3/2004 | Norbeck et al. |
| 6,846,802 B2 | 1/2005 | Chen et al. |
| 6,881,741 B2 | 4/2005 | Chan et al. |
| 6,919,366 B2 | 7/2005 | Sircar et al. |
| 6,923,988 B2 | 8/2005 | Patel et al. |
| 7,065,453 B1 | 6/2006 | Diller et al. |
| 7,141,574 B2 | 11/2006 | Beaulieu et al. |
| 7,183,270 B2 | 2/2007 | Cherney et al. |
| 7,368,452 B2 | 5/2008 | Nakajima et al. |
| 7,488,832 B2 | 2/2009 | Cole et al. |
| 7,582,605 B2 | 9/2009 | Moore et al. |

(Continued)

FOREIGN PATENT DOCUMENTS

| BR | PI0401908 A | 1/2006 |
| DE | 75755 C | 6/1894 |

(Continued)

OTHER PUBLICATIONS

Franciscus, HCSP fact sheet, download online on Mar. 22, 2017 from URL:<www.hcvadvocate.org>.*
EASL (EASL Clinical Practice Guidelines, J. Hepatol., 2011, 55, p. 245-264).*
Lok et al. (61th Annual Meeting of the American Association for the Study of Liver Diseases, Boston, 2010).*
Walpole et al. (BMC Public Health 2012, 12:439).*
Lawitz et al. (Antimicrob Agents Chemother. Dec. 28, 2015;60(3):1546-55) (Year: 2015).*
Kiser et al. (Nat Rev Gastroenterol Hepatol. Oct. 2013; 10(10): 596-606) (Year: 2013).*
Extended European Search Report for Application Np. EP18156337, dated Jun. 15, 2018, 7 pages.

(Continued)

*Primary Examiner* — Sergio Coffa

(57) ABSTRACT

The present invention features interferon-free therapies for the treatment of HCV. Preferably, the treatment is over a shorter duration of treatment, such as no more than 12 weeks. In one aspect, the treatment comprises administering at least two direct acting antiviral agents to a subject with HCV infection, wherein the treatment lasts for 12 weeks and does not include administration of either interferon or ribavirin, and said at least two direct acting antiviral agents comprise (a) Compound 1 or a pharmaceutically acceptable salt thereof and (b) Compound 2 or a pharmaceutically acceptable salt thereof.

23 Claims, 9 Drawing Sheets

(56) References Cited

U.S. PATENT DOCUMENTS

| | | |
|---|---|---|
| 7,659,270 B2 | 2/2010 | Bachand et al. |
| 7,704,992 B2 | 4/2010 | Bachand et al. |
| 7,728,027 B2 | 6/2010 | Pack et al. |
| 7,732,457 B2 | 6/2010 | Malamas et al. |
| 7,741,347 B2 | 6/2010 | Bachand et al. |
| 7,745,636 B2 | 6/2010 | Bachand et al. |
| 7,759,495 B2 | 7/2010 | Bachand et al. |
| 7,763,731 B2 | 7/2010 | Rockway et al. |
| 7,906,655 B2 | 3/2011 | Belema et al. |
| 8,101,643 B2 | 1/2012 | Qiu et al. |
| 8,466,159 B2 | 6/2013 | Bernstein et al. |
| 8,492,386 B2 | 7/2013 | Bernstein et al. |
| 8,648,037 B2 | 2/2014 | Or et al. |
| 8,680,106 B2 | 3/2014 | Bernstein et al. |
| 8,685,984 B2 | 4/2014 | Bernstein et al. |
| 8,691,938 B2 | 4/2014 | Degoey et al. |
| 8,809,265 B2 | 8/2014 | Bernstein et al. |
| 8,853,176 B2 | 10/2014 | Bernstein et al. |
| 8,921,514 B2 | 12/2014 | Degoey et al. |
| 8,936,781 B2 | 1/2015 | Gai et al. |
| 8,937,150 B2 | 1/2015 | Degoey et al. |
| 8,969,357 B2 | 3/2015 | Bernstein et al. |
| 8,993,578 B2 | 3/2015 | Bernstein et al. |
| 9,006,387 B2 | 4/2015 | Wagner et al. |
| 9,220,748 B2 | 12/2015 | Or et al. |
| 9,278,922 B2 | 3/2016 | Donner et al. |
| 10,286,029 B2 * | 5/2019 | Awni .................. A61K 31/498 |
| 2002/0183319 A1 | 12/2002 | Liang et al. |
| 2003/0004203 A1 | 1/2003 | Sircar et al. |
| 2003/0100582 A1 | 5/2003 | Sircar et al. |
| 2004/0013697 A1 | 1/2004 | Berndl et al. |
| 2004/0034189 A1 | 2/2004 | Cho et al. |
| 2004/0106559 A1 | 6/2004 | Wang et al. |
| 2004/0266668 A1 | 12/2004 | Nakajima et al. |
| 2005/0075343 A1 | 4/2005 | Sircar et al. |
| 2005/0084529 A1 | 4/2005 | Rosenberg et al. |
| 2005/0120398 A1 | 6/2005 | Kalkeri et al. |
| 2005/0197375 A1 | 9/2005 | Sircar et al. |
| 2006/0003942 A1 | 1/2006 | Tung et al. |
| 2006/0052602 A1 | 3/2006 | Kim et al. |
| 2006/0058317 A1 | 3/2006 | Gravestock et al. |
| 2006/0105997 A1 | 5/2006 | Arrington et al. |
| 2007/0004741 A1 | 1/2007 | Apodaca et al. |
| 2007/0021330 A1 | 1/2007 | Wu et al. |
| 2007/0054842 A1 | 3/2007 | Blatt et al. |
| 2007/0060510 A1 | 3/2007 | Nakajima et al. |
| 2007/0142434 A1 | 6/2007 | Sandanayaka et al. |
| 2007/0197558 A1 | 8/2007 | Betebenner et al. |
| 2007/0232627 A1 | 10/2007 | Betebenner et al. |
| 2007/0232645 A1 | 10/2007 | Rockway et al. |
| 2007/0299068 A1 | 12/2007 | Karp et al. |
| 2007/0299078 A1 | 12/2007 | Niu et al. |
| 2008/0008681 A1 | 1/2008 | Niu et al. |
| 2008/0032936 A1 | 2/2008 | Gai et al. |
| 2008/0039375 A1 | 2/2008 | Moore et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0075696 A1 | 3/2008 | Parsons et al. |
| 2008/0221107 A1 | 9/2008 | Giordanetto et al. |
| 2008/0267916 A1 | 10/2008 | Gai et al. |
| 2008/0267917 A1 | 10/2008 | Niu et al. |
| 2008/0287449 A1 | 11/2008 | Niu et al. |
| 2008/0299075 A1 | 12/2008 | Bachand et al. |
| 2008/0311075 A1 | 12/2008 | Bachand et al. |
| 2009/0004111 A1 | 1/2009 | Rice et al. |
| 2009/0036444 A1 | 2/2009 | Mizojiri et al. |
| 2009/0041716 A1 | 2/2009 | Kim et al. |
| 2009/0043107 A1 | 2/2009 | Pack et al. |
| 2009/0068140 A1 | 3/2009 | Bachand et al. |
| 2009/0075869 A1 | 3/2009 | Holloway et al. |
| 2009/0093456 A1 | 4/2009 | Arnold et al. |
| 2009/0104151 A1 | 4/2009 | Hanson et al. |
| 2009/0123425 A1 | 5/2009 | Moore et al. |
| 2009/0142299 A1 | 6/2009 | Sun et al. |
| 2009/0180981 A1 | 7/2009 | Niu et al. |
| 2009/0180984 A1 | 7/2009 | Sun et al. |
| 2009/0180985 A1 | 7/2009 | Liu et al. |
| 2009/0191151 A1 | 7/2009 | Gai et al. |
| 2009/0197888 A1 | 8/2009 | Gai et al. |
| 2009/0202478 A1 | 8/2009 | Bachand et al. |
| 2009/0202483 A1 | 8/2009 | Bachand et al. |
| 2009/0238794 A1 | 9/2009 | Gai et al. |
| 2009/0274657 A1 | 11/2009 | Gai et al. |
| 2010/0003214 A1 | 1/2010 | Gai et al. |
| 2010/0021540 A1 | 1/2010 | Gopinathan et al. |
| 2010/0029666 A1 | 2/2010 | Harper et al. |
| 2010/0055071 A1 | 3/2010 | Leivers et al. |
| 2010/0068176 A1 | 3/2010 | Belema et al. |
| 2010/0074863 A1 | 3/2010 | Or et al. |
| 2010/0080772 A1 | 4/2010 | Belema et al. |
| 2010/0143499 A1 | 6/2010 | Condon |
| 2010/0158862 A1 | 6/2010 | Kim et al. |
| 2010/0160355 A1 | 6/2010 | Degoey et al. |
| 2010/0168138 A1 | 7/2010 | Degoey et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2010/0317568 A1 | 12/2010 | Degoey et al. |
| 2011/0008288 A1 | 1/2011 | Or et al. |
| 2011/0033420 A1 | 2/2011 | Gai et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0123496 A1 | 5/2011 | Gai et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0189129 A1 | 8/2011 | Qiu et al. |
| 2011/0195044 A1 | 8/2011 | Romine |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2012/0004196 A1 * | 1/2012 | DeGoey ............ C07D 401/14 514/63 |
| 2012/0028978 A1 | 2/2012 | Zhong et al. |
| 2012/0040977 A1 | 2/2012 | Li et al. |
| 2012/0070416 A1 * | 3/2012 | Or ..................... C07K 5/06034 424/85.6 |
| 2012/0076756 A1 | 3/2012 | Qiu et al. |
| 2012/0114600 A1 | 5/2012 | McKinnell et al. |
| 2012/0122864 A1 | 5/2012 | Zhong et al. |
| 2012/0172290 A1 | 7/2012 | Krueger et al. |
| 2012/0220506 A1 | 8/2012 | Qin et al. |
| 2012/0220562 A1 | 8/2012 | Degoey et al. |

(56) References Cited

U.S. PATENT DOCUMENTS

| | | |
|---|---|---|
| 2013/0102026 A1 | 4/2013 | Borody |
| 2013/0102525 A1 | 4/2013 | Bernstein et al. |
| 2013/0102526 A1 | 4/2013 | Bernstein et al. |
| 2013/0102557 A1 | 4/2013 | Bernstein et al. |
| 2013/0102558 A1 | 4/2013 | Bernstein et al. |
| 2014/0024579 A1 | 1/2014 | Bernstein et al. |
| 2014/0057835 A1 | 2/2014 | Bernstein et al. |
| 2014/0080868 A1 | 3/2014 | Ng et al. |
| 2014/0080869 A1 | 3/2014 | Krishnan et al. |
| 2014/0107016 A1 | 4/2014 | Bernstein et al. |
| 2014/0107017 A1 | 4/2014 | Bernstein et al. |
| 2014/0210870 A1 | 7/2014 | Atkins et al. |
| 2014/0274934 A1 | 9/2014 | Bernstein et al. |
| 2014/0275099 A1 | 9/2014 | Bernstein et al. |
| 2014/0323395 A1 | 10/2014 | Bernstein et al. |
| 2015/0004196 A1 | 1/2015 | Perricone |
| 2015/0011481 A1 | 1/2015 | Vilchez et al. |
| 2015/0024999 A1 | 1/2015 | Awni et al. |
| 2015/0196615 A1 | 7/2015 | Awni et al. |
| 2015/0283198 A1 | 10/2015 | Awni et al. |
| 2017/0088583 A1 | 3/2017 | Or et al. |
| 2017/0157104 A1 | 6/2017 | Bellizzi et al. |
| 2017/0333428 A1 | 11/2017 | Collins et al. |
| 2017/0360783 A1 | 12/2017 | Collins et al. |
| 2019/0336565 A1 | 11/2019 | Awni et al. |

FOREIGN PATENT DOCUMENTS

| | | |
|---|---|---|
| EP | 2242751 A1 | 10/2010 |
| EP | 2583677 A2 | 4/2013 |
| EP | 2968301 B1 | 4/2017 |
| JP | 2003282270 A | 10/2003 |
| JP | 2007320925 A | 12/2007 |
| JP | 2010126571 A | 6/2010 |
| JP | 2013538235 A | 10/2013 |
| JP | 6441303 B2 | 12/2018 |
| RU | 2286343 C2 | 10/2006 |
| WO | WO-9427627 A1 | 12/1994 |
| WO | WO-9961020 A1 | 12/1999 |
| WO | WO-0000179 A1 | 1/2000 |
| WO | WO-0012521 A1 | 3/2000 |
| WO | WO-0177113 A2 | 10/2001 |
| WO | WO-0214314 A2 | 2/2002 |
| WO | WO-03068738 A1 | 8/2003 |
| WO | WO-03082186 A2 | 10/2003 |
| WO | WO-03099274 A1 | 12/2003 |
| WO | WO-2004005283 A1 | 1/2004 |
| WO | WO-04014313 A2 | 2/2004 |
| WO | WO-2004014852 A2 | 2/2004 |
| WO | WO-04014852 A3 | 4/2004 |
| WO | WO-2004014313 A3 | 12/2005 |
| WO | WO-2006020951 A1 | 2/2006 |
| WO | WO-2006033703 A1 | 3/2006 |
| WO | WO-2006093867 A1 | 9/2006 |
| WO | WO-06119061 A2 | 11/2006 |
| WO | WO-2006133326 A1 | 12/2006 |
| WO | WO-2007015787 A1 | 2/2007 |
| WO | WO-2007015855 A1 | 2/2007 |
| WO | WO-2007016441 A1 | 2/2007 |
| WO | WO-2007070556 A2 | 6/2007 |
| WO | WO-2007070600 A2 | 6/2007 |
| WO | WO-2007076034 A2 | 7/2007 |
| WO | WO-2007076035 A2 | 7/2007 |
| WO | WO-2007081517 A2 | 7/2007 |
| WO | WO-2007082554 A1 | 7/2007 |
| WO | WO-2007070556 A3 | 8/2007 |
| WO | WO-2007081517 A8 | 9/2007 |
| WO | WO-2007070600 A3 | 11/2007 |
| WO | WO-2007131366 A1 | 11/2007 |
| WO | WO-2007131966 A1 | 11/2007 |
| WO | WO-2007144174 A1 | 12/2007 |
| WO | WO-2007148135 A1 | 12/2007 |
| WO | WO-2008014236 A1 | 1/2008 |
| WO | WO-2008014238 A2 | 1/2008 |
| WO | WO-2008021927 A2 | 2/2008 |
| WO | WO-2008021928 A2 | 2/2008 |
| WO | WO-2008021936 A2 | 2/2008 |
| WO | WO-2008021928 A3 | 3/2008 |
| WO | WO-2008021936 A3 | 4/2008 |
| WO | WO-2008021927 A3 | 5/2008 |
| WO | WO-2008051475 A2 | 5/2008 |
| WO | WO-2008051477 A2 | 5/2008 |
| WO | WO-2008051514 A2 | 5/2008 |
| WO | WO-2008057208 A2 | 5/2008 |
| WO | WO-2008057209 A1 | 5/2008 |
| WO | WO-2008064218 A2 | 5/2008 |
| WO | WO-2008070447 A2 | 6/2008 |
| WO | WO-2008074450 A2 | 6/2008 |
| WO | WO-2008064218 A3 | 10/2008 |
| WO | WO-2008128121 A1 | 10/2008 |
| WO | WO-2008133753 A2 | 11/2008 |
| WO | WO-2008144380 A1 | 11/2008 |
| WO | WO-2009003009 A1 | 12/2008 |
| WO | WO-2009010804 A1 | 1/2009 |
| WO | WO-2009020534 A2 | 2/2009 |
| WO | WO-2009020825 A1 | 2/2009 |
| WO | WO-2009020828 A1 | 2/2009 |
| WO | WO-2008070447 A3 | 3/2009 |
| WO | WO-2009064975 A1 | 5/2009 |
| WO | WO-2009093082 A1 | 7/2009 |
| WO | WO-2009094224 A1 | 7/2009 |
| WO | WO-2009102318 A1 | 8/2009 |
| WO | WO-2009102325 A1 | 8/2009 |
| WO | WO-2009102568 A1 | 8/2009 |
| WO | WO-2009102633 A1 | 8/2009 |
| WO | WO-2009102694 A1 | 8/2009 |
| WO | WO-2009108507 A1 | 9/2009 |
| WO | WO-2009134624 A1 | 11/2009 |
| WO | WO-2009136290 A1 | 11/2009 |
| WO | WO-2009143361 A1 | 11/2009 |
| WO | WO-2009155709 A1 | 12/2009 |
| WO | WO-2010015090 A1 | 2/2010 |
| WO | WO-2010017035 A2 | 2/2010 |
| WO | WO-2010017401 A1 | 2/2010 |
| WO | WO-2010039793 A1 | 4/2010 |
| WO | WO-2010059858 A1 | 5/2010 |
| WO | WO-2010062821 A1 | 6/2010 |
| WO | WO-2010065668 A1 | 6/2010 |
| WO | WO-2010065674 A1 | 6/2010 |
| WO | WO-2010065681 A1 | 6/2010 |
| WO | WO-2010075376 A2 | 7/2010 |
| WO | WO-2010091413 A1 | 8/2010 |
| WO | WO-2010096302 A1 | 8/2010 |
| WO | WO-2010096462 A1 | 8/2010 |
| WO | WO-2010096777 A1 | 8/2010 |
| WO | WO-2010099527 A1 | 9/2010 |
| WO | WO-2010111483 A1 | 9/2010 |
| WO | WO-2010111534 A1 | 9/2010 |
| WO | WO-2010111673 A1 | 9/2010 |
| WO | WO-2010115767 A1 | 10/2010 |
| WO | WO-2010117635 A1 | 10/2010 |
| WO | WO-2010117704 A1 | 10/2010 |
| WO | WO-2010117977 A1 | 10/2010 |
| WO | WO-2010120621 A1 | 10/2010 |
| WO | WO-2010120935 A1 | 10/2010 |
| WO | WO-2010122162 A1 | 10/2010 |
| WO | WO-2010132538 A1 | 11/2010 |
| WO | WO-2010132601 A1 | 11/2010 |
| WO | WO-2010138368 A1 | 12/2010 |
| WO | WO-2010138488 A1 | 12/2010 |
| WO | WO-2010138790 A1 | 12/2010 |
| WO | WO-2010138791 A1 | 12/2010 |
| WO | WO-2010144646 A2 | 12/2010 |
| WO | WO-2010148006 A1 | 12/2010 |
| WO | WO-2011004276 A1 | 1/2011 |
| WO | WO-2011009084 A2 | 1/2011 |
| WO | WO-2011014487 A1 | 2/2011 |
| WO | WO-2011015658 A1 | 2/2011 |
| WO | WO-2011026920 A1 | 3/2011 |
| WO | WO-2011028596 A1 | 3/2011 |
| WO | WO-2011031904 A1 | 3/2011 |
| WO | WO-2011031934 A1 | 3/2011 |
| WO | WO-2011050146 A1 | 4/2011 |
| WO | WO-2011054834 A1 | 5/2011 |

(56) References Cited

FOREIGN PATENT DOCUMENTS

| | | |
|---|---|---|
| WO | WO-2011059850 A1 | 5/2011 |
| WO | WO-2011059887 A1 | 5/2011 |
| WO | WO-2011060000 A1 | 5/2011 |
| WO | WO-2011066241 A1 | 6/2011 |
| WO | WO-2011068941 A2 | 6/2011 |
| WO | WO-2011075439 A1 | 6/2011 |
| WO | WO-2011075607 A1 | 6/2011 |
| WO | WO-2011075615 A1 | 6/2011 |
| WO | WO-2011079327 A1 | 6/2011 |
| WO | WO-2011081918 A1 | 7/2011 |
| WO | WO-2011082077 A1 | 7/2011 |
| WO | WO-2011087740 A1 | 7/2011 |
| WO | WO-2011091417 A1 | 7/2011 |
| WO | WO-2011091446 A1 | 7/2011 |
| WO | WO-2011091532 A1 | 8/2011 |
| WO | WO-2011112429 A1 | 9/2011 |
| WO | WO-2011119853 A1 | 9/2011 |
| WO | WO-2011119858 A1 | 9/2011 |
| WO | WO-2011119860 A1 | 9/2011 |
| WO | WO-2011119870 A1 | 9/2011 |
| WO | WO-2011127350 A1 | 10/2011 |
| WO | WO-2011146401 A1 | 11/2011 |
| WO | WO-2011150243 A1 | 12/2011 |
| WO | WO-2011156543 A2 | 12/2011 |
| WO | WO-2011156578 A1 | 12/2011 |
| WO | WO-2012039717 A1 | 3/2012 |
| WO | WO-2012040040 A1 | 3/2012 |
| WO | WO-2012040167 A1 | 3/2012 |
| WO | WO-2012040389 A2 | 3/2012 |
| WO | WO-2012040923 A1 | 4/2012 |
| WO | WO-2012040924 A1 | 4/2012 |
| WO | WO-2012041014 A1 | 4/2012 |
| WO | WO-2012041227 A1 | 4/2012 |
| WO | WO-2012050848 A1 | 4/2012 |
| WO | WO-2012050850 A1 | 4/2012 |
| WO | WO-2012051361 A1 | 4/2012 |
| WO | WO-2012068234 A2 | 5/2012 |
| WO | WO-2012074437 A2 | 6/2012 |
| WO | WO-2012087976 A2 | 6/2012 |
| WO | WO-2012116257 A1 | 8/2012 |
| WO | WO-2014047039 A1 | 3/2014 |
| WO | WO-2014047046 A1 | 3/2014 |
| WO | WO-2014099908 A1 | 6/2014 |
| WO | WO-2014152514 A1 | 9/2014 |
| WO | WO-2015061742 A2 | 4/2015 |
| WO | WO-2015153792 A1 | 10/2015 |
| WO | WO-2015153793 A1 | 10/2015 |
| WO | WO-2017007934 A1 | 1/2017 |

OTHER PUBLICATIONS

Einav S., et al., "The Hepatitis C Virus (HCV) Ns4b RNA Binding Inhibitor Clemizole is Highly Synergistic with HCV Protease Inhibitors," The Journal of Infectious Diseases, 2010, vol. 202 (1), pp. 65-74.
Excerpts for Corresponding U.S. Appl. No. 14/210,858.
Excerpts for Corresponding U.S. Appl. No. 14/210,870.
*Gilead Sciences, Inc. et al.* v. *Abbott Laboratories, Inc. et al.* Case No. 13-2034, U.S. District Court for the District of Delaware. Order Construsing the Terms of U.S. Pat. No. 8,466,159 & U.S. Pat. No. 8,492,386. Dated Nov. 3, 2015.
Grünberger C., et al., "3-Drug Synergistic Interaction of Small Molecular Inhibitors of Hepatitis C Virus Replication, Journal of Infectious Diseases," Journal of Infectious Diseases, 2008, vol. 197, pp. 42-45.
International Search Report and Written Opinion for Application No. PCT/US2014/027556, dated Jul. 2, 2014, 10 pages.
International Search Report and Written Opinion for Application no. PCT/US2015/023923, dated May 15, 2015, 10 pages.
International Search Report and Written Opinion for Application No. PCT/US2015/023923, dated May 19, 2015, 10 pages.
International Search Report and Written Opinion for Application No. PCT/US2016/041334, dated Oct. 24, 2016, 9 pages.
International Search Report for Application No. PCT/US2014/027423, dated Jun. 4, 2014, 3 pages.
Koev G., et al., "Antiviral Interactions of an HCV Polymerase Inhibitor with an HCV Protease Inhibitor or Interferon in Vitro," Antiviral Research, 2007, vol. 73 (1), pp. 78-83.
Lawitz E., et al., "A Phase 2a Trial of 12-Week Interferon-Free Therapy with Two Direct-Acting Antivirals (ABT-450/r, ABT-072) and Ribavirin in IL28B C/C Patients with Chronic Hepatitis C Genotype 1," Journal of Hepatology, 2013, vol. 19 (1), pp. 18-23.
Legrand-Abravanel F., et al., "Hepatitis C Virus Genotype 5: Epidemiological Characteristics and Sensitivity to Combination Therapy with Interferon-Alpha Plus Ribavirin," The Journal of Infectious Diseases, 2004, vol. 189 (8), pp. 1397-1400.
Lok Anna S., et al., "Combination Therapy with BMS-790052 and Bms-650032 alone or with PEGIFN/RBV Results in Undetectable HCV RNA Through 12 Weeks of Therapy in HCV Genotype 1 Null Responders," Hepatology, Wiley, USA, 2010, vol. 52 (4, Suppl 1), pp. 877A.
Notice of Opposition for European Patent No. EP14719977.2 dated Jan. 25, 2010, 151 pages.
Prichard M.N., et al., "A Three-Dimensional Model to Analyze Drug-Drug Interactions," Antiviral Research, 1990, vol. 14 (4-5), pp. 181-206.
Tanabe Y., et al., "Synergistic Inhibition of Intracellular Hepatitis C Virus Replication by Combination of Ribavirin and Interferon-a," The Journal of Infectious Diseases, 2004, vol. 189 (7), pp. 1129-1139.
Wyles D.L., et al., "Synergy of Small Molecular Inhibitors of Hepatitis C Virus Replication Directed at Multiple Viral Targets," Journal of Virology, 2007, vol. 81 (6), pp. 3005-3008.
European search report for Application No. EP17196993, dated May 8, 2018, 9 pages.
FDA Guideline for Submitting Supporting Documentation TM8-TM14 (filed with response to Notice of Opposition) in Advancing Health through Innovation, 2017 New Drug Therapy Approvals, 2017, 102 pages.
Jules Levin: "Magellan-2: Safety and Efficacy of Glecaprevir/Pibrentasvir in Liver or Renal Transplant Adults With Chronic Hepatitis C Genotype 1-6 Infection", Apr. 22, 2017 (Apr. 22, 2017), XP055466892, Retrieved from the Internet: URL:http://www.natap.org/2017/EASL/EASL_32.htm [retrieved on Apr. 12, 2018].
Franciscus, HCSP Fact Sheet, [online] [Retreived on Apr. 12, 2018]. Retreived from the Internet:<url:<a="" href="http://www.hcvadvocate.org">www.hcvadvocate.org</url:>.
Response to Notice of Opposition for European Patent No. EP2968301 dated Jun. 18, 2018, 18 pages.
Gane, E., et al., "High Efficacy of ABT-493 and ABT-530 Treatment in Patients With HCV Genotype 1 or 3 Infection and Compensated Cirrhosis," Gastroenterology, Oct. 2016 , vol. 151 (4), pp. 651-659.
Kwo, P.Y., et al., "Glecaprevir and Pibrentasvir Yield High Response Rates in Patients With HCV Genotype 1-6 Without Cirrhosis," Journal of Hepatology, Aug. 2017 , vol. 67 (2), pp. 263-271.
Mendizabal, M., et al., "Chronic Hepatitis C and Chronic Kidney Disease: Advances, Limitations and Unchartered Territories," Journal of Viral Hepatitis, Jun. 2017 , vol. 24 (6), pp. 442-453.
Poordad, F., et al., "Glecaprevir and Pibrentasvir for 12 Weeks for Hepatitis C Virus Genotype 1 Infection and Prior Direct-acting Antiviral Treatment," Hepatology, Aug. 2017 , vol. 66 (2), pp. 389-397.
Reau N., et al., "Magellan-2: Safety and Efficacy of Glecaprevir/pibrentasvir in Liver or Renal Transplant Adults with Chronic Hepatitis C Genotype 1-6 Infection," Journal of Hepatology, Apr. 2017, vol. 66 (1), pp. S90-S91.
Verna, E.C., et al., "HCV Antiviral Therapy in Liver Transplant Candidates and Recipients With Renal Insufficiency," Transplantation, May 2017, vol. 101 (5), pp. 924-932.
Abagyan R., et al., "ICM—A New Method for Protein Modeling and Design: Applications to Docking and Structure Prediction from the Distorted Native Conformation," Journal of Computational Chemistry, 1994, vol. 15 (5), pp. 488-506.
Adjabeng G., et al., "Novel Class of Tertiary Phosphine Ligands Based on a Phospha-adamantane Framework and use in the Suzuki

(56) References Cited

OTHER PUBLICATIONS cross-Coupling Reactions of Aryl Halides Under Mild Conditions," Organic Letters, 2003, vol. 5 (6), pp. 953-955.
Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.
Aldous D.J., et al. , "A Simple Enantioselective Preparation of (2S,5S)-2,5-diphenylpyrrolidine and Related Diaryl Amines," Tetrahedron Asymmetry, 2000, vol. 11, pp. 2455-2462.
Alesso E.N., et al., "Synthesis of Diastereoisomeric 1,2,3-Triphenylindans," Australian Journal of Chemistry, 1997, vol. 50, pp. 149-152.
Altschuel S.F., et al., "Basic Local Alignment Search Tool," Journal of Molecular Biology, 1990, vol. 215 (3), pp. 403-410.
Altschul S.F., et al., "Gapped BLAST and PSI-BLAST: A New Generation of Protein Database Search Programs," Nucleic Acids Research, 1997, vol. 25 (17), pp. 3389-3402.
Angiolini M., et al., "Synthesis of Azabicycloalkane Amino Acid Scaffolds as Reverse-Turn Inducer Dipeptide Mimics ," European Journal Organization Chemistry, 2000, vol. 2000 (14), pp. 2571-2581.
Arner E.S., and Eriksson S., "Mammalian Deoxyribonucleoside Kinases," Pharmacology & Therapeutics, 1995, vol. 67(2), pp. 155-186.
Baker D., et al., "Protein Structure Prediction and Structural Genomics," Science, 2001, vol. 294 (5540), pp. 93-96.
Bartenschlager R., "Hepatitis C Virus Molecular Clones: From cDNA to Infectious Virus Particles in Cell Culture," Current Opinion in Microbiology, 2006, vol. 9 (4), pp. 416-422.
Bartenschlager R., "Hepatitis C Virus Replicons: Potential Role for Drug Development," Nature Reviews Drug Discovery, 2002, vol. 1 (11), pp. 911-916.
Beaumont, K., et al., "Design of Ester Prodrugs to Enhance Oral Absorption of Poorly Permeable Compounds Challenges to the Discovery Scientist," Current Drug Metabolism, 2003, vol. 4 (6), pp. 461-485.
Boehm T., et al., "Uber Die Bildung Von Gamma-Piperidonderivaten Aus Azetessigester, Aromatischen Aldehyden and Aminen, Eine Modifikation Der Hantzschschen Pyridinsynthese," Pharmaceutical,1943, vol. 281, pp. 62-77.
Bohm H.J., "The Computer Program LUDI: A New Method for the De Novo Design of Enzyme Inhibitors," Journal of Computer-Aided Molecular Design, 1992, vol. 6 (1), pp. 61-78.
Breitenbach J., et al., "Confocal Raman-Spectroscopy: Analytical Approach to Solid Dispersions and Mapping of Drugs," 1999, vol. 16 (7), pp. 1109-1113.
Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.
Brunger A.T., et al., "Recent Developments for the Efficient Crystallographic Refinement of Macromolecular Structures," Current Opinion in Structural Biology, 1998, vol. 8 (5), pp. 606-611.
Bundgaard H., ed., "Design of prodrugs," Elsevier, 1985, pp. 7-9 and 21-24.
Bundgaard H., ed., in: Design of Prodrugs, Elsevier Science, 1985, Table of Contents.
Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Structure-Activity Relationships," Journal of Medicinal Chemistry, 2008, vol. 51 (17), pp. 5243-5263.
Chiou W.L., et al., "Pharmaceutical Applications of Solid Dispersion Systems," Journal of Pharmaceutical Sciences, 1971, vol. 60 (9), pp. 1281-1302.

Chong J.M., et al. , "Asymmetric Synthesis of trans.2,5-Diphenylpyrrolidine: A C2-Symmetric Chirai Amine," Tetrahedron Asymmetry, 1995, vol. 6 (2), pp. 409-418.
Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.
Clarke P.A., et al., "Pot, Atom and Step Economic (PASE) Synthesis of Highly Functionalized Piperidines: A Five-Component Condensation," Tetrahedron Letters , 2007, vol. 48 , pp. 5209-5212.
Clarke P.A., et al., "Pot, Atom and Step Economic (PASE) Synthesis of Highly Substituted Piperidines:A Five-Component Condensation," Synthesis, 2008, No. 28, pp. 3530-3532.
Collado I., et al , "Stereoselective Addition of Grignard-Derived Organocopper Reagents to N-Acyliminium Ions: Synthesis of Enantiopure 5- and 4,5-Substituted Prolinates ," Journal of Organic Chemistry , 1995, vol. 60, pp. 5011-5015.
Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.
Cornell, W.D., et al., "A Second Generation Force Field for the Simulation of Proteins, Nucleic Acids, and Organic Molecules," Journal of the American Chemical Society, 1995, vol. 117 (19), pp. 5179-5197.
Cortesi P.A., et al., "Cost-Effectiveness of New Direct-Acting Antivirals to Prevent Post-Liver Transplant Recurrent Hepatitis," American Journal of Transplantation, Jul. 2015, vol. 15 (7), pp. 1817-1826.
De Francesco R., et al., "Challenges and Successes in Developing New Therapies for Hepatitis C," Nature, 2005, vol. 436 (7053), pp. 953-960.
Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.
Dore G.J.,"The Changing Therapeutic Landscape for Hepatitis C," The Medical Journal of Australia, Jun. 2012, vol. 196 (10), pp. 629-632.
Effenberger F., et al., "Synthesis, Structure, and Spectral Behavior of Donor-Acceptor Substituted Biphenyls," The Journal of Organic Chemistry, 1983, vol. 48 (24), pp. 4649-4658.
Eldridge M.D., et al., "Empirical Scoring Functions: I. The Development of a Fast Empirical Scoring Function to Estimate the Binding Affinity of Ligands in Receptor Complexes," Journal of Computer Aided Molecular Design, 1997, vol. 11 (5), pp. 425-445.
Eswar N., et al., "Comparative Protein Structure Modeling Using Modeller," Current Protocols in Bioinformatics, 2006, Suppl. 15, 5.6.1-5.6.30.
Ettmayer P., et al., "Lessons Learned from Marketed and Investigational Prodrugs," Journal of Medicinal Chemistry, 2004, vol. 47 (10), pp. 2393-2404.
European Search Report for Application No. EP12155991, dated Mar. 29, 2012, 2 pages.
European Search Report for Application No. EP11160830, dated Aug. 12, 2011, 2 pages.
European Search Report for Application No. EP13191041, dated Dec. 9, 2013, 2 pages.
European Search Report for Application No. EP13191049, dated Dec. 13, 2013, 2 pages.
European Search Report for Application No. EP18196401.6, dated Dec. 11, 2018, 8 pages.
Excipients & Activities for Pharma, ExAct, No. 20, May 2008.
Extended European Search Report for Application No. EP13167828, dated Jun. 21, 2013, 6 pages.
Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.
Feig M., et al., "Performance Comparison of Generalized Born and Poisson Methods in the Calculation of Electrostatic Solvation Energies for Protein Structures," Journal of Computational Chemistry, 2004, vol. 25 (2), pp. 265-284.

(56) References Cited

OTHER PUBLICATIONS

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.
Fiser A., et al., "Modeling of Loops in Protein Structures," Protein Science, 2000, vol. 9 (9), pp. 1753-1773.
Forster A., et al., "Selection of Excipients for Melt Extrusion with Two Poorly Water-Soluble Drugs by Solubility Parameter Calculation and Thermal Analysis," 2001, vol. 226, pp. 147-161.
Galun E., et al., "Hepatitis C Virus Viremia in SCID-BNX Mouse Chimera," Journal of Infectious Diseases, 1995, vol. 172 (1), pp. 25-30.
Gastreich M., et al., "Ultrafast De Novo Docking Combining Pharmacophores and Combinatorics," Journal of Computer-Aided Molecular Design, 2006, vol. 20 (12), pp. 717-734.
Gentry G.A., "Viral Thymidine Kinases and their Relatives," Pharmacology & Therapeutics, 1992, vol. 54(3), pp. 319-355.
Gillet V., et al., "SPROUT: A Program for Structure Generation," Journal of Computer-Aided Molecular Design, 1993, vol. 7 (2), pp. 127-153.
Gohlke H., et al., "Approaches to the Description and Prediction of the Binding Affinity of Small-Molecule Ligands to Macromolecular Receptors," Angewandte Chemie International Edition, 2002, vol. 41 (15), pp. 2644-2676.
Goodford P.J., "A Computational Procedure for Determining Energetically Favorable Binding Sites on Biologically Important Macromolecules," Journal of Medicinal Chemistry, 1985, vol. 28 (7), pp. 849-857.
Goodsell D.S., et al., "Automated Docking of Substrates to Proteins by Simulated Annealing," Proteins, 1990, vol. 8 (3), pp. 195-202.
Gordon T.D., et al , "Synthetic Approaches to the Azole Peptide Mimetics," Tetrahedron Letters, 1993, vol. 34(12), pp. 1901-1904.
Greene T.W., et al., "Protection for the Amino group," Protective Groups in Organic Synthesis, 1999, Third Edition, pp. 494-653.
Greene T.W., et al., Protective Groups in Organic Synthesis, 3rd Edition, John Wiley and Sons, Inc., 1999, Preface, Table of Contents, Abbreviations.
Halfman C.J., et al., "Concentrations of Binding Protein and Labeled Analyte that are Appropriate for Measuring at any Analyte Concentration Range in Radioimmunoassays," Methods in Enzymology, 1981, vol. 74, pp. 481-497.
Halperin I., et al., "Principles of Docking: An Overview of Search Algorithms and a Guide to Scoring Functions," Proteins, 2002, vol. 47 (4), pp. 409-443.
Han H.K., et al., "Targeted Prodrug Design to Optimize Drug Delivery," AAPS PharmSci, 2000, vol. 2 (1), pp. 1-11.
Hartwig J.F., et al., "III.3.2 Palladium-Catalyzed Amination of Aryl Halides and Related Reactions," Handbook of Organopalladium Chemistry for Organic Synthesis, 2002, pp. 1051-1096.
Herbst D.A., et al., "Sofosbuvir, a Nucleotide Polymerase Inhibitor, for the Treatment of Chronic Hepatitis C Virus Infection," Expert opinion on investigational drugs, Apr. 2013, vol. 22(4), pp. 527-536.
Hoover J.E., Remington's Pharmaceutical Sciences, 15th Edition, 1975, Mack Publishing Co., Table of Contents.
Hubbard S.R., et al., "Src Autoinhibition: Let us Count the Ways," Nature Structural Biology, 1999, vol. 6 (8), pp. 711-714.
International Preliminary Report on Patentability and Written Opinion for Application No. PCT/US2009/069188, dated Jun. 29, 2011, 10 pages.
International Preliminary Report on Patentability and Written Opinion for the Application No. PCT/US2010/031102, dated Oct. 18, 2011, 7 pages.
International Search Report and Written Opinion for Application No. PCT/US2009/038077, dated Jan. 21, 2011, 15 pages.
International Search Report and Written Opinion for Application No. PCT/US2009/069177, dated Aug. 10, 2010, 17 pages.
International Search Report and Written Opinion for Application No. PCT/US2013/060103, dated Nov. 5, 2013, 8 pages.
International Search Report and Written Opinion for Application No. PCT/US2013/060118, dated Nov. 5, 2013, 10 pages.
International Search Report and Written Opinion for Application No. PCT/US2013/060122, dated Nov. 5, 2013, 9 pages.
International Search Report for Application No. PCT/US2009/069188, dated Jun. 8, 2010, 4 pages.
International Search Report for Application No. PCT/US2011/039769, dated Oct. 6, 2011, 4 pages.
International Search Report for Application No. PCT/US2011/052304, dated Jan. 31, 2012, 2 pages.
International Search Report for Application No. PCT/US2011/056045, dated Apr. 2, 2012, 4 pages.
International Search Report for Application No. PCT/US2011/065206, dated May 22, 2012, 3 pages.
International Search Report for Application No. PCT/US2011/065215, dated Jun. 12, 2012, 3 pages.
International Search Report for Application No. PCT/US2011/065224, dated Jun. 12, 2012, 3 pages.
International Search Report for Application No. PCT/US2011/065239, dated Jul. 30, 2012, 3 pages.
International Search Report for Application No. PCT/US2011/065242, dated May 22, 2012, 3 pages.
International Search Report for Application No. PCT/US2011/065247, dated Jun. 12, 2012, 3 pages.
International Search Report for Application No. PCT/US2011/065468, dated Mar. 26, 2012, 3 pages.
International Search Report for Application No. PCT/US2012/026456, dated Jun. 22, 2012, 3 pages.
International Search Report for the Application No. PCT/US2010/031102, dated Sep. 1, 2010, 4 pages.
Jacques et al., "Enantiomers, Racemates, and Resolutions," J. Wiley & Sons, Chapter 3, pp. 197-213, 1981.
Jeffrey J.L., et al., "Concise Synthesis of Pauciflorol F Using a Larock Annulation," Organic Letters, 2009, vol. 11 (23), pp. 5450-5453.
Jing Q., et al., "Bulky Achiral Triarylphosphines Mimic BINAP in Ru(II)-Catalyzed Asymmetric Hydrogenation of Ketones," Advanced Synthesis & Catalysis, 2005, vol. 347, pp. 1193-1197.
Jones G., et al., "Development and Validation of a Genetic Algorithm for Flexible Docking," Journal of Molecular Biology, 1997, vol. 267 (3), pp. 727-748.
Jones G., et al., "Docking Small-Molecule Ligands into Active Sites," Current Opinion in Biotechnology, 1995, vol. 6 (6), pp. 652-656.
Jones G., et al., "Molecular Recognition of Receptor Sites using a Genetic Algorithm with a Description of Desolvation," Journal of Molecular Biology, 1995, vol. 245 (1), pp. 43-53.
Kelly T.R., et al., "Bisubstrate Reaction Templates. Examination of the Consequences of Identical Versus Different Binding Sites," Journal of the American Chemical Society, 1990, vol. 112 (22), pp. 8024-8034.
Khan A.T., et al., "Effects of Substituents in the "-Position of 1,3-Dicarbonyl Compounds in Bromodimethylsulfonium Bromide-Catalyzed Multicomponent Reactions: A Facile Access to Functionalized Piperidines," Journal of organic chemistry, 2008, vol. 73 , pp. 8398-8402.
Kolykhalov A.A., et al., "Transmission of Hepatitis C by Intrahepatic Inoculation with Transcribed RNA," Science, 1997, vol. 277 (5325), pp. 570-574.
Kuethe J.T., et al., "Asymmetric Synthesis of 1,2,3-Trisubstituted Cyclopentanes and Cyclohexanes as Key Components of Substance P Antagonists," the Journal of Organic Chemistry, 2002, vol. 67 (17), pp. 5993-6000.
Kuntz I.D., et al., "A Geometric Approach to Macromolecule-Ligand Interactions," Journal of Molecular Biology, 1982, vol. 161 (2), pp. 269-288.
Lattman, E., "Use of the Rotation and Translation Functions," Meth. In Enzymol., 1985, 115, 55-77.
Levin J., ABT-493, a Potent HCV NS3/4A Protease Inhibitor with Broad Genotype Coverage, 21st Conference on Retroviruses and Opportunistic Infections Boston, MA, Mar. 3-6, 2014, 9 pages.
Lewis W., Dalakas M.C., "Mitochondrial Toxicity of Antiviral Drugs," Nature Medicine, 1995, vol. 1(5), pp. 417-422.
Lewis W., et al., "Fialuridine and its Metabolites Inhibit DNA Polymerase Gamma at Sites of Multiple Adjacent Analog Incorpo-

(56) References Cited

OTHER PUBLICATIONS ration, Decrease mtDNA Abundance, and Cause Mitochondrial Structural Defects in Cultured Hepatoblasts," Proceedings of the National Academy of Sciences of the USA, 1996, vol. 93(8), pp. 3592-3597.

Li Chuan-Ying., et al., "Olefination of Ketenes for the Enantioselective Synthesis of Allenes via an Ylide Route," Tetrahedron, 2007, vol. 63, pp. 8046-8053.

Lieberman, H.A., et al., eds., Pharmaceutical Dosage Forms, vol. 1, Marcel Dekker, Inc., 1980, 5 pages.

Liverton N.J., et al., "Molecular Modeling Based Approach to Potent P2-P4 Macrocyclic Inhibitors of Hepatitis C NS3/4A Protease," Journal of the American Chemical Society, 2008, vol. 130 (14), pp. 4607-4609.

Lohmann V., et al., "Viral and Cellular Determinants of Hepatitis C Virus RNA Replication in Cell Culture," Journal of Virology, 2003, vol. 77 (5), pp. 3007-3019.

Louie J., et al., "Palladium-Catalyzed Amination of Aryl Triflates and Importance of Triflate Addition Rate," Journal of Organic Chemistry, 1997, vol. 62 (5), pp. 1268-1273.

L-selectride, Retrieved from the Internet:<URL: http://en.wikipedia.org/w/index.php"oldid=488453454>.

Lucas S., et al.,"In Vivo Active Aldosterone Synthase Inhibitors with Improved Selectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.

Marti-Renom M.A., et al., "Comparative Protein Structure Modeling of Genes and Genomes," Annual Review of Biophysics and Biomolecular Structure, 2000, vol. 29, pp. 291-325.

Masters K., "Spray Drying Handbook" 4th Edition, John Wiley & Sons, 1985, Table of Contents.

Masui M., et al., "A Practical Method for Asymmetric Borane Reduction of Prochiral Ketones Using Chiral Amino Alcohols and Trimethyl Borate," Synlett, 1997, pp. 273-274.

Matzeit A., et al., "Radical Tandem Cyclizations by Anodic Decarboxylation of Carboxylic Acids," Synthesis, 1995, pp. 1432-1444.

Mercer D.F., et al., "Hepatitis C Virus Replication in Mice with Chimeric Human Livers," Nature Medicine, 2001, vol. 7 (8), pp. 927-933.

Middleton T., et al., "A Replicon-based Shuttle Vector System for Assessing the Phenotype of HCV NS5B Polymerase Genes Isolated from Patient Populations," Journal of Virological Methods, 2007, vol. 145 (2), pp. 137-145.

Miranker A., et al., "Functionality Maps of Binding Sites: A Multiple Copy Simultaneous Search Method," Proteins, 1991, vol. 11 (1), pp. 29-34.

Misra M., et al., "Organocatalyzed Highly Atom Economic One Pot Synthesis of Tetrahydropyridines as Antimalarials," Bioorganic & Medicinal Chemistry, 2009, vol. 17, pp. 625-633.

Moinet C., et al., "Novel Non-Peptide Ligands for the Somatostatin sst3 Receptor," Bioorganic & Medicinal Chemistry Letters, 2001, vol. 11 (8), pp. 991-995.

Muci A.R., et al., "Practical Palladium Catalysts for C—N and C—O Bond Formation," Topics in Current Chemistry, 2002, vol. 219, pp. 131-209.

Muller C.E., et al., "Prodrug Approaches for Enhancing the Bioavailability of Drugs with Low Solubility," Chemistry & Biodiversity, 2009, vol. 6 (11), pp. 2071-2083.

Muri E.M.F., et al., "Pseudo-Peptides Derived From Isomannide as Potential Inhibitors of Serine Proteases," Amino Acids, 2005, vol. 28 (4), pp. 413-419.

Navaza J., "AMoRe: An Automated Package for Molecular Replacement," Acta Crystallographica, 1994, vol. A50 (2), pp. 157-163.

Naylor E.M., et al., "3-Pyridylethanolamines: Potent and Selective Human 63 Adrenergic Receptor Agonists," Bioorganic & Medicinal Chemistry Letters, 1998, vol. 8 (21), pp. 3087-3092.

Nevar N.M., et al., "One Step Preparation of 1,4-Diketones from Methyl Ketones and a-Bromomethyl Ketones in the Presence of ZnCl2•t-BuOH•Et2NR as a Condensation Agent," Synthesis, 2000, vol. 2000 (9), pp. 1259-1262.

Nishibata Y., et al., "Confirmation of Usefulness of a Structure Construction Program Based on Three-Dimensional Receptor Structure for Rational Lead Generation," Journal of Medicinal Chemistry, 1993, vol. 36 (20), pp. 2921-2928.

Notice of opposition dated Aug. 7, 2019 for European Application No. EP14725812filed Mar. 14, 2014, 172 pages.

Notice of Opposition dated Jan. 21, 2019 for European Patent EP2968301.

Notice of Opposition dated Jun. 22, 2018 to a European Patent EP2968302B1 in the name of Abbvie Inc.

Opposition filed by Sofia Salazar for Guatemala Application No. A20110074 (10046GTO1) dated Oct. 23, 2014, 10 pages.

Opposition filed by Sofia Salazar for Guatemala Application No. A201300093 (10046GTO2) dated Nov. 12, 2014, 12 pages.

Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.

Partial European Search Report for Application No. EP14190636, dated Feb. 24, 2015, 6 pages.

Peng T., et al., "Construction of a Library of Rhodol Fluorophores for Developing New Fluorescent Probes," Organic Letters, 2010, vol. 12 (3), pp. 496-499.

Penning T.D., et al, "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer ," Bioorganic & Medicinal Chemistry, 2008, vol. 16(14), pp. 6965-6975.

Pipili C. et al., "Management of Patients With Hepatitis B and C Before and After Liver and Kindly Transplantation," World Journal of Hepatology, May 27, 2014, vol. 6 (5), pp. 315-325.

Polymer Handbook, Brandrup J., et al., Eds., Interscience Publishers, 1975, Table of Contents, III-139-III-192.

Pre-Grant Opposition for Indian Application No. 1310/DELNP/2013 (100461NO2) dated Jul. 23, 2018, 47 Pages.

Rao S.N., et al., "Validation Studies of the Site-Directed Docking Program LibDock," Journal of Chemical Information and Modeling, 2007, vol. 47 (6), pp. 2159-2171.

Rarey M., et al., "A Fast Flexible Docking Method using an Incremental Construction Algorithm," Journal of Molecular Biology, 1996, vol. 261 (3), pp. 470-489.

Response to Opposition dated Feb. 11, 2019 for European Patent EP2968301.

Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.

Rosenberg J., et al., "Novel Therapeutic Delivery System," Journal of Controlled Release, 2003, vol. 87, pp. 264-267.

Rossmann M.G., "The Molecular Replacement Method: A Collection of Papers on the Use of Non-Crystallographic Symmetry" Gordon and Breach Science Publishers, 1972, Table of Contents.

Sali A., et al., "Comparative Protein Modelling by Satisfaction of Spatial Restraints," Journal of Molecular Biology, 1993, vol. 234 (3), pp. 779-815.

Sato H., et al., "Prediction of Multiple Binding Modes of the CDK2 Inhibitors, Anilinopyrazoles, Using the Automated Docking Programs GOLD, FlexX, and LigandFit: An Evaluation of Performance," Journal of Chemical Information and Modeling, 2006, vol. 46 (6), pp. 2552-2562.

Sato M., et al., "Efficient Preparation of Optically Pure C2-Symmetrical Cyclic Amines for Chiral Auxiliary," Synthesis, 2004, vol. 9, pp. 1434-1438.

Sawyer J.S., et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.

(56) References Cited

OTHER PUBLICATIONS

Serajuddin A.T., "Solid Dispersion of Poorly Water-Soluble Drugs: Early Promises, Subsequent Problems, and Recent Breakthroughs," Journal of Pharmaceutical Sciences, 1999, vol. 88 (10), pp. 1058-1066.
Singh Y., et al., "Recent Trends in Targeted Anticancer Prodrug and Conjugate Design," Current Medical Chemistry, 2008, vol. 15 (18), pp. 1802-1826.
Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.
Smith D.C., et al., "Reissert Compound Chemistry. XXVI. The Syntheses of Bis-Benzylisoquinolines," Journal of Heterocyclic Chemistry, 1976, vol. 13, pp. 573-576.
Sousa S.F., et al., "Protein-Ligand Docking: Current Status and Future Challenges," Proteins, 2006, vol. 65 (1), pp. 15-26.
Sperling L. H., "Introduction to Physical Polymer Science," 2nd Edition, John Wiley & Sons, Inc., 1992, Table of Contents, 18 pages.
Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.
Suppiah V., et al., "IL28B is Associated with Response to Chronic Hepatitis C Interferon-Alpha and Ribavirin Therapy," Nature genetics, 2009, vol. 41(10), pp. 1100-1104.
Taburet A.M., and Singlas E., "Drug Interactions with Antiviral Drugs," Clinical Pharmacokinetics, 1996, vol. 30(5), pp. 385-401.
Takagi S., et al., "Antimicrobial Agents From Bletilla Striata," Phyrochemisrry, 1983, vol. 22 (4), pp. 1011-1015.
Tanaka Y., et al., "Genome-Wide Association of IL28B with Response to Pegylated Interferon-Alpha and Ribavirin Therapy for Chronic Hepatitis C," Nature Genetics, 2009, vol. 41(10), pp. 1105-1109.
Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28 (2), pp. 210-215.
Tellinghuisen T.L., et al., "Structure of the Zinc-Binding Domain of an Essential Component of the Hepatitis C Virus Replicase," Nature, 2005, vol. 435 (7040), pp. 374-379.
Testa B., et al., "Prodrug Research: Futile or Fertile?," Biochemical Pharmacology, 2004, vol. 68, pp. 2097-2106.
Thayer A. M., "Finding Solutions, Custom manufacturers take on drug solubility issues to help pharmaceutical firms move products through development," Chemical & Engineering News, 2010, vol. 88 (22), pp. 13-18.
Tripathi R.L., et al., "Replication Efficiency of Chimeric Replicon Containing NS5A-5B Genes Derived from HCV-infected Patient Sera," Antiviral Research, 2007, vol. 73 (1), pp. 40-49.
Vagin A., et al., "MOLREP: An Automated Program for Molecular Replacement," Journal of Applied Crystallography, 1997, vol. 30 (6), pp. 1022-1025.
Vallee R.J., et al., "Photoannelation Reactions of 3-(Alk-1-ynyl)cyclohept-2-en-1-ones," Helvetica Chimica Acta, 2010, vol. 93 (1), pp. 17-24.
Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.
Voigt R., "Pharmaceutical Technology" for Students and Professionals, 7th revised Edition, 2000, pp. 80-85.
Wagner R., et al., "Highlights of the Structure-Activity Relationships of Benzimidazole Linked Pyrrolidines Leading to the Discovery of the Hepatitis C Virus NSSA Inhibitor Pibrentasvir (ABT-530)," Journal of Medicinal Chemistry, May 10, 2018, vol. 61(9), pp. 4052-4066.
Warren G.L., et al., "A Critical Assessment of Docking Programs and Scoring Functions," Journal of Medicinal Chemistry, 2006, vol. 49 (20), pp. 5912-5931.
Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.
Wolfe J.P., et al., "Palladium-Catalyzed Amination of Aryl Triflates," Journal of Organic Chemistry, 1997, vol. 62 (5), pp. 1264-1267.
Written Opinion for Application No. PCT/US2012/026456, dated Aug. 25, 2013, 4 pages.
Wu G.Y., et al., "A Novel Immunocompetent Rat Model of HCV Infection and Hepatitis," Gastroenterology, 2005, vol. 128 (5), pp. 1416-1423.
Wu J.Z., et al., "Phosphorylation of Ribavirin and Viramidine by Adenosine Kinase and Cytosolic 5'-Nucleotidase II: Implications for Ribavirin Metabolism in Erythrocytes," Antimicrobial Agents and Chemotherapy, 2005, vol. 49(6), pp. 2164-2171.
Wyles D., et al., "Retreatment of Patients Who Failed Glecaprevir/Pibrentasvir Treatment for Hepatitis C Virus Infection," Journal of Hepatology, 2019, vol. 70 (5), pp. 1019-1023.
Xiao D., et al., "A Practical Synthetic Pathway to Polysubstituted Tetrahydropyridines via Multicomponent Reactions Catalyzed by BF3•OEt2," Synlett, 2005, vol. 10, pp. 1531-1534 .
Xie Z.C., et al., "Transmission of Hepatitis C Virus Infection to Tree Shrews," Virology, 1998, vol. 244 (2), pp. 513-520.
Yanagi M., et al., "Transcripts from a Single Full-Length cDNA Clone of Hepatitis C Virus are Infectious when Directly Transfected into the Liver of a Chimpanzee," Proceedings of the National Academy of Sciences, 1997, vol. 94 (16), pp. 8738-8743.
Yu H., et al., "The Discovery of Novel Vascular Endothelial Growth Factor Receptor Tyrosine Kinases Inhibitors: Pharmacophore Modeling, Virtual Screening and Docking Studies," Chemical Biology and Drug Design, 2007, vol. 69 (3), pp. 204-211.
Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Organic Letters, 2002, vol. 4 (23), pp. 4029-4032.
Zhu Q., et al., "Novel Robust Hepatitis C Virus Mouse Efficacy Model," Antimicrobial Agents and Chemotherapy, 2006, vol. 50 (10), pp. 3260-3268.
Zuckerman E., et al., "Management of Hepatitis C Virus-related Arthritis," BioDrugs, 2001, vol. 15 (9), pp. 573-584.
Goldberg D.S., et al., "Trial of Transplantation of HCV-Infected Kidneys into Uninfected Recipients," The New England Journal of Medicine, Jun. 2017, vol. 376 (24), pp. 2394-2395.
Hulskotte E.G et al., "Pharmacokinetic Interaction Between HCV Protease Inhibitor Boceprevir and Methadone or Buprenorphine in Subjects on Stable Maintenance Therapy," European Journal of Clinical Pharmacology, Mar. 2015, vol. 71(3), pp. 303-311.
Extended European Search Report for EP Application No. 20183791.1 dated Dec. 18, 2020.
Extended European Search Report for Patent Application No. 20167304.3, dated Sep. 28, 2020, 12 pages.
Lok A., S., et al., "Efficacy of Glecaprevir and Pibrentasvir in Patients with Genotype 1 Hepatitis C Virus Infection With Treatment Failure After NS5A Inhibitor Plus Sofosbuvir Therapy," Gastroenterology, Aug. 2019, vol. 157 (6), pp. 1506-1517.
Notice of Opposition for European Patent No. EP2897611 dated Apr. 24, 2020, 22 pages.
EASL Clinical Practice Guidelines: Management of Hepatitis C virus infection, Journal of Hepatology 2014 vol. 60, pp. 392-420.

* cited by examiner

METHODS FOR TREATING HCV

FIELD OF THE INVENTION

The present invention relates to interferon- and ribavirin-free treatment for hepatitis C virus (HCV).

BACKGROUND OF THE INVENTION

The HCV is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

Chronic HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often incomplete. Therefore, there is a need for new therapies to treat HCV infection.

BRIEF SUMMARY OF THE INVENTION

One aspect of the present invention features methods for treating HCV infection in a subject in need of such treatment. The methods comprise administering at least two direct acting antiviral agents (DAAs) to the subject for a duration of no more than 12 weeks, or for another duration as set forth herein. The at least two DAAs comprise Compound 1 (or a pharmaceutically acceptable salt thereof) and Compound 2 (or a pharmaceutically acceptable salt thereof); and the at least two DAAs can also additionally comprise one or more other DAAs, such as sofosbuvir or another HCV polymerase inhibitor. Preferably, the duration of the treatment is 12 weeks. The duration of the treatment can also last for less than 12 weeks; for example, the duration can last for 11, 10, 9, 8, 7, 6, 5 or 4 weeks, or no more than 8 weeks. Where three or more DAAs are used in the treatment regimen, the duration of the treatment preferably lasts for no more than 8 weeks; for example, the duration can last for 8, 7, 6, 5 or 4 weeks. Preferably, the two or more DAAs are administered in amounts effective to provide a sustained virological response (SVR) or achieve another desired measure of effectiveness in the subject. The subject is not administered either interferon or ribavirin during the treatment regimen. Put another way, the methods exclude the administration of interferon and ribavirin to the subject, thereby avoiding the side effects associated with interferon or ribavirin.

Another aspect of the present invention features methods for treating a population of subjects having HCV infection. The methods comprise administering at least two DAAs to the subjects for a duration of no more than 12 weeks, such as for a duration of 12, 11, 10, 9, 8, 7, 6, 5 or 4 weeks, or no more than 8 weeks. The at least two DAAs comprise Compound 1 (or a pharmaceutically acceptable salt thereof) and Compound 2 (or a pharmaceutically acceptable salt thereof); and the at least two DAAs can also additionally comprise one or more other DAAs, such as sofosbuvir or another HCV polymerase inhibitor. Preferably, the at least two DAAs are administered to the subjects in amounts effective to result in SVR or another measure of effectiveness in at least about 70% of the population, preferably at least about 80% of the population, or more preferably at least about 90% of the population.

In any method described herein, the at least two DAAs comprise (a) Compound 1 or a pharmaceutically acceptable salt thereof, and (b) Compound 2 or a pharmaceutically acceptable salt thereof. The at least two DAAs can also optionally comprise one or more other anti-HCV agents. These other optional anti-HCV agents can be selected from protease inhibitors, nucleoside or nucleotide polymerase inhibitors, non-nucleoside polymerase inhibitors, NS3B inhibitors, NS4A inhibitors, NS5A inhibitors, NS5B inhibitors, cyclophilin inhibitors, or combinations thereof. Non-limiting examples of the other optional antic-HCV agents include PSI-7977 (sofosbuvir), PSI-938, BMS-790052 (daclatasvir), BMS-650032 (asunaprevir), BMS-791325, GS-5885 (ledipasvir), GS-9451 (tegobuvir), GS-9190, GS-9256, BI-201335, BI-27127, telaprevir, VX-222, TMC-435 (simepravir), MK-5172, MK-7009 (vaniprevir), danoprevir, R7128 (mericitabine), and any combination thereof.

For example, the DAAs used in a method of the present invention can comprise or consist of (a) Compound 1 or a pharmaceutically acceptable salt thereof, and (b) Compound 2 or a pharmaceutically acceptable salt thereof. For another example, the DAAs used in a method of the present invention can comprise or consist of (a) Compound 1 or a pharmaceutically acceptable salt thereof, (b) Compound 2 or a pharmaceutically acceptable salt thereof, and (c) a HCV polymerase inhibitor, wherein said HCV polymerase inhibitor can be a nucleotide or nucleoside polymerase inhibitor or a non-nucleoside or non-nucleotide polymerase inhibitor. For yet another example, the DAAs used in a method of the present invention can comprise or consist of (a) Compound 1 or a pharmaceutically acceptable salt thereof, (b) Compound 2 or a pharmaceutically acceptable salt thereof, and (c) a nucleotide or nucleoside HCV polymerase inhibitor. For yet another example, the DAAs used in a method of the present invention can comprise or consist of (a) Compound 1 or a pharmaceutically acceptable salt thereof, (b) Compound 2 or a pharmaceutically acceptable salt thereof, and (c) sofosbuvir. For yet another example, the DAAs used in a method of the present invention can comprise or consist of (a) Compound 2 or a pharmaceutically acceptable salt thereof and (b) sofosbuvir.

In any method described herein, the DAAs can be administered in any effective dosing schemes and/or frequencies; for example, they can each be administered daily. Each DAA can be administered either separately or in combination, and each DAA can be administered once a day, twice a day, or three times a day. Preferably, Compound 1 (or a pharmaceutically acceptable salt thereof) and Compound 2 (or a pharmaceutically acceptable salt thereof) are administered once daily (QD).

Preferably, Compound 1 (or a pharmaceutically acceptable salt thereof) is administered from 100 mg to 600 mg once daily, and Compound 2 (or a pharmaceutically acceptable salt thereof) is administered from 50 to 500 mg once daily. More preferably, Compound 1 (or a pharmaceutically acceptable salt thereof) is administered from 200 mg to 600 mg once daily, and Compound 2 (or a pharmaceutically acceptable salt thereof) is administered from 100 to 500 mg once daily. Highly preferably, Compound 1 (or a pharmaceutically acceptable salt thereof) is administered from 400 mg to 600 mg once daily, and Compound 2 (or a pharmaceutically acceptable salt thereof) is administered from 100 to 500 mg once daily. It was unexpectedly found that 200-300 mg Compound 1 has comparable anti-HCV efficacy to 400 mg Compound 1. Therefore, more preferably, Compound 1 (or a pharmaceutically acceptable salt thereof) is administered from 200 mg to 300 mg once daily, and Compound 2 (or a pharmaceutically acceptable salt thereof) is administered from 100 to 500 mg once daily. For example, Compound 1 (or a pharmaceutically acceptable salt thereof) can be administered 200 mg once daily, and Compound 2 (or a pharmaceutically acceptable salt thereof) is administered 120 mg once daily. For another example, Compound 1 (or a pharmaceutically acceptable salt thereof) can be administered 300 mg once daily, and Compound 2 (or a pharmaceutically acceptable salt thereof) is administered 120 mg once daily. For yet another example, Compound 1 (or a pharmaceutically acceptable salt thereof) can be administered 400 mg once daily, and Compound 2 (or a pharmaceutically acceptable salt thereof) is administered 120 mg once daily. For another example, Compound 1 (or a pharmaceutically acceptable salt thereof) can be administered 400 mg once daily, and Compound 2 (or a pharmaceutically acceptable salt thereof) can be administered 240 mg once daily.

In yet another aspect, the present invention features a combination of Compound 1 (or a pharmaceutically acceptable salt thereof) and Compound 2 (or a pharmaceutically acceptable salt thereof) for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon or ribavirin (i.e., neither interferon nor ribavirin are administered). Compound 1 (or the salt thereof) and Compound 2 (or the salt thereof) can be administered concurrently or sequentially. Preferably, Compound 1 (or the salt thereof) and Compound 2 (or the salt thereof) can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. As used in this application, the interferon non-responder patients include partial interferon responders and interferon rebound patients. See GUIDANCE FOR INDUSTRY—CHRONIC HEPATITIS C VIRUS INFECTION: DEVELOPING DIRECT-ACTING ANTIVIRAL AGENTS FOR TREATMENT (FDA, September 2010, draft guidance) for the definitions of naïve, partial responder, responder relapser (i.e., rebound), and null responder patients. The interferon non-responder patients also include null responder patients. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 1 (or a pharmaceutically acceptable salt thereof), Compound 2 (or a pharmaceutically acceptable salt thereof), and an HCV polymerase inhibitor for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering either interferon or ribavirin, i.e., neither interferon nor ribavirin are administered. Compound 1 (or the salt thereof), Compound 2 (or the salt thereof) and the HCV polymerase inhibitor can be administered concurrently or sequentially. Preferably, Compound 1 (or the salt thereof), Compound 2 (or the salt thereof) and the HCV polymerase inhibitor can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 1 (or a pharmaceutically acceptable salt thereof), Compound 2 (or a pharmaceutically acceptable salt thereof), and sofosbuvir for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon. Compound 1 (or the salt thereof), Compound 2 (or the salt thereof) and sofosbuvir can be administered concurrently or sequentially. Preferably, Compound 1 (or the salt thereof), Compound 2 (or the salt thereof) and sofosbuvir can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

In yet another aspect, the present invention features a combination of Compound 2 (or a pharmaceutically acceptable salt thereof) and sofosbuvir for use to treat HCV infection. The treatment comprises administering the DAAs to a subject infected with HCV. The duration of the treatment regimen is no more than twelve weeks (e.g., the duration being 12 weeks; or the duration being 11, 10, 9, 8, 7, 6, 5, 4, or 3 weeks). Preferably, the duration of the treatment regimen is twelve weeks. The duration of the treatment can also last, for example, no more than eight weeks (e.g., the duration being 8 weeks; or the duration being 7, 6, 5, 4, or 3 weeks). The treatment does not include administering interferon. Compound 2 (or the salt thereof) and sofosbuvir can be administered concurrently or sequentially. Preferably, Compound 2 (or the salt thereof) and sofosbuvir can be administered once daily. As a non-limiting example, the patient being treated is infected with HCV genotype 1, such as genotype 1a or 1b. As another non-limiting example, the patient is infected with HCV genotype 2. As another non-limiting example, the patient is infected with HCV genotype 3. As another non-limiting example, the patient is infected with HCV genotype 4. As another non-limiting example, the patient is infected with HCV genotype 5. As another non-limiting example, the patient is infected with HCV genotype 6. As yet another non-limiting example, the patient is a HCV-treatment naïve patient, a HCV-treatment experienced patient, an interferon non-responder (e.g., a null responder), or not a candidate for interferon treatment. In one example of this aspect of the invention, the treatment lasts for 12 weeks, and the subject being treated is a naïve patient infected with HCV genotype 1. In another example, the treatment lasts for 11 weeks, and the subject being treated is a naïve patient infected with HCV genotype 1. In still another example, the treatment lasts for 10 weeks, and the subject being treated is a naïve patient infected with HCV genotype 1. In yet another example, the treatment lasts for 9 weeks, and the subject being treated is a naïve patient infected with HCV genotype 1. In yet another example, the treatment lasts for 8 weeks, and the subject being treated is a naïve patient infected with HCV genotype 1. In yet another example, the treatment lasts for 7 weeks, and the subject being treated is a naïve patient infected with HCV genotype 1. In yet another example, the treatment lasts for 6 weeks, and the subject being treated is a naïve patient infected with HCV genotype 1. In yet another example, the treatment lasts for 5 weeks, and the subject being treated is a naïve patient infected with HCV genotype 1. In yet another example, the treatment lasts for 4 weeks, and the subject being treated is a naïve patient infected with HCV genotype 1. In yet another example, the treatment lasts for 12 weeks, and the subject being treated is a naïve patient infected with HCV genotype 3. In another example, the treatment lasts for 11 weeks, and the subject being treated is a naïve patient infected with HCV genotype 3. In still another example, the treatment lasts for 10 weeks, and the subject being treated is a naïve patient infected with HCV genotype 3. In yet another example, the treatment lasts for 9 weeks, and the subject being treated is a naïve patient infected with HCV genotype 3. In yet another example, the treatment lasts for 8 weeks, and the subject being treated is a naïve patient infected with HCV genotype 3. In yet another example, the treatment lasts for 7 weeks, and the subject being treated is a naïve patient infected with HCV genotype 3. In yet another example, the treatment lasts for 6 weeks, and the subject being treated is a naïve patient infected with HCV genotype 3. In yet another example, the treatment lasts for 5 weeks, and the subject being treated is a naïve patient infected with HCV genotype 3. In yet another example, the treatment lasts for 4 weeks, and the subject being treated is a naïve patient infected with HCV genotype 3. In yet another example, the treatment lasts for 12 weeks, and the subject being treated is a non-responder (e.g., a null responder) infected with HCV genotype 1. In another example, the treatment lasts for 11 weeks, and the subject being treated is a non-responder (e.g., a null responder) infected with HCV genotype 1. In still another example, the treatment lasts for 10 weeks, and the subject being treated is a non-responder (e.g., a null responder) infected with HCV genotype 1. In yet another example, the treatment lasts for 9 weeks, and the subject being treated is a non-responder (e.g., a null responder) infected with HCV genotype 1. In yet another example, the treatment lasts for 8 weeks, and the subject being treated is a non-responder (e.g., a null responder) infected with HCV genotype 1. In yet another example, the treatment lasts for 7 weeks, and the subject being treated is a non-responder (e.g., a null responder) infected with HCV genotype 1. In yet another example, the treatment lasts for 6 weeks, and the subject being treated is a non-responder (e.g., a null responder) infected with HCV genotype 1. In yet another example, the treatment lasts for 5 weeks, and the subject being treated is a non-responder (e.g., a null responder) infected with HCV genotype 1. In yet another example, the treatment lasts for 4 weeks, and the subject being treated is a non-responder (e.g., a null responder) infected with HCV genotype 1. In yet another example, the treatment lasts for 12 weeks, and the subject being treated is a non-responder (e.g., a null responder) infected with HCV genotype 3. In another example, the treatment lasts for 11 weeks, and the subject being treated is a non-responder (e.g., a null responder) infected with HCV genotype 3. In still another example, the treatment lasts for 10 weeks, and the subject being treated is a non-responder (e.g., a null responder) infected with HCV genotype 3. In yet another example, the treatment lasts for 9 weeks, and the subject being treated is a non-responder (e.g., a null responder) infected with HCV genotype 3. In yet another example, the treatment lasts for 8 weeks, and the subject being treated is a non-responder (e.g., a null responder) infected with HCV genotype 3. In yet another example, the treatment lasts for 7 weeks, and the subject being treated is a non-responder (e.g., a null responder) infected with HCV genotype 3. In yet another example, the treatment lasts for 6 weeks, and the subject being treated is a non-responder (e.g., a null responder) infected with HCV genotype 3. In yet another example, the treatment lasts for 5 weeks, and the subject being treated is a non-responder (e.g., a null responder) infected with HCV genotype 3. In yet another example, the treatment lasts for 4 weeks, and the subject being treated is a non-responder (e.g., a null responder) infected with HCV genotype 3.

A treatment regimen of the present invention generally constitutes a complete treatment regimen, i.e., no subsequent interferon-containing regimen is intended. Thus, a treatment or use described herein generally does not include any subsequent interferon-containing or ribavirin-containing treatment.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description

BRIEF DESCRIPTION OF THE DRAWINGS

The drawings are provided for illustration, not limitation.

DETAILED DESCRIPTION OF THE INVENTION

Figure 1:
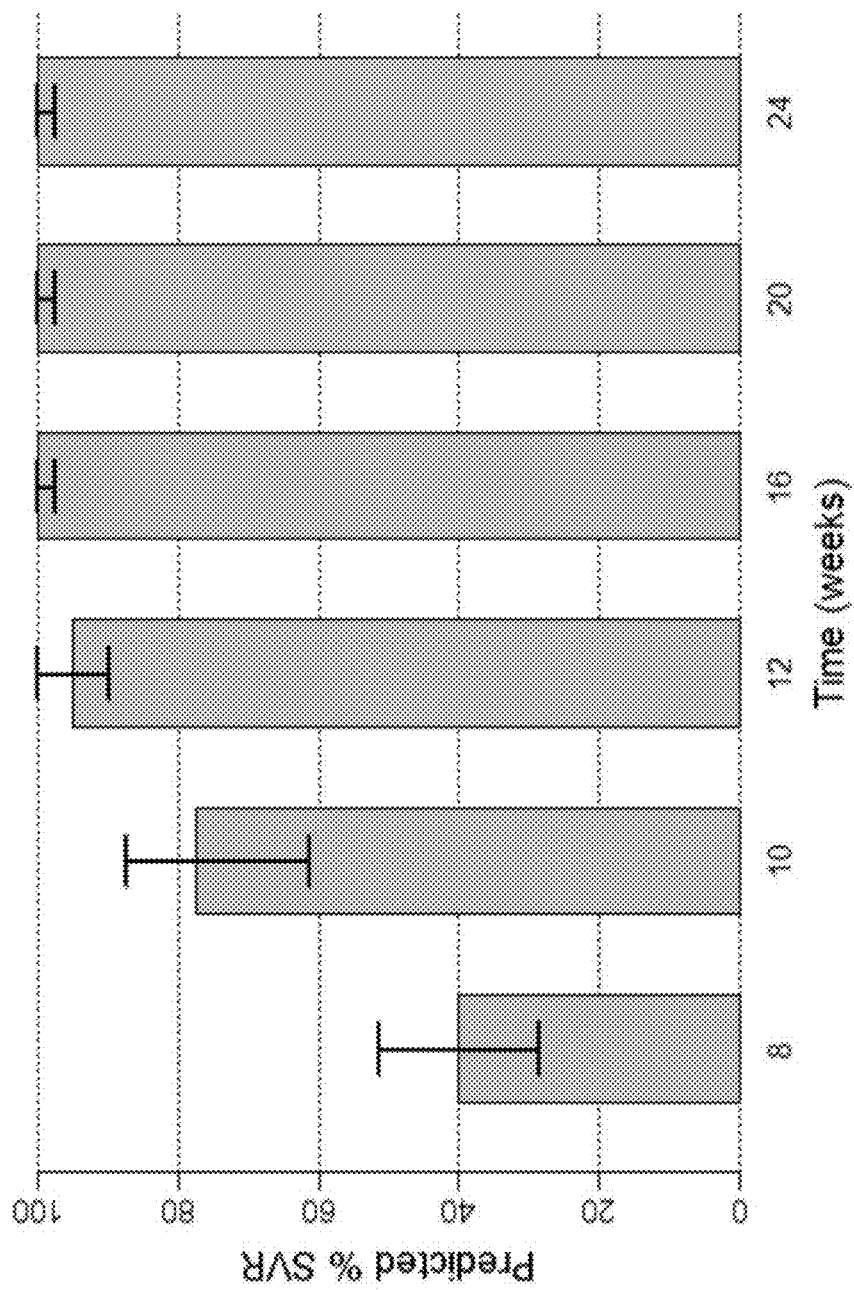
FIG. 1 shows the predicted median SVR percentages and 90% SVR confidence intervals for interferon/ribavirin-free, 2-DAA regimens comprising the use of Compound 1 (400 mg once daily) and Compound 2 (120 mg once daily) to treat genotype 1 naïve subjects.

The methods of the present invention include administering Compound 1 (or a pharmaceutically acceptable salt thereof) and Compound 2 (or a pharmaceutically acceptable salt thereof) to a subject in need thereof. Compound 1 has the following structure:

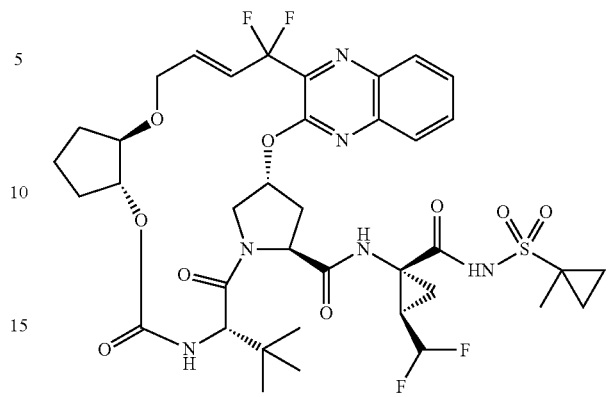

Compound 1

Compound 1 is a potent HCV protease inhibitor and is described in U.S. Patent Application Publication No. 2012/0070416.

Compound 2 has the following structure:

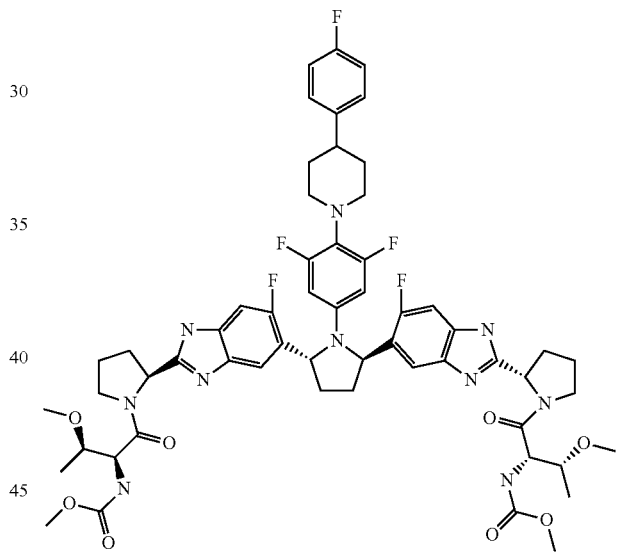

Compound 2

Compound 2 is a potent NS5A inhibitor and is described in U.S. Patent Application Publication No. 2012/0220562.

The interferon/ribavirin-based treatment may be physically demanding, and can lead to temporary disability in some cases. A substantial proportion of patients will experience a panoply of side effects ranging from a "flu-like" syndrome (the most common, experienced for a few days after the weekly injection of interferon) to severe adverse events including anemia, cardiovascular events and psychiatric problems such as suicide or suicidal ideation. The latter are exacerbated by the general physiological stress experienced by the patients. Ribavirin also has a number of side effects, including, anemia, high pill burden (e.g. 5-6 pills a day split BID) and teratogenicity restricting use in women of childbearing age.

The methods of the present invention provide effective treatment of HCV infection without the use of interferon or ribavirin and for a shorter period of time, for example and without limitation, a treatment duration of no more than twelve weeks, alternatively no more than eleven weeks, alternatively no more than ten weeks, alternatively no more than nine weeks, alternatively no more than eight weeks, alternatively no more than seven weeks, alternatively no more than six weeks, alternatively no more than five weeks, alternatively no more than four weeks, or alternatively, no more than three weeks.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e. neither interferon nor ribavirin are administered. The at least two DAAs comprise Compound 1 (or a pharmaceutically acceptable salt thereof) and Compound 2 (or a pharmaceutically acceptable salt thereof), which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 1 (or a pharmaceutically acceptable salt thereof), Compound 2 (or a pharmaceutically acceptable salt thereof) and an HCV polymerase inhibitor, which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 1 (or a pharmaceutically acceptable salt thereof), Compound 2 (or a pharmaceutically acceptable salt thereof) and sofosbuvir, which can be co-administered, or administered separately or independently, with the same or different dosing frequencies. Preferably, the at least two DAAs are administered once a day. They can also be administered, for example, twice a day or three times a day.

In one aspect, the present invention features methods for treating HCV infection in a subject comprising administering at least two DAAs, in the absence of interferon and ribavirin, to the subject for a duration of no more than twelve weeks, alternatively no more than eight weeks, such as for a duration of 12, 11, 10, 9, 8, 7, 6, 5, or 4 weeks. Put another way, the methods exclude interferon and ribavirin, i.e., neither interferon nor ribavirin are administered. The at least two DAAs comprise Compound 2 (or a pharmaceutically acceptable salt thereof) and sofosbuvir, which can be co-administered, or administered separately or independently, with the same or different dosing frequencies. Preferably, the at least two DAAs are administered once a day. They can also be administered, for example, twice a day or three times a day.

Various measures may be used to express the effectiveness of a method of the present invention. One such measure is SVR, which, as used herein, means that the virus is undetectable at the end of therapy and for at least 8 weeks after the end of therapy (SVR8); preferably, the virus is undetectable at the end of therapy and for at least 12 weeks after the end of therapy (SVR12); more preferably, the virus is undetectable at the end of therapy and for at least 16 weeks after the end of therapy (SVR16); and highly preferably, the virus is undetectable at the end of therapy and for at least 24 weeks after the end of therapy (SVR24). SVR24 is often considered as a functional definition of cure; and a high rate of SVR at less than 24 week post-treatment (e.g., SVR8 or SVR12) can be predictive of a high rate of SVR24.

Preferably, a method described herein achieves at least 70% SVR8. More preferably, a method described herein achieves at least 80% SVR8. Highly preferably, a method described herein achieves at least 90% SVR8. Most preferably, a method described herein achieves at least 95% SVR8.

Preferably, a method described herein achieves at least 70% SVR12. More preferably, a method described herein achieves at least 80% SVR12. Highly preferably, a method described herein achieves at least 90% SVR12. Most preferably, a method described herein achieves at least 95% SVR12. A method without achieving a significant SVR rate within patients is not considered an effective treatment, despite the fact that other effectiveness measures (e.g., RVR, eRVR, EVR, or ETR) may show suppression of the HCV virus during the treatment or immediately at the end of the treatment.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof) and Compound 2 (or a pharmaceutically acceptable salt thereof), and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof) and Compound 2 (or a pharmaceutically acceptable salt thereof), and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof), Compound 2 (or a pharmaceutically acceptable salt thereof) and an HCV polymerase inhibitor, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof), Compound 2 (or a pharmaceutically acceptable salt thereof) and an HCV polymerase inhibitor, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 1 (or a pharmaceutically acceptable salt thereof), Compound 2 (or a pharmaceutically acceptable salt thereof) and sofosbuvir, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 1 (or a pharmaceutically acceptable salt thereof), Compound 2 (or a pharmaceutically acceptable salt thereof) and sofosbuvir, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

In some embodiments, a treatment regimen of the invention comprises treating a population of subjects having HCV infection (e.g. treatment naïve subjects), and the regimen comprises administering at least two DAAs to the subjects for a duration of no more than 12 weeks, or for another duration disclosed herein (e.g., 11, 10, 9, 8, 7, 6, 5, or 4 weeks), wherein the at least two DAAs comprise Compound 2 (or a pharmaceutically acceptable salt thereof) and sofosbuvir, and are administered to the subjects in amounts effective to provide an SVR (e.g., SVR12 or SVR24) in at least about 70% of the population, alternatively at least about 75% of the population, alternatively at least about 80% of the population, alternatively at least about 85% of the population, alternatively at least about 90% of the population, alternatively at least about 95% of the population, alternatively about 100% of the population. In some embodiments, a treatment regimen of the invention comprises treating a population of IFN experienced subjects (e.g., interferon non-responders) having HCV infection, and the method comprises administering at least two DAAs to the subjects for a duration of no more than 12 weeks, or for another duration disclosed herein, wherein the at least two DAAs comprise Compound 2 (or a pharmaceutically acceptable salt thereof) and sofosbuvir, and are administered to the subjects in amounts effective to provide an SVR (e.g., SVR12 or SVR24) in at least about 50% of the population, alternatively at least about 55% of the population, alternatively at least about 60% of the population, alternatively at least about 65% of the population, alternatively at least about 70% of the population, alternatively at least about 75% of the population, alternatively at least about 80% of the population, alternatively at least about 85% of the population, alternatively at least about 90% of the population, alternatively at least about 95% of the population, or alternatively about 100% of the population.

It was unexpected that an interferon-free treatment using a combination of Compound 1 (or a pharmaceutically acceptable salt thereof) and Compound 2 (or a pharmaceutically acceptable salt thereof), in the absence of interferon and ribavirin, and for a duration of no more than 12 weeks, can achieve significant SVR.

Accordingly, in one aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

As used in this application, an HCV polymerase inhibitor can be a nucleoside polymerase inhibitor, a nucleotide polymerase inhibitor, a non-nucleoside polymerase inhibitor, or a non-nucleotide polymerase inhibitor.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof) and Compound 2 (or a pharmaceutically acceptable salt thereof). The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof) and Compound 2 (or a salt thereof), said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and an HCV polymerase inhibitor. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and the HCV polymerase inhibitor, said at least two DAAs can also include one or more additional DAAs selected from, for example, HCV protease inhibitors, HCV polymerase inhibitors, or HCV NS5A inhibitors. Non-limiting examples of such additional DAAs include PSI-7977, PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b;

or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 1 (or a pharmaceutically acceptable salt thereof), Compound 2 (or a pharmaceutically acceptable salt thereof) and sofosbuvir. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 1 (or a salt thereof), Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 8 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 7 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 6 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 5 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 4 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 3 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 24 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 13 to 23 weeks (e.g., the duration of the treatment is selected from 13, 14, 15, 16, 17, 18, 19, 20, 21, 22 or 23 weeks) and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 12 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 11 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 10 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In yet another aspect, the present invention features a method of treating HCV infection, comprising administering to a patient in need thereof an effective amount of a combination of at least two DAAs, wherein said at least two DAAs comprise Compound 2 (or a pharmaceutically acceptable salt thereof) and sofosbuvir. The treatment lasts 9 weeks and does not include administration of any interferon or ribavirin (i.e., neither interferon nor ribavirin are administered). The DAAs can be administered at the same or different dosing frequencies. The patient being treated can be a treatment naïve patient; a treatment experienced patient, including, but not limited to, a relapser, an interferon partial responder, an interferon non-responder, or a null responder; or a patient unable to take interferon. The patient may be infected with, for example and without limitation, HCV genotype 1, such as HCV genotype 1a or HCV genotype 1b; or HCV genotype 2 or 3; or HCV genotype 4, 5 or 6. The treatment according to this aspect of the technology may also be effective against other HCV genotypes. The DAAs can be administered around the same time or at different times. In addition to Compound 2 (or a salt thereof) and sofosbuvir, said at least two DAAs can also include one or more additional DAAs selected from, for example, HCV protease inhibitors, HCV polymerase inhibitors, or HCV NS5A inhibitors. Non-limiting examples of such additional DAAs include PSI-938, TMC-435, BMS-790052, BMS-650032, GS-5885, GS-9190, GS-9451, BI-201335, BI-207127, telaprevir, VX-222, mericitabine, and danoprevir.

In each aspect, embodiment, example or method described herein, Compound 1 (or a pharmaceutically acceptable salt thereof) can be administered, for example and without limitation, from 100 mg to 600 mg once daily, and Compound 2 (or a pharmaceutically acceptable salt thereof) can be administered, for example and without limitation, from 50 to 500 mg once daily. More preferably, Compound 1 (or a pharmaceutically acceptable salt thereof) is administered from 200 mg to 600 mg once daily, and Compound 2 (or a pharmaceutically acceptable salt thereof) is administered from 100 to 500 mg once daily. Highly preferably, Compound 1 (or a pharmaceutically acceptable salt thereof) is administered from 400 mg to 600 mg once daily, and Compound 2 (or a pharmaceutically acceptable salt thereof) is administered from 100 to 500 mg once daily. Most preferably, Compound 1 (or a pharmaceutically acceptable salt thereof) is administered from 200 mg to 300 mg once daily, and Compound 2 (or a pharmaceutically acceptable salt thereof) is administered from 100 to 500 mg once daily. Preferably, Compound 1 (or a pharmaceutically acceptable salt thereof) can be administered 200 mg once daily, and Compound 2 (or a pharmaceutically acceptable salt thereof) is administered 120 mg once daily. Also preferably, Compound 1 (or a pharmaceutically acceptable salt thereof) can be administered 300 mg once daily, and Compound 2 (or a pharmaceutically acceptable salt thereof) is administered 120 mg once daily. For another example, Compound 1 (or a pharmaceutically acceptable salt thereof) can be administered 400 mg once daily, and Compound 2 (or a pharmaceutically acceptable salt thereof) is administered 120 mg once daily. For yet another example, Compound 1 (or a pharmaceutically acceptable salt thereof) can be administered 400 mg once daily, and Compound 2 (or a pharmaceutically acceptable salt thereof) can be administered 240 mg once daily.

In each aspect, embodiment, example or method described herein, sofosbuvir can be administered, for example and without limitation, 400 mg once daily.

A method of the present invention can be used to treat a naïve patient or a treatment experienced patient. Treatment experienced patients include interferon non-responders (e.g., null responders), partial responders, and relapsers. A method of the present invention can also be used to treat patients who are not candidates for interferon treatment. Patients who are not candidates for interferon treatment include, but are not limited to, one or more of the following groups: patients intolerant to interferon, patients who refuse to take interferon treatment, patients with medical conditions which preclude them from taking interferon, and patients who have an increased risk of side effects or infection by taking interferon.

In any method described herein wherein Compound 1 and Compound 2 are used, one or more additional DAAs can be optionally used in the treatment regimen in addition to Compound 1 (or a salt thereof) and Compound 2 (or a salt thereof). Similarly, in any method described herein wherein Compound 1, Compound 2 and sofosbuvir are used, one or more additional DAAs can be optionally used in the treatment regimen in addition to Compound 1 (or a salt thereof), Compound 2 (or a salt thereof) and sofosbuvir. Likewise, in any method described herein wherein Compound 2 and sofosbuvir are used, one or more additional DAAs can be optionally used in the treatment regimen in addition to Compound 2 (or a salt thereof) and sofosbuvir. These additional DAAs can be HCV protease inhibitors, HCV nucleoside or nucleotide polymerase inhibitors, HCV non-nucleoside polymerase inhibitors, HCV NS3B inhibitors, HCV NS4A inhibitors, HCV NS5A inhibitors, HCV NS5B inhibitors, HCV entry inhibitors, cyclophilin inhibitors, or combinations thereof.

Preferred HCV protease inhibitors for this purpose include, but are not limited to, telaprevir (Vertex), boceprevir (Merck), BI-201335 (Boehringer Ingelheim), GS-9451 (Gilead), and BMS-650032 (BMS). Other suitable protease inhibitors include, but are not limited to, ACH-1095 (Achillion), ACH-1625 (Achillion), ACH-2684 (Achillion), AVL-181 (Avila), AVL-192 (Avila), BMS-650032 (BMS), danoprevir (RG7227/ITMN-191, Roche), GS-9132 (Gilead), GS-9256 (Gilead), IDX-136 (Idenix), IDX-316 (Idenix), IDX-320 (Idenix), MK-5172 (Merck), narlaprevir (Schering-Plough Corp), PHX-1766 (Phenomix), TMC-435 (Tibotec), vanyprevir (MK-7009, Merck), VBY708 (Virobay), VX-500 (Vertex), VX-813 (Vertex), VX-985 (Vertex), or a combination thereof.

Preferred non-nucleoside HCV polymerase inhibitors for use in the present invention include, but are not limited to, GS-9190 (Gilead), BI-207127 (Boehringer Ingelheim), and VX-222 (VCH-222) (Vertex & ViraChem). Preferred nucleotide HCV polymerase inhibitors include, but are not limited to, PSI-7977 (Gilead), and PSI-938 (Gilead). Other suitable and non-limiting examples of suitable HCV polymerase inhibitors include ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-759 (Vertex), GS-6620 (Gilead), IDX-102 (Idenix), IDX-184 (Idenix), INX-189 (Inhibitex), MK-0608 (Merck), RG7128 (Roche), TMC64912 (Medivir), GSK625433 (GlaxoSmithKline), BCX-4678 (BioCryst), ALS-2200 (Alios BioPharma/Vertex), ALS-2158 (Alios BioPharma/Vertex), or a combination thereof. A polymerase inhibitor may be a nucleoside or nucleotide polymerase inhibitor, such as GS-6620 (Gilead), IDX-102 (Idenix), IDX-184 (Idenix), INX-189 (Inhibitex), MK-0608 (Merck), PSI-7977 (Gilead), PSI-938 (Gilead), RG7128 (Roche), TMC64912 (Medivir), ALS-2200 (Alios BioPharma/Vertex), ALS-2158 (Alios BioPharma/Vertex), or a combination therefore. A polymerase inhibitor may also be a non-nucleoside polymerase inhibitor, such as PF-00868554 (Pfizer), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir (Gilead), TMC-647055 (Tibotec), VCH-759 (Vertex & ViraChem), VCH-916 (ViraChem), VX-222 (VCH-222) (Vertex & ViraChem), VX-759 (Vertex), or a combination thereof.

Preferred NS5A inhibitors include, but are not limited to, BMS-790052 (BMS) and GS-5885 (Gilead). Non-limiting examples of suitable NS5A inhibitors include GSK62336805 (GlaxoSmithKline), ACH-2928 (Achillion), AZD2836 (Astra-Zeneca), AZD7295 (Astra-Zeneca), BMS-790052 (BMS), BMS-824393 (BMS), GS-5885 (Gilead), PPI-1301 (Presidio), PPI-461 (Presidio) A-831 (Arrow Therapeutics), A-689 (Arrow Therapeutics) or a combination thereof.

Non-limiting examples of suitable cyclophilin inhibitors include alisporovir (Novartis & Debiopharm), NM-811 (Novartis), SCY-635 (Scynexis), or a combination thereof.

Non-limiting examples of suitable HCV entry inhibitors include ITX-4520 (iTherx), ITX-5061 (iTherx), or a combination thereof.

Specific examples of other DAA agents that are suitable for inclusion in a method of the present invention include, but are not limited to, AP-H005, A-831 (Arrow Therapeutics) (NS5A inhibitor), A-689 (Arrow Therapeutics) (NS5A inhibitor), INX08189 (Inhibitex) (polymerase inhibitor), ITMN-191 (Intermune/Roche) (NS3/4A Protease inhibitor), VBY-376 (Protease Inhibitor) (Virobay), ACH-1625 (Achillion, Protease inhibitor), IDX136 (Idenix, Protease Inhibitor), IDX316 (Idenix, Protease inhibitor), VX-813 (Vertex), SCH 900518 (Schering-Plough), TMC-435 (Tibotec), ITMN-191 (Intermune, Roche), MK-7009 (Merck), IDX-PI (Novartis), R7128 (Roche), PF-868554 (Pfizer) (non-nucleoside polymerase inhibitor), PF-4878691 (Pfizer), IDX-184 (Idenix), IDX-375 (Idenix, NS5B polymerase inhibitor), PPI-461 (Presidio), BILB-1941 (Boehringer Ingelheim), GS-9190 (Gilead), BMS-790052 (BMS), CTS-1027 (Conatus), GS-9620 (Gilead), PF-4878691 (Pfizer), R05303253 (Roche), ALS-2200 (Alios BioPharma/Vertex), ALS-2158 (Alios BioPharma/Vertex), GSK62336805 (GlaxoSmithKline), or any combinations thereof.

The chemical structures of some of these optional HCV inhibitors are provided below:

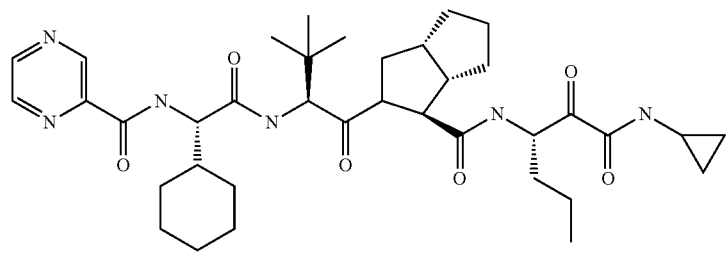
Telaprevir
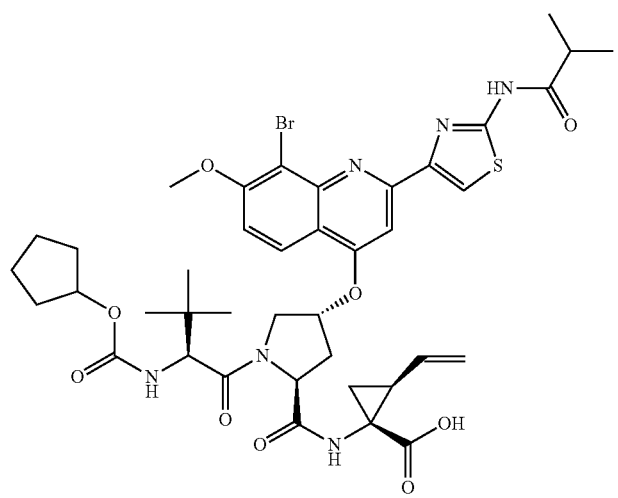
BI-201335
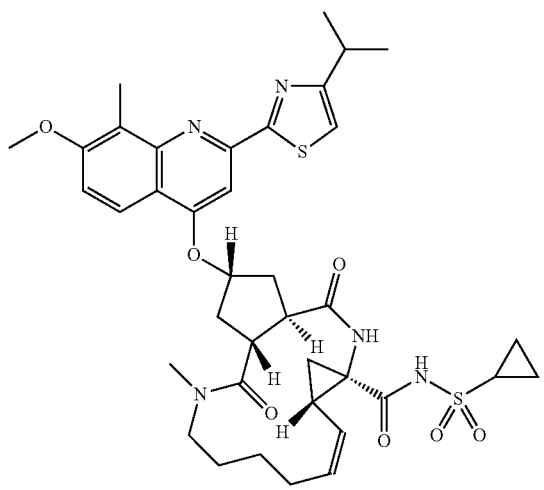
TMC-435 (TMC-435350)
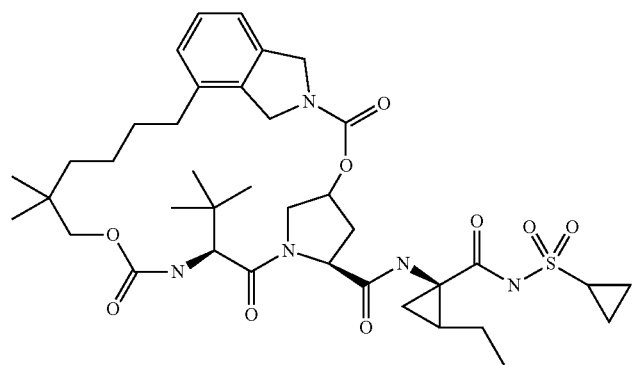
Vaniprevir, MK-7009

-continued
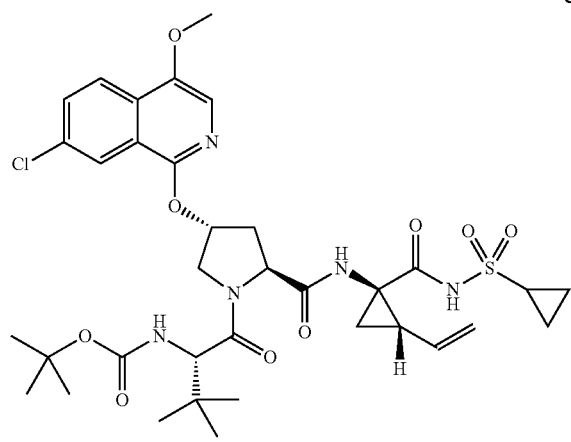
BMS-650032 (Asunaprevir)
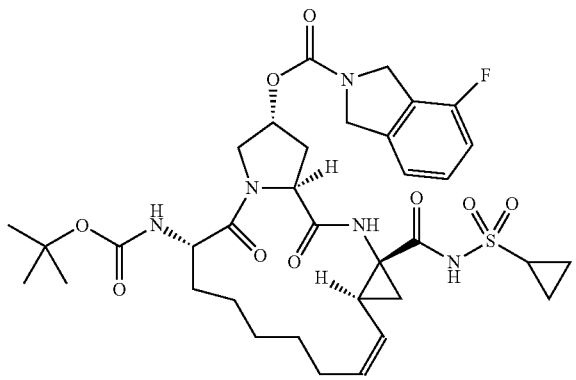
danoprevir
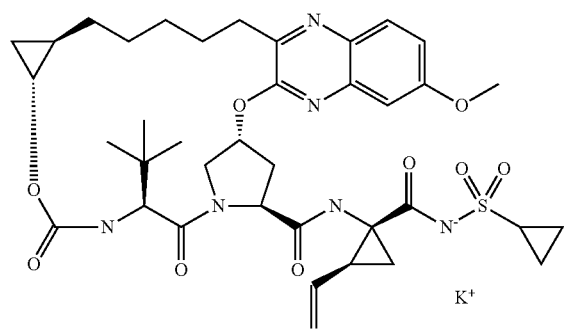
MK-5172
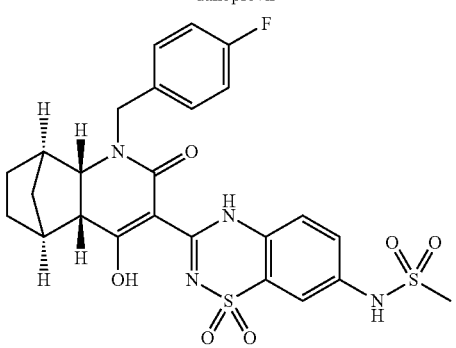
ANA-598 (Setrobuvir)
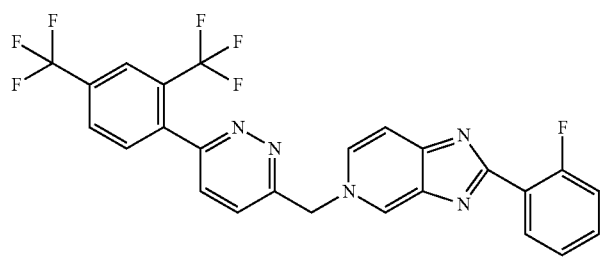
GS-333126 (GS-9190 or tegobuvir)
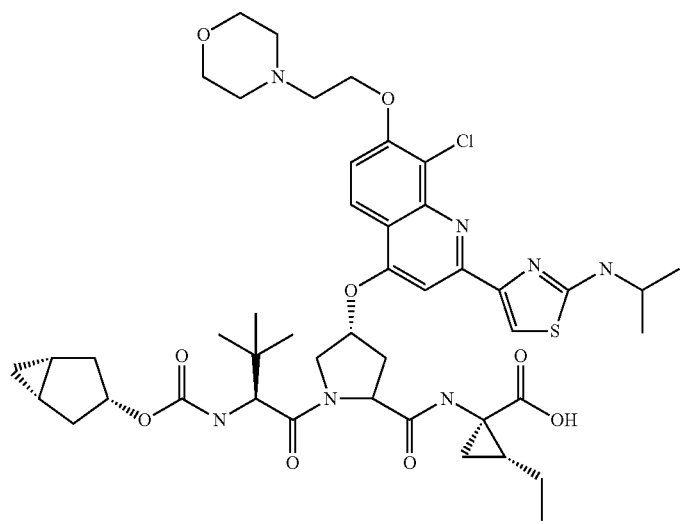
GS-9451

-continued
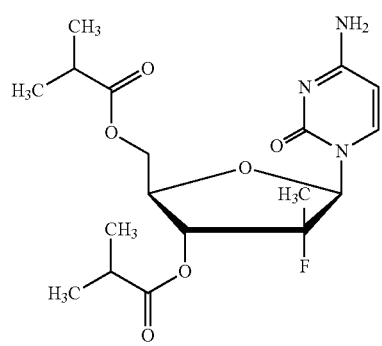
Mericitabine (R-4048 or RG7128)
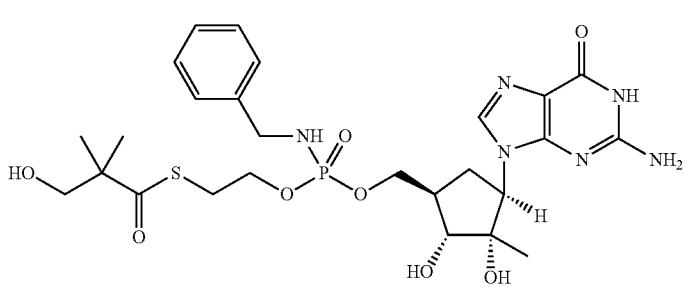
IDX-184
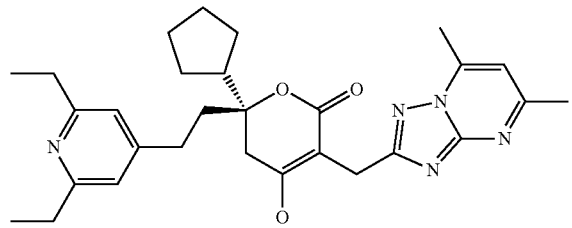
filibuvir (PF-00868554)
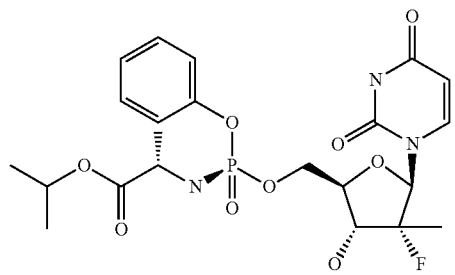
PSI-7977
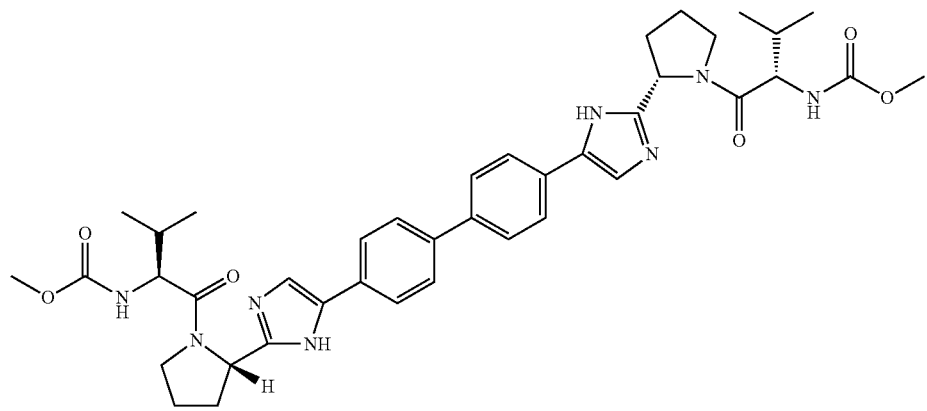
BMS-790052 (daclatasvir)
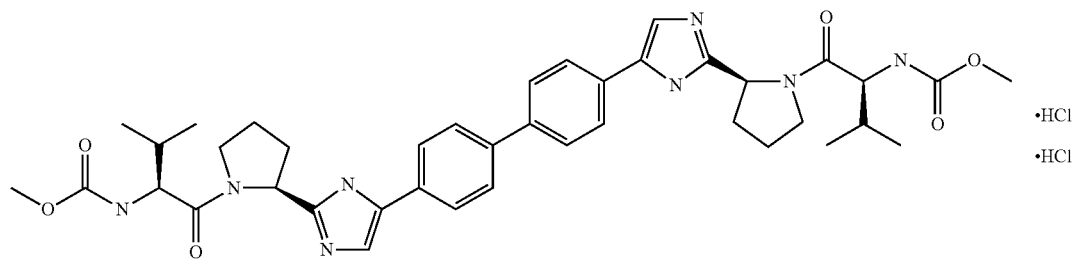
Daclatasvir dihydrochloride -continued

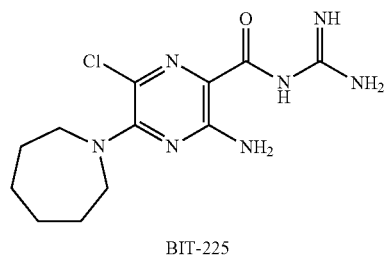
BIT-225

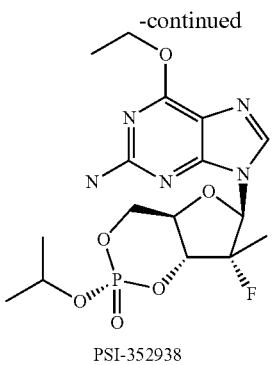
PSI-352938

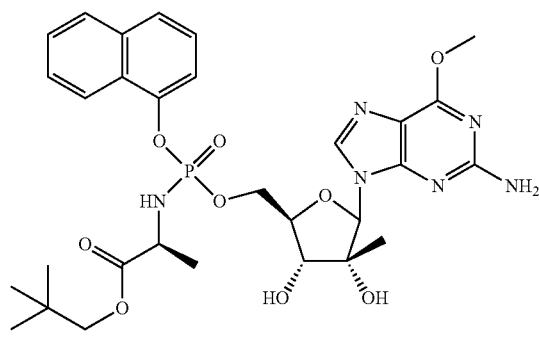
INX-189

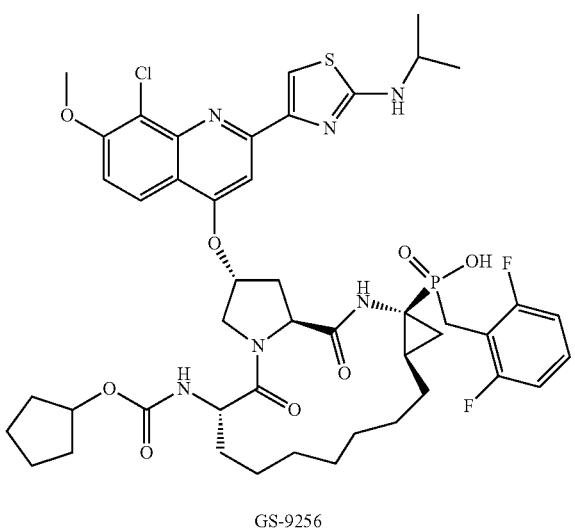
GS-9256

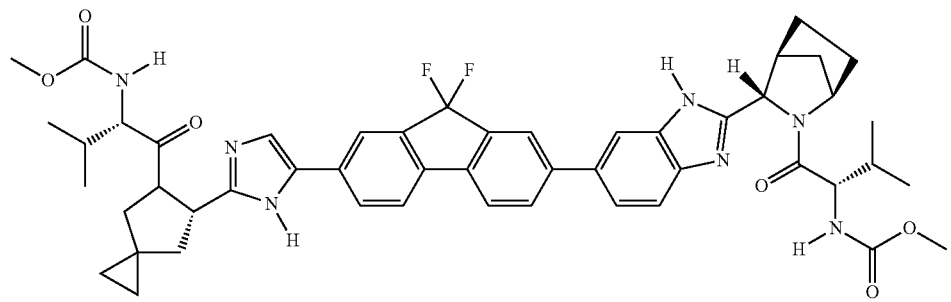
GS-5885

Any HCV inhibitor or DAA described herein encompasses its suitable salt forms when it is used in therapeutic treatments or pharmaceutical formulations.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof) and Compound 2 (a pharmaceutically acceptable salt thereof). Compound 1 (or a pharmaceutically acceptable salt thereof) and Compound 2 (a pharmaceutically acceptable salt thereof) can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin (i.e., neither interferon nor ribavirin are administered), and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and an HCV polymerase inhibitor. Compound 1 (or a pharmaceutically acceptable salt thereof), Compound 2 (a pharmaceutically acceptable salt thereof) and the HCV polymerase inhibitor can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 1 (or a pharmaceutically acceptable salt thereof), Compound 2 (a pharmaceutically acceptable salt thereof) and sofosbuvir. Compound 1 (or a pharmaceutically acceptable salt thereof), Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients infected with HCV genotype 1, such as 1a or 1b. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 or 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 2 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 3 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 4 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 5 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

In some embodiments, the present invention features methods for treating patients with HCV genotype 6 infection. The methods comprise administering to such a patient a combination of at least 2 DAAs for no more than 12 weeks (e.g., the duration being 12, 11, 10, 9, 8, 7, 6, 5, or 4 weeks), such as no more than 8 weeks (e.g., the duration being 8, 7, 6, 5, or 4 weeks), wherein the treatment does not include administration of either interferon or ribavirin, and said at least 2 DAAs comprise Compound 2 (a pharmaceutically acceptable salt thereof) and sofosbuvir. Compound 2 (a pharmaceutically acceptable salt thereof) and sofosbuvir can be administered in therapeutically effective amounts to provide a SVR (for example, at least 75% SVR8, or preferably at least 80% SVR8, or highly preferably at least 90% SVR8, or most preferably at least 95% SVR8) after the completion of the treatment. The patients may be treatment naïve patients or treatment experienced patients. The treatment duration can be no more than 12 weeks, including but not limited to, no more than 11 weeks, no more than 10 weeks, no more than 9 weeks, but preferably no more than 8 weeks, no more than 7 weeks, no more than 6 weeks, no more than 5 weeks, no more than 4 weeks, or no more than 3 weeks, e.g., the duration being 12 weeks, or the duration being 11 weeks, or the duration being 10 weeks, or the duration being 9 weeks, or the duration being 8 weeks, or the duration being 7 weeks, or the duration being 6 weeks, or the duration being 5 weeks, or the duration being 4 weeks.

It will be understood that the specific dose level for any particular patient will depend upon a variety of factors including the activity of the specific compound employed, the age, body weight, general health, sex, diet, time of administration, route of administration, rate of excretion, drug combination, and the severity of the disease undergoing therapy.

In any method described herein wherein Compound 1 and Compound 2 are used, Compound 1 (or a pharmaceutically acceptable salt thereof) and Compound 2 (a pharmaceutically acceptable salt thereof) may be co-formulated in a single dosage form. Non-limiting examples of suitable dosage forms include liquid or solid dosage forms. Preferably, Compound 1 and Compound 2 are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form). More preferably, each of the two DAAs is in an amorphous form, or highly preferably molecularly dispersed, in a matrix which comprises a pharmaceutically acceptable water-soluble polymer and a pharmaceutically acceptable surfactant.

In any method described herein wherein Compound 1, Compound 2 and sofosbuvir are used, Compound 1 (or a pharmaceutically acceptable salt thereof), Compound 2 (a pharmaceutically acceptable salt thereof) and sofosbuvir may be co-formulated in a single dosage form. Non-limiting examples of suitable dosage forms include liquid or solid dosage forms. Preferably, Compound 1, Compound 2 and sofosbuvir are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form).

In any method described herein wherein Compound 2 and sofosbuvir are used, Compound 2 (or a pharmaceutically acceptable salt thereof) and sofosbuvir may be co-formulated in a single dosage form. Non-limiting examples of suitable dosage forms include liquid or solid dosage forms. Preferably, Compound 2 and sofosbuvir are formulated in a single solid dosage form in which at least one of the DAAs is in an amorphous form, or highly preferably molecularly dispersed, in a matrix which comprises a pharmaceutically acceptable water-soluble polymer and a pharmaceutically acceptable surfactant. The other DAAs can also be in an amorphous form or molecularly dispersed in the matrix, or formulated in different form(s) (e.g., in a crystalline form).

In any method described herein, the patient being treated can be a treatment-naïve patient.

In any method described herein, the patient being treated can be an interferon non-responder.

In any method described herein, the patient being treated can be an interferon null-responder.

In any method described herein, the patient being treated can be without cirrhosis.

In any method described herein, the patient being treated can be a cirrhotic patient.

In any method described herein, the patient being treated can be a patient with compensated cirrhosis.

In any method described herein where Compound 1 and Compound 2 are used, the DAAs employed in the method can consist of Compound 1 and Compound 2. In any method described herein where Compound 1 and Compound 2 are used, the DAAs employed in the method can consist of Compound 1 and Compound 2. In any method described herein where Compound 1 and Compound 2 are used, the DAAs employed in the method can consist of Compound 1 (or a pharmaceutically acceptable salt thereof) and Compound 2 (or a pharmaceutically acceptable salt thereof). In any method described herein where Compound 1 and Compound 2 are used, the DAAs employed in the method can consist of Compound 1 (or a pharmaceutically acceptable salt thereof), Compound 2 (or a pharmaceutically acceptable salt thereof) and a HCV nucleotide polymerase inhibitor. In any method described herein where Compound 1 and Compound 2 are used, the DAAs employed in the method can consist of Compound 1, Compound 2 and a HCV nucleotide polymerase inhibitor. In any method described herein where Compound 1 and Compound 2 are used, the DAAs employed in the method can consist of Compound 1 and Compound 2. In any method described herein where Compound 1 and Compound 2 are used, Compound 1 and Compound 2 can be administered with food. In any method described herein where Compound 1 and Compound 2 are used, Compound 1 and Compound 2 can be administered without food.

In any method described herein, the patient can have renal impairment, include hemodialysis. In any method described herein, the patient can have chronic kidney disease (CKD) stage 3b (eGFR 30 to <45 mL/min/1.73 m$^2$), stage 4 (eGFR 15 to <30 mL/min/1.73 m$^2$) or stage 5 (eGFR<15 mL/min/1.73 m$^2$ or dialysis-dependent). In any method described herein, the patient can have HIV co-infection.

It is also contemplated a method of treating HCV, said method comprising administering to a patient in need thereof an effective amount of a combination of two or more DAAs. The treatment lasts 4 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 is (2R,6S,13aS,14aR,16aS,Z)—N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14-carboxamide, and Compound 4 is as dimethyl (2S,2'S)-1,1'-((2S,2'S)-2,2'-(4,4'-((2S,5 S)-1-(4-tert-butylphenyl)pyrrolidine-2,5-diyl)bis(4,1-phenylene))bis(azanediyl)bis(oxomethylene)bis(pyrrolidine-2,1-diyl)bis(3-methyl-1-oxobutane-2,1-diyl)dicarbamate, both of which are described in U.S. Patent Application Publication No. 2013/0102526, filed Oct. 19, 2012 and entitled "Methods for Treating HCV", which is incorporated herein by reference in its entirety. Compound 3 preferably is co-administered with ritonavir. More preferably, Compound 3 is co-formulated with ritonavir. It is believed that the combination of Compound 3, Compound 4, and sofosbuvir, without ribavirin and interferon, can achieve at least about 80% SVR rate against HCV genotype 1 after 4-week treatment. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 5 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. It is believed that the combination of Compound 3, Compound 4, and sofosbuvir, without ribavirin and interferon, can achieve at least about 80% SVR rate against HCV genotype 1 after 5-week treatment. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 6 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 7 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 8 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 9 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 10 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 11 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

It is further contemplated a method of treating HCV, said method comprising administering to a patient in need thereof an effective amount of a combination of two or more DAAs. The treatment lasts 12 weeks and does not include administration of any interferon or ribavirin (i.e., interferon- and ribavirin-free). The DAAs can be administered at the same or different dosing frequency. The patient being treated can be a treatment naïve patient, a treatment experienced patient, including, but not limited to, a relapser, an interferon partial responder, an interferon non-responder (e.g., a null responder), or a patient unable to take interferon. The patient can be infected with, for example and without limitation, HCV genotype 1, such as HCV genotype 1a or HCV genotype 1b; or HCV genotype 2 or 3. The treatment according to this aspect can also be effective against other HCV genotypes. The DAAs can be administered around the same time or at different times, and can be co-formulated in a single formulation or formulated in different compositions. Each DAA can be selected from HCV protease inhibitors, HCV polymerase inhibitors, or HCV NS5A inhibitors. For instance, the combination of two or more DAAs can be a combination of at least one HCV protease inhibitor and at least one HCV polymerase inhibitor (e.g., a combination of at least one HCV protease inhibitor and at least one non-nucleoside polymerase inhibitor, or a combination of at least one HCV protease inhibitor and at least one nucleoside or nucleotide polymerase inhibitor, or a combination of at least one HCV protease inhibitor, at least one nucleoside or nucleotide polymerase inhibitor and at least one non-nucleoside inhibitor). For another instance, the combination of two or more DAAs can be a combination of at least one HCV protease inhibitor and at least one HCV NS5A inhibitor. For still another instance, the combination of two or more DAAs can be a combination of at least one HCV protease inhibitor, at least one HCV polymerase inhibitor, and at least one HCV NS5A inhibitor. For another instance, the combination of two or more DAAs can be a combination of at least two HCV polymerase inhibitors (e.g., a combination of at least two nucleoside or nucleotide polymerase inhibitors, or a combination of at least one nucleoside or nucleotide polymerase inhibitor and at least one non-nucleoside polymerase inhibitor, or a combination of at least two non-nucleoside polymerase inhibitors). For another instance, the combination of two or more DAAs can be a combination of at least two HCV protease inhibitors. For another instance, the combination of two or more DAAs can be a combination of at least two HCV NS5A inhibitors. For another instance, the combination of two or more DAAs can be a combination of at least one HCV polymerase inhibitor and at least one NS5A inhibitor (e.g., a combination of at least one HCV NS5A inhibitor and at least one non-nucleoside polymerase inhibitor, or a combination of at least one HCV NS5A inhibitor and at least one nucleoside or nucleotide polymerase inhibitor, or a combination of at least one HCV NS5A inhibitor, at least one nucleoside or nucleotide polymerase inhibitor and at least one non-nucleoside polymerase inhibitor). In one example, the combination of two or more DAAs is a combination of Compound 3, Compound 4, and sofosbuvir. Compound 3 preferably is co-administered with ritonavir. More preferably, Compound 3 is co-formulated with ritonavir. In another example, the combination of two or more DAAs is a combination of Compound 3, Compound 4, and sofosbuvir; and the patient is infected with HCV genotype 1. In another example, the combination of two or more DAAs is a combination of Compound 3, Compound 4, and sofosbuvir; and the patient is a treatment-naïve patient infected with HCV genotype 1. In another example, the combination of two or more DAAs is a combination of Compound 3, Compound 4, and sofosbuvir; and the patient is an interferon non-responder infected with HCV genotype 1. In another example, the combination of two or more DAAs is a combination of sofosbuvir, an HCV NS5A inhibitor, and another HCV polymerase inhibitor. In another example, the combination of two or more DAAs is a combination of sofosbuvir, an HCV NS5A inhibitor, and another HCV polymerase inhibitor; and the patient is infected with HCV genotype 1. In another example, the combination of two or more DAAs is a combination of sofosbuvir, an HCV NS5A inhibitor, and another HCV polymerase inhibitor; and the patient is a treatment-naïve patient infected with HCV genotype 1. In another example, the combination of two or more DAAs is a combination of sofosbuvir, an HCV NS5A inhibitor, and another HCV polymerase inhibitor; and the patient is an interferon non-responder infected with HCV genotype 1. In yet another example, the combination of two or more DAAs comprises sofosbuvir, an HCV NS5A inhibitor, and an HCV protease inhibitor. In yet another example, the combination of two or more DAAs comprises sofosbuvir, an HCV NS5A inhibitor, and an HCV protease inhibitor; and the patient is infected with HCV genotype 1. In yet another example, the combination of two or more DAAs comprises sofosbuvir, an HCV NS5A inhibitor, and an HCV protease inhibitor; and the patient is a treatment-naïve patient infected with HCV genotype 1. In yet another example, the combination of two or more DAAs comprises sofosbuvir, an HCV NS5A inhibitor, and an HCV protease inhibitor; and the patient is an interferon non-responder infected with HCV genotype 1. In yet another example, the combination of two or more DAAs comprises sofosbuvir, an HCV protease inhibitor, and another HCV polymerase inhibitor. In yet another example, the combination of two or more DAAs comprises sofosbuvir, an HCV protease inhibitor, and another HCV polymerase inhibitor; and the patient is infected with HCV genotype 1. In yet another example, the combination of two or more DAAs comprises sofosbuvir, an HCV protease inhibitor, and another HCV polymerase inhibitor; and the patient is a treatment-naïve patient infected with HCV genotype 1. In yet another example, the combination of two or more DAAs comprises sofosbuvir, an HCV protease inhibitor, and another HCV polymerase inhibitor; and the patient is an interferon non-responder infected with HCV genotype 1. In another example, the combination of two or more DAAs is a combination of IDX21437, an HCV NS5A inhibitor, and another HCV polymerase inhibitor. In another example, the combination of two or more DAAs is a combination of IDX21437, an HCV NS5A inhibitor, and another HCV polymerase inhibitor; and the patient is infected with HCV genotype 1. In another example, the combination of two or more DAAs is a combination of IDX21437, an HCV NS5A inhibitor, and another HCV polymerase inhibitor; and the patient is a treatment-naïve patient infected with HCV genotype 1. In another example, the combination of two or more DAAs is a combination of IDX21437, an HCV NS5A inhibitor, and another HCV polymerase inhibitor; and the patient is an interferon non-responder infected with HCV genotype 1. In yet another example, the combination of two or more DAAs comprises IDX21437, an HCV NS5A inhibitor, and an HCV protease inhibitor. In yet another example, the combination of two or more DAAs comprises IDX21437, an HCV NS5A inhibitor, and an HCV protease inhibitor; and the patient is infected with HCV genotype 1. In yet another example, the combination of two or more DAAs comprises IDX21437, an HCV NS5A inhibitor, and an HCV protease inhibitor; and the patient is a treatment-naïve patient infected with HCV genotype 1. In yet another example, the combination of two or more DAAs comprises IDX21437, an HCV NS5A inhibitor, and an HCV protease inhibitor; and the patient is an interferon non-responder infected with HCV genotype 1. In yet another example, the combination of two or more DAAs comprises IDX21437, an HCV protease inhibitor, and another HCV polymerase inhibitor. In yet another example, the combination of two or more DAAs comprises IDX21437, an HCV protease inhibitor, and another HCV polymerase inhibitor; and the patient is infected with HCV genotype 1. In yet another example, the combination of two or more DAAs comprises IDX21437, an HCV protease inhibitor, and another HCV polymerase inhibitor; and the patient is a treatment-naïve patient infected with HCV genotype 1. In yet another example, the combination of two or more DAAs comprises IDX21437, an HCV protease inhibitor, and another HCV polymerase inhibitor; and the patient is an interferon non-responder infected with HCV genotype 1. In yet another example, the combination of two or more DAAs comprises sofosbuvir, GS-5885, and another HCV polymerase inhibitor. In yet another example, the combination of two or more DAAs comprises sofosbuvir, GS-5885, and another HCV polymerase inhibitor; and the patient is infected with HCV genotype 1. In yet another example, the combination of two or more DAAs comprises sofosbuvir, GS-5885, and another HCV polymerase inhibitor; and the patient is a treatment-naïve patient infected with HCV genotype 1. In yet another example, the combination of two or more DAAs comprises sofosbuvir, GS-5885, and another HCV polymerase inhibitor; and the patient is an interferon non-responder infected with HCV genotype 1. In yet another example, the combination of two or more DAAs comprises sofosbuvir, GS-5816, and another HCV polymerase inhibitor. In yet another example, the combination of two or more DAAs comprises sofosbuvir, GS-5816, and another HCV polymerase inhibitor; and the patient is infected with HCV genotype 1. In yet another example, the combination of two or more DAAs comprises sofosbuvir, GS-5816, and another HCV polymerase inhibitor; and the patient is a treatment-naïve patient infected with HCV genotype 1. In yet another example, the combination of two or more DAAs comprises sofosbuvir, GS-5816, and another HCV polymerase inhibitor; and the patient is an interferon non-responder infected with HCV genotype 1. In yet another example, the combination of two or more DAAs comprises sofosbuvir, GS-5885, and an HCV protease inhibitor. In yet another example, the combination of two or more DAAs comprises sofosbuvir, GS-5885, and an HCV protease inhibitor; and the patient is infected with HCV genotype 1. In yet another example, the combination of two or more DAAs comprises sofosbuvir, GS-5885, and an HCV protease inhibitor; and the patient is a treatment-naïve patient infected with HCV genotype 1. In yet another example, the combination of two or more DAAs comprises sofosbuvir, GS-5885, and an HCV protease inhibitor; and the patient is an interferon non-responder infected with HCV genotype 1. In yet another example, the combination of two or more DAAs comprises sofosbuvir, GS-5816, and an HCV protease inhibitor. In yet another example, the combination of two or more DAAs comprises sofosbuvir, GS-5816, and an HCV protease inhibitor; and the patient is infected with HCV genotype 1. In yet another example, the combination of two or more DAAs comprises sofosbuvir, GS-5816, and an HCV protease inhibitor; and the patient is a treatment-naïve patient infected with HCV genotype 1. In yet another example, the combination of two or more DAAs comprises sofosbuvir, GS-5816, and an HCV protease inhibitor; and the patient is an interferon non-responder infected with HCV genotype 1. In yet another example, the combination of two or more DAAs comprises IDX21437, MK-8742, and another HCV polymerase inhibitor. In yet another example, the combination of two or more DAAs comprises IDX21437, MK-8742, and another HCV polymerase inhibitor; and the patient is infected with HCV genotype 1. In yet another example, the combination of two or more DAAs comprises IDX21437, MK-8742, and another HCV polymerase inhibitor; and the patient is a treatment-naïve patient infected with HCV genotype 1. In yet another example, the combination of two or more DAAs comprises IDX21437, MK-8742, and another HCV polymerase inhibitor; and the patient is an interferon non-responder infected with HCV genotype 1. In yet another example, the combination of two or more DAAs comprises IDX21437, MK-8742, and an HCV protease inhibitor. In yet another example, the combination of two or more DAAs comprises IDX21437, MK-8742, and an HCV protease inhibitor; and the patient is infected with HCV genotype 1. In yet another example, the combination of two or more DAAs comprises IDX21437, MK-8742, and an HCV protease inhibitor; and the patient is a treatment-naïve patient infected with HCV genotype 1. In yet another example, the combination of two or more DAAs comprises IDX21437, MK-8742, and an HCV protease inhibitor; and the patient is an interferon non-responder infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 100 or 200 mg Compound 3 together with 100 mg ritonavir once daily, 25 mg compound 4 once daily, and 400 mg sofosbuvir once daily; and the patient is an interferon non-responder infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is a treatment-naïve patient infected with HCV genotype 1. In still another example, the combination of two or more DAAs is a combination of Compound 3, Compound 4, and sofosbuvir; and the method comprises administering 150 mg Compound 3 together with 100 mg ritonavir once daily, 25 mg compound 4 once daily, and 400 mg sofosbuvir once daily; and the patient is an interferon non-responder infected with HCV genotype 1.

In any method described herein, the HCV polymerase inhibitor recited therein can be IDX21437 (a uridine nucleotide analog HCV NS5B polymerase inhibitor, Idenix).

In any method described herein, the HCV polymerase inhibitor recited therein can also be IDX21459.

In any method described herein, the HCV NS5A inhibitor recited therein can be GS-5816.

In any method described herein, the HCV NS5A inhibitor recited therein can also be MK-8742.

In any method described herein, the patient being treated preferably is HCV genotype 1 patient.

It should be understood that the above-described embodiments and the following examples are given by way of illustration, not limitation. Various changes and modifications within the scope of the present invention will become apparent to those skilled in the art from the present description.

Example 1. Clinical Modeling for Interferon-Free DAA Combination Therapies

Treatment regimens comprising administration of Compound 1 and Compound 2 were evaluated using clinical models described in U.S. Patent Application Publication No. 2013/0102526, filed Oct. 19, 2012 and entitled "Methods for Treating HCV", which is incorporated herein by reference in its entirety. These treatment regimens comprised administration of Compound 1 and Compound 2, but did not include administration of either interferon or ribavirin. Comparable SVR rates are expected for interferon-non responders.

FIG. 1 shows the predicted median SVR percentages and 90% SVR confidence intervals for 2-DAA regimens consisting of the use of Compound 1 (400 mg once daily) and Compound 2 (120 mg once daily) to treat genotype 1 naïve subjects. Different treatment durations were assessed. The predicted SVR rate for a 12-week treatment was about 95%. As used in all of the figures of the present application, the vertical bar at the top of each SVR percentage column represents the 90% SVR confidence interval, and the x-axis ("Time (weeks)") indicates the duration of each treatment regimen.

Figure 2:
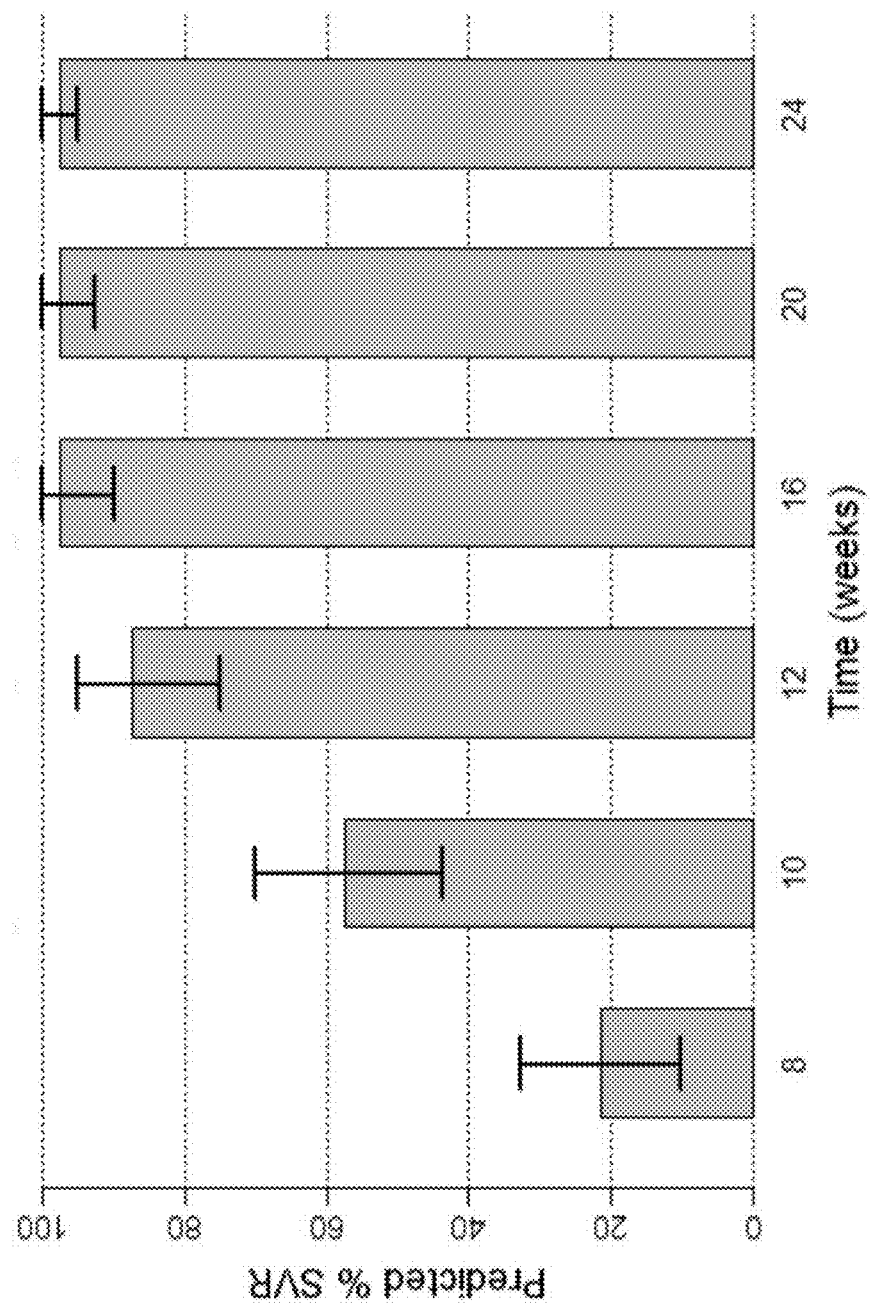
FIG. 2 illustrates the predicted median SVR percentages and 90% SVR confidence intervals for interferon/ribavirin-free, 2-DAA regimens comprising the use of Compound 1 (400 mg once daily) and Compound 2 (60 mg once daily) to treat genotype 1 naïve subjects.

FIG. 2 illustrates the predicted median SVR percentages and 90% SVR confidence intervals for 2-DAA regimens consisting of the use of Compound 1 (400 mg once daily) and Compound 2 (60 mg once daily) to treat genotype 1 naïve subjects. Different treatment durations were assessed. The predicted SVR rate for a 12-week treatment was about 85-90%.

Figure 3:
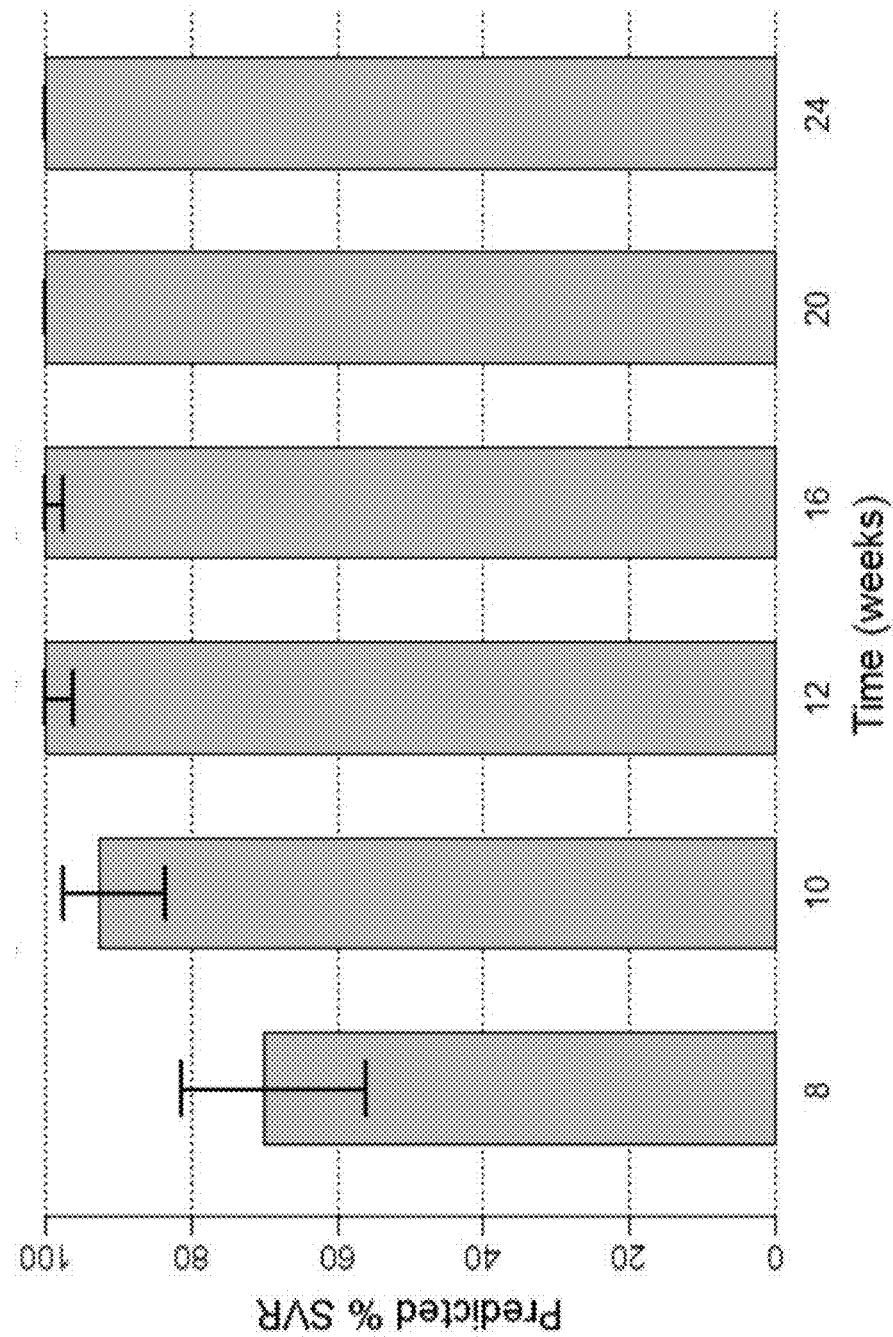
FIG. 3 depicts the predicted median SVR percentages and 90% SVR confidence intervals for interferon/ribavirin-free, 2-DAA regimens comprising the use of Compound 1 (600 mg once daily) and Compound 2 (480 mg once daily) to treat genotype 1 naïve subjects.

FIG. 3 shows the predicted median SVR percentages and 90% SVR confidence intervals for 2-DAA regimens consisting of the use of Compound 1 (600 mg once daily) and Compound 2 (480 mg once daily) to treat genotype 1 naïve subjects. Different treatment durations were assessed. The predicted SVR rate for a 12-week treatment was about 100%.

Figure 4:
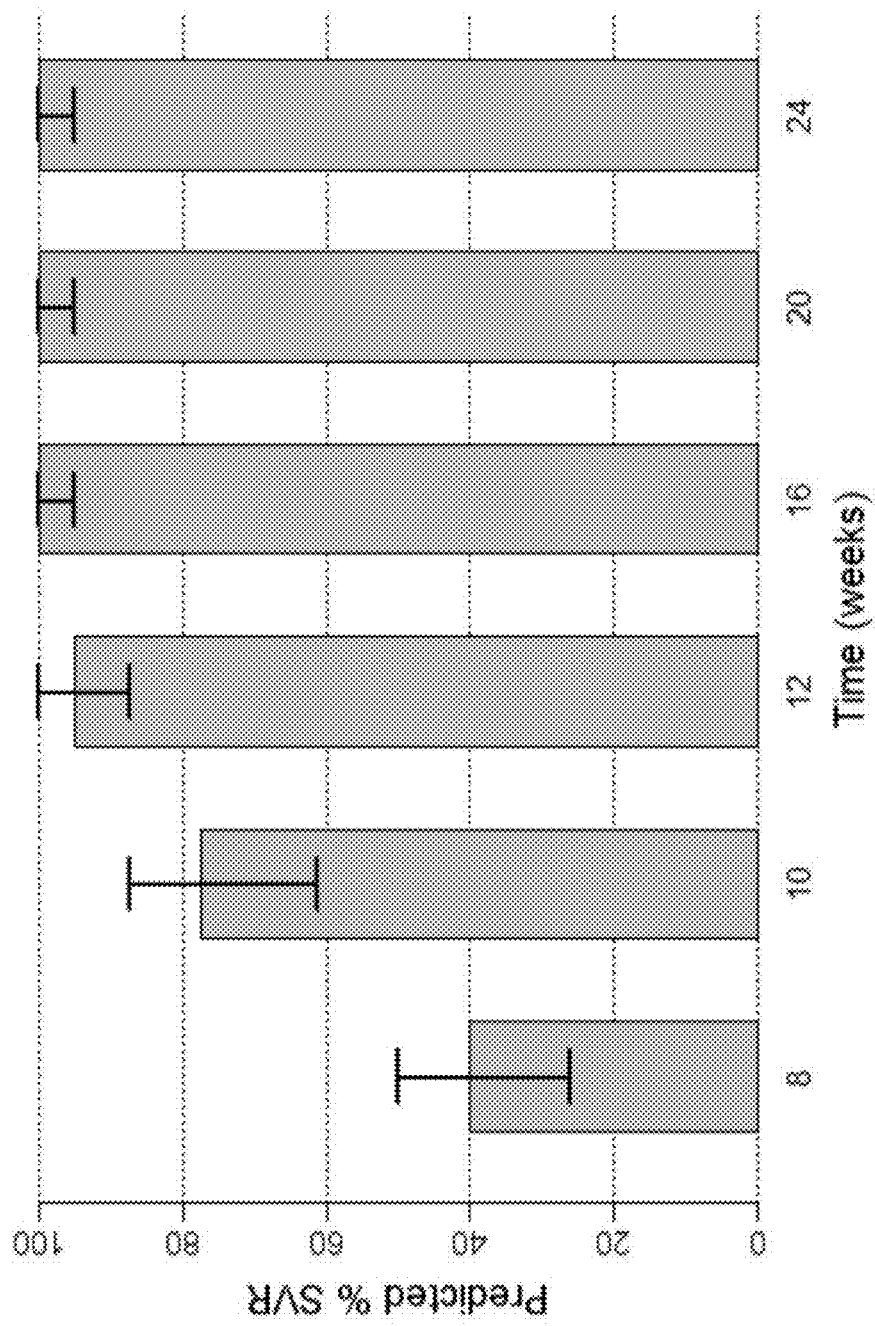
FIG. 4 shows the predicted median SVR percentages and 90% SVR confidence intervals for interferon/ribavirin-free, 2-DAA regimens comprising the use of Compound 1 (400 mg once daily) and Compound 2 (120 mg once daily) to treat genotype 3 naïve subjects.

FIG. 4 depicts the predicted median SVR percentages and 90% SVR confidence intervals for 2-DAA regimen consisting of the use of Compound 1 (400 mg once daily) and Compound 2 (120 mg once daily) to treat genotype 3 naïve subjects. Different treatment durations were assessed. The predicted SVR rate for a 12-week treatment was about 95%.

Figure 5:
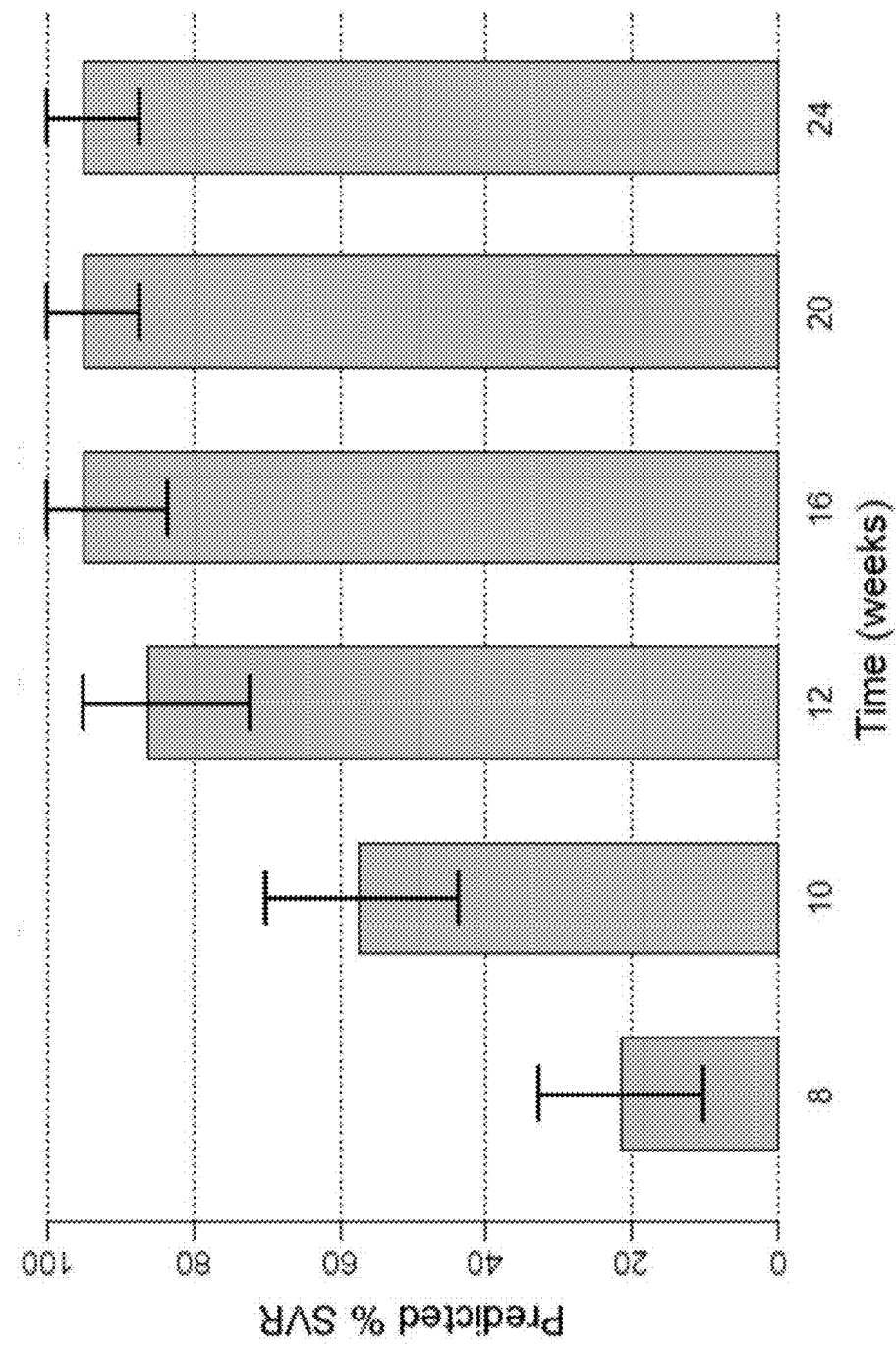
FIG. 5 illustrates the predicted median SVR percentages and 90% SVR confidence intervals for interferon/ribavirin-free, 2-DAA regimens comprising the use of Compound 1 (400 mg once daily) and Compound 2 (60 mg once daily) to treat genotype 3 naïve subjects.

FIG. 5 illustrates the predicted median SVR percentages and 90% SVR confidence intervals for 2-DAA regimen consisting of the use of Compound 1 (400 mg once daily) and Compound 2 (60 mg once daily) to treat genotype 3 naïve subjects. Different treatment durations were assessed. The predicted SVR rate of a 12-week treatment was about 85-90%.

Figure 6:
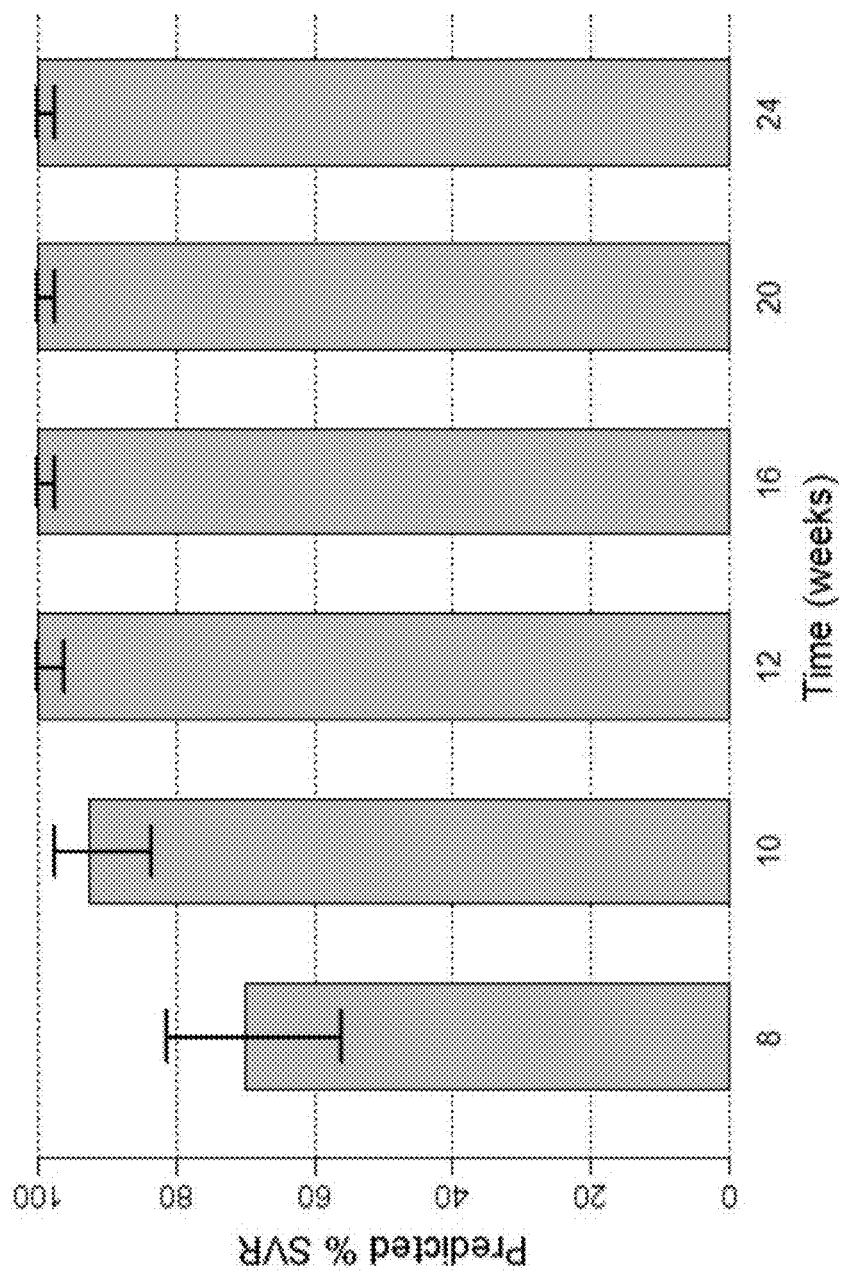
FIG. 6 shows the predicted median SVR percentages and 90% SVR confidence intervals for interferon/ribavirin-free, 2-DAA regimens comprising the use of Compound 1 (600 mg once daily) and Compound 2 (480 mg once daily) to treat genotype 3 naïve subjects.

FIG. 6 shows the predicted median SVR percentages and 90% SVR confidence intervals for 2-DAA regimens consisting of the use of Compound 1 (600 mg once daily) and Compound 2 (480 mg once daily) to treat genotype 3 naïve subjects. Different treatment durations were assessed. The predicted SVR rate of a 12-week treatment was about 100%.

Figure 7:
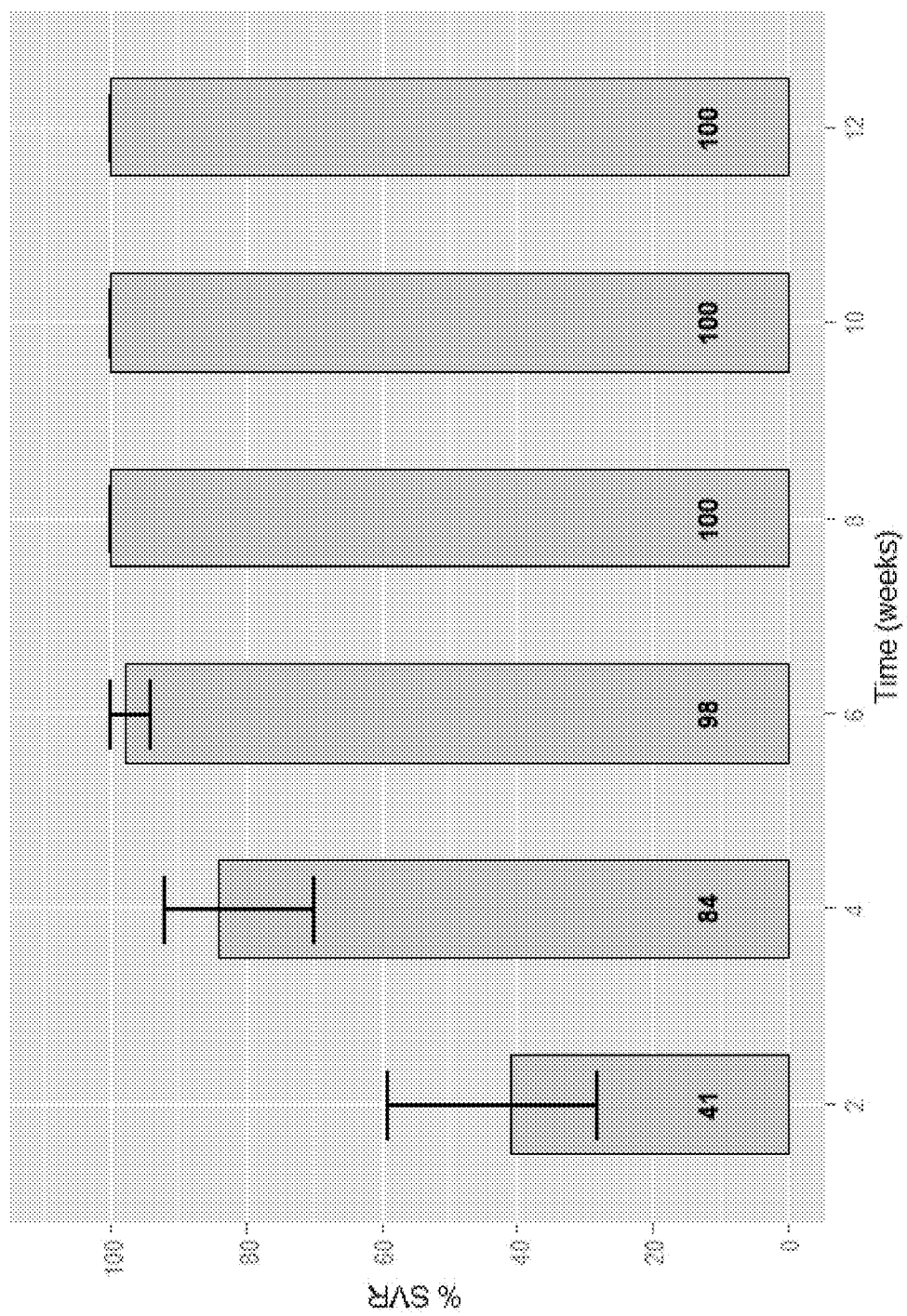
FIG. 7 shows the predicted median SVR percentages and 90% SVR confidence intervals for interferon/ribavirin-free, 3-DAA regimens comprising the use of Compound 1 (400 mg once daily), Compound 2 (120 mg once daily) and sofosbuvir (400 mg once daily) to treat genotype 1 naïve subjects.

Treatment regimens comprising administration of Compound 1, Compound 2 and sofosbuvir, or Compound 2 and sofosbuvir, were also evaluated using the same clinical model. FIG. 7 shows the predicted SVR for the treatment regimen consisting of the use of Compound 1 (400 mg once daily), Compound 2 (120 mg once daily) and sofosbuvir (400 mg once daily) to treat genotype 1 naïve subjects. The treatment regimen did not include administration of either interferon or ribavirin. Different treatment durations were assessed. The predicted SVR rates of the 2-week, 4-week, 6-week, 8-week, 10-week, and 12-week treatment regimens were about 40%, 85%, 100%, 100%, 100%, and 100%, respectively. Comparable SVR rates are expected for interferon-non responders.

Figure 8:
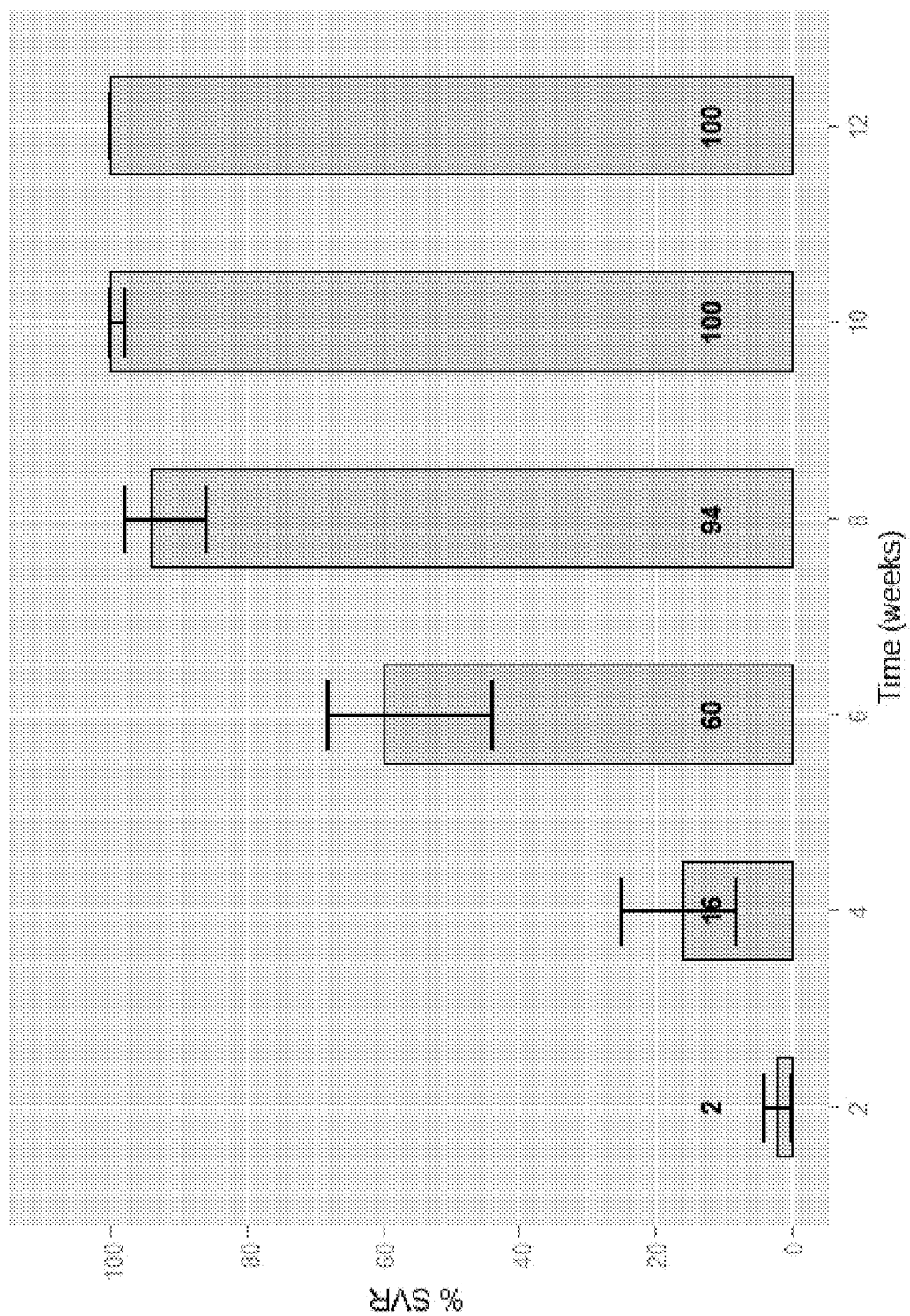
FIG. 8 shows the predicted median SVR percentages and 90% SVR confidence intervals for interferon/ribavirin-free, 2-DAA regimens comprising the use of Compound 2 (120 mg once daily) and sofosbuvir (400 mg once daily) to treat genotype 1 naïve subjects.

FIG. 8 shows the predicted SVR for the treatment regimen consisting of the use of Compound 2 (120 mg once daily) and sofosbuvir (400 mg once daily) to treat genotype 1 naïve subjects. The treatment regimen did not include administration of either interferon or ribavirin. Different treatment durations were assessed. The predicted SVR rates of the 6-week, 8-week, 10-week, and 12-week treatment regimens were about 60%, 95%, 100%, and 100%, respectively. Comparable SVR rates are expected for interferon-non responders.

Example 2. Combination of Compound 1 and Compound 2 In Vitro

Figure 9:
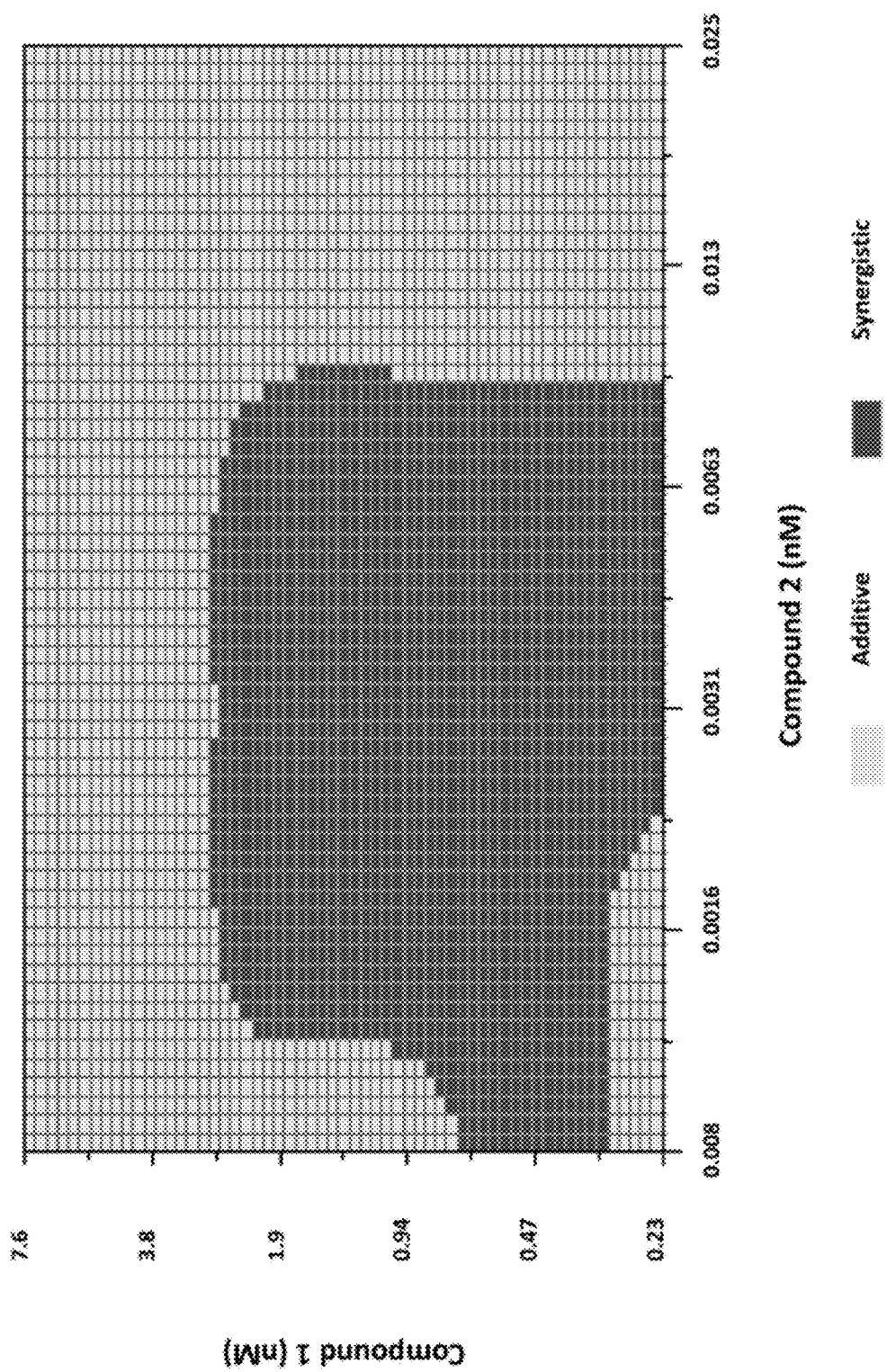
FIG. 9 depict the synergistic effect of the combination of Compound 1 and Compound 2 on HCV inhibition in vitro.

FIG. 9 shows that the combination of Compound 1 and Compound 2 exhibits significant synergistic effect on HCV inhibition as tested in HCV GT 1b Con-1 replication cells. The result was generated using Prichard and Shipman model (Prichard et al. ANTIVIRAL RESEARCH 14:181-205 (1990)).

Compound 1 inhibited replication of HCV stable subgenomic replicons containing NS3 genes from GT 1a, 1b, 2a, 3a, 4a, or 6a with $EC_{50}$ values ranging from 0.85 to 2.8 nM. Of note, Compound 1 was potent against replicon containing GT3a protease, with an $EC_{50}$ value of 1.6 nM. Compound 1 retained its activity against common GT1a and 1b variants at NS3 amino acid positions 155 and 168 that conferred resistance to other HCV protease inhibitors (PIs). Resistant colony selection studies in GT1a and 1b subgenomic replicon cells identified A156T in GT1a and A156V in GT1b as the most frequent variants, which conferred 1400- and 1800-fold reduced susceptibility to Compound 1, respectively. However, these variants had in vitro replication capacities of only 1.5% and 9.2% that of their corresponding wild-type replicons. In a replicon containing GT3a NS3 protease, Compound 1 selected very few colonies at concentrations ≥100-fold over its EC50 value. The colonies that survived the selection contained either A156G alone, or Q168R co-selected with Y56H, which conferred 1500- or 1100-fold loss in susceptibility to Compound 1, respectively.

TABLE 2

Antiviral Activity of Compound 1 in the HCV Subgenomic Stable Replicon Cell Culture Assay

| HCV Replicon Subtype | $N^b$ | 0% Human Plasma$^a$ Mean $EC_{50}$, nM, ±Std. Dev. |
|---|---|---|
| Genotype 1a | 9 | 0.85 ± 0.15 |
| Genotype 1b | 8 | 0.94 ± 0.35 |
| Genotype 2a | 2 | 2.7 ± 1.1 |
| Genotype 3a | 2 | 1.6 ± 0.49 |
| Genotype 4a | 4 | 2.8 ± 0.41 |
| Genotype 6a | 4 | 0.86 ± 0.11 |

$^a$The 0% human plasma assay contains 5% fetal bovine serum
$^b$Number of independent replicates

TABLE 3

Antiviral Activity of Compound 1 in the HCV Subgenomic Stable Replicon Cell Culture Assay

| HCV Replicon Subtype | $N^b$ | 40% Human Plasma$^a$ Mean $EC_{50}$, nM, ±Std. Dev. |
|---|---|---|
| Genotype 1a | 10 | 5.3 ± 1.0 |
| Genotype 1b | 8 | 10 ± 5.0 |

$^a$The 0% human plasma assay contains 5% fetal bovine serum
$^b$Number of independent replicates When tested against common HCV genotype 1 NS3 resistance-associated variants, such as V36M, R155K, D168A and D168V in GT 1a (H77), or T54A, R155K, D168V and V170A in GT 1b (Con-1), Compound 1 showed inhibitory activity nearly equivalent to that against wild-type HCV replicon. Compound 1 was also shown to have potent activity against many NS5A inhibitor and NS5B inhibitor resistance-associated variants in vitro (e.g., M28T, M28V, Q30D, Q30R, Y93C, Y93H, Y93N, L31V+Y93H, C316Y, M414T, Y448C, Y448H, S556G and S559G in GT 1a, and L28T, Y93H, S282T, C316Y, Y448H and S556G in GT 1b).

Example 3. High SVR in HCV Genotype 1 (GT1) Non-Cirrhotic Treatment-Naïve Patients or Pegylated Interferon/Ribavirin Null Responders Treated with the Combination of Compound 1 and Compound 2

Compound 1 and Compound 2 are characterized by potent pangenotypic in vitro antiviral activity against major HCV genotypes (GTs), including activity against key known resistance-associated variants and a high barrier to resistance selection. Monotherapy with Compound 1 or Compound 2 resulted in a mean 4 $\log_{10}$ IU/mL decline from baseline in HCV plasma viral load in GT1-infected subjects with and without compensated cirrhosis.

In this phase 2 study, treatment with Compound 1 and Compound 2 for 12 weeks is evaluated in HCV GT1-infected subjects without cirrhosis. Non-cirrhotic GT1-infected treatment-naïve (TN) or pegylated interferon/ribavirin (pegIFN/RBV) null responder subjects received once-daily Compound 1 200 mg+Compound 2 120 or 40 mg for 12 weeks, and subsequently were followed for 24 weeks. Efficacy was measured by sustained virologic response after the last dose of study drug (SVR). Safety was evaluated by adverse event (AE) monitoring, laboratory testing, and other standard assessments.

79 subjects (male, 52%; median [range] age, 54.0 [26.0-70.0] years; GT1a, 81%; GT1b, 19%; TN, 63%; pegIFN/RBV null responders, 37%; fibrosis >F2, 25%; median [range] HCV RNA $\log_{10}$ IU/mL, 6.8 [4.4-7.5]) were enrolled, 40 received Compound 1 200 mg+Compound 2 120 mg, and 39 received Compound 1 200 mg and Compound 2 40 mg. SVR 4 weeks after the last dose of study drug (SVR4) was achieved in 29 of 29 (100%) pegIFN/RBV null responders and 49 of 50 (98%) TN subjects. There were no treatment-related serious AEs or clinically relevant laboratory findings. The most common AEs (reported in >5% of subjects) were fatigue, headache, nausea, diarrhea, and anxiety.

Once-daily 12-week treatment with the combination of Compound 1 and Compound 2 of GT1 infection in non-cirrhotic TN and pegIFN/RBV null responders resulted in high SVR4 (98%-100%) rates. One treatment relapse was observed.

Non-cirrhotic HCV GT1-infected patients treated with the combination of Compound 1 and Compound 2 for 12 weeks achieved high SVR12 rates, regardless of prior treatment experience or presence of baseline variants.

Treatment with the combination of Compound 1 and Compound 2 for 12 weeks is also expected to achieve high SVR in GT1 subjects with compensated cirrhosis. Likewise, high SVR is expected in GT1 patients if treated with the combination of Compound 1 and Compound 2 once-daily for only 8 weeks. Suitable dosing includes, but is not limited to, Compound 1 300 mg+Compound 2 120 mg once daily, or Compound 1 200 mg+Compound 2 80 mg once daily.

Example 4. High SVR Achieved with Compound 1 and Compound 2 in Non-Cirrhotic Treatment-Naïve and Treatment-Experienced Patients with HCV Genotype 2 (GT2) Infection As shown in Example 3, Compound 1 and Compound 2 are potent inhibitors against GT1. Compound 1 and Compound 2 have comparable in vitro antiviral potency against GT2. This Example evaluates the efficacy and safety of Compound 1 and Compound 2 with or without ribavirin (RBV) in non-cirrhotic GT2-infected treatment-naïve (TN) and pegylated interferon/RBV (pegIFN/RBV) treatment experienced (TE) subjects.

Subjects received 12 weeks of Compound 1 300 mg+Compound 2 120 mg (Arm A), Compound 1 200 mg+Compound 2 120 mg (Arm B), or Compound 1 200 mg+Compound 2 120 mg+RBV (Arm C). DAAs were dosed once daily; weight-based RBV (1000 or 1200 mg) was dosed twice daily. Subjects were then followed for 24 weeks. Efficacy was measured by sustained virologic response after the last dose of study drug (SVR). Safety was evaluated by monitoring adverse events (AEs), laboratory tests, and vital signs.

75 subjects were treated in Arms A-C (n=25 each); 74 had GT2, and 1 subject initially randomized to Arm B was determined to have GT3a infection. Subjects were male, 63%; median (range) age, 57.0 (20.0-69.0) years; GT2b, 81%; TN, 88%; TE, 12%; F0-F2, 87%; F3, 13%; median (range) baseline HCV RNA $\log_{10}$ IU/mL, 7.1 (4.7-7.8). No subjects have experienced virologic failure. One subject in Arm A prematurely discontinued study drugs and was lost to follow-up. The SVR4 rates (ITT analysis) are 96% (24/25), 100% (24/24), and 100% (25/25) in Arms A, B, and C, respectively. Most AEs were mild, with the most common DAA-related AEs being fatigue, nausea, headache, and diarrhea. There were no serious DAA-related AEs. Typical reductions in hemoglobin were observed in the RBV-containing arm.

Compound 1+Compound 2 with or without RBV for 12 weeks was highly effective and well tolerated, achieving SVR4 rates of 96%-100%.

The once daily regimen of the combination of Compound 1 and Compound 2 was well tolerated and demonstrated high SVR12 rates, regardless of prior treatment experience or presence of baseline variants in non-cirrhotic patients with GT2 infection.

Treatment with the combination of Compound 1 and Compound 2 for 12 weeks is also expected to achieve high SVR in GT2 subjects with compensated cirrhosis. Likewise, high SVR is expected in GT2 patients if treated with the combination of Compound 1 and Compound 2 once-daily for only 8 weeks. Suitable dosing includes, but is not limited to, Compound 1 300 mg+Compound 2 120 mg once daily, or Compound 1 200 mg+Compound 2 80 mg once daily.

Example 5. High SVR Achieved with Compound 1 and Compound 2 in Non-Cirrhotic Treatment-Naïve and Treatment-Experienced Patients with HCV Genotype 3 (GT3) Infection As shown in Example 3, Compound 1 and Compound 2 are potent inhibitors against GT1. Compound 1 and Compound 2 have comparable in vitro antiviral potency against GT3. This Example evaluates the efficacy and safety of Compound 1 and Compound 2 with or without ribavirin (RBV) in non-cirrhotic GT3-infected treatment-naïve (TN) and pegylated interferon/RBV (pegIFN/RBV) treatment experienced (TE) subjects.

Subjects received 12 weeks of Compound 1 300 mg+Compound 2 120 mg (Arm D), Compound 1 200 mg+Compound 2 120 mg (Arm E), Compound 1 200 mg+Compound 2 120 mg+RBV (Arm F), or Compound 1 200 mg+Compound 2 40 mg (Arm G). DAAs were dosed once daily; weight-based RBV (1000 or 1200 mg) was dosed twice daily. Efficacy was measured by sustained virologic response after the last dose of study drug (SVR). Safety was evaluated by monitoring adverse events (AEs), laboratory tests, and vital signs.

120 GT3-infected subjects were treated in Arms D (n=30), E (n=29), F (n=31), or G (n=30). Subjects were male, 56%; median age, 52.0 years; GT3a, 98%; TN, 92%; TE, 8%; fibrosis >F2, 15%; median baseline HCV RNA $\log_{10}$ IU/mL, 6.7. There has been 1 virologic failure in each treatment arm (n=4), 3 of which were in pegIFN/RBV TE subjects. One subject in Arm G was lost to follow-up at the week 2 visit. The SVR4 rate was 96% (27/28), 96% (27/28), 97% (29/30) and 93% (27/29) in Arms D, E, F, and G, respectively. AEs were mostly mild, with most common DAA-related AEs being fatigue, nausea, and headache. There were no serious DAA-related AEs; 1 subject discontinued due to DAA- and RBV-related AEs of abdominal pain and heat sensation. Typical reductions in hemoglobin were observed in the RBV containing arm (Arm F).

Compound 1+Compound 2 treatment for 12 weeks with or without RBV in TN or TE non-cirrhotic HCV GT3-infected subjects was well tolerated. Promising SVR4 rates of 93%-96% were achieved without RBV. Further testing showed that Arms D, E, F and G achieved 93%, 93%, 94% and 83% SVR12, respectively.

Treatment with the combination of Compound 1 and Compound 2 for 12 weeks is also expected to achieve high SVR in GT3 subjects with cirrhosis. Likewise, high SVR is expected in GT3 patients if treated with the combination of Compound 1 and Compound 2 once-daily for only 8 weeks. Suitable dosing includes, but is not limited to, Compound 1 300 mg+Compound 2 120 mg once daily, or Compound 1 200 mg+Compound 2 80 mg once daily.

Example 6. Drug-Drug Interactions Between Compound 1 and Compound 2 with Cyclosporine or Tacrolimus in Healthy Subjects Compound 1+Compound 2 combination demonstrated high sustained virologic response rate in Phase 2 studies. Two Phase 1, open-label studies were conducted to assess the pharmacokinetics, safety and tolerability when Compound 1+Compound 2 is coadministered with immunosuppressants cyclosporine or tacrolimus.

Healthy adults subjects received single doses of cyclosporine 100 mg (n=12) or tacrolimus 1 mg (n=12) alone or in combination with Compound 1 300 mg QD (i.e., once daily)+Compound 2 120 mg QD. Intensive blood sampling for determination of cyclosporine, tacrolimus, Compound 1 and Compound 2 concentrations was performed and pharmacokinetic parameters (maximum observed concentration [$C_{max}$], area under the concentration-time curve [$AUC_t$ or $AUC_{inf}$] and trough concentration [$C_{24}$]) were estimated. Safety and tolerability were assessed throughout the study.

Cyclosporine $C_{max}$, $AUC_t$, and $AUC_{inf}$ in blood were minimally affected (≤14% change) when coadministered with steady-state Compound 1+Compound 2. Steady-state $C_{max}$, $AUC_{24}$, and $C_{24}$ in plasma were slightly increased for Compound 1 (30%, 37%, and 34%, respectively) and for Compound 2 (11%, 22%, and 26%, respectively) when coadministered with cyclosporine. Tacrolimus $C_{max}$, $AUC_t$, and $AUC_{inf}$ in blood were slightly increased (50%, 53%, and 45%, respectively) when coadministered with steady-state Compound 1+Compound 2. Steady-state $C_{max}$, $AUC_{24}$, and $C_{24}$ in plasma were minimally affected for Compound 1 (≤11% change) and for Compound 2 (≤2% change) when coadministered with tacrolimus.

No serious adverse events were observed in either study. There were no patterns to the adverse events reported, and no new safety issues were identified.

No dose adjustment should be required for Compound 1, Compound 2, and cyclosporine when coadministered. No dose adjustment should be required for Compound 1 and Compound 2 when coadministered with tacrolimus. It may be considered that subjects receiving tacrolimus should continue to use their current dose when initiating treatment with DAAs, and reduce the dose of tacrolimus if necessary based on therapeutic monitoring.

Example 7. Absence of Significant Drug-Drug Interactions Between Compound 1/Compound 2 and Methadone or Buprenorphine/Naloxone in Subjects on Opioid Maintenance Therapy A Phase 1, open-label study was conducted to assess the pharmacokinetics, safety and tolerability of Compound 1+Compound 2 and methadone or buprenorphine/naloxone. Otherwise healthy adults subjects on individualized regimens of methadone (n=12) or buprenorphine/naloxone (n=12) for opioid addiction received Compound 1 300 mg QD+Compound 2 120 mg QD for 7 days. Intensive blood sampling for determination of methadone, buprenorphine, norbuprenorphine, naloxone, Compound 1 and Compound 2 concentrations was performed and pharmacokinetic parameters (maximum observed concentration [$C_{max}$], area under the concentration-time curve [$AUC_{24}$ or $AUC_t$] and trough concentration [$C_{24}$]) were estimated. Safety and tolerability were assessed throughout the study. Potential opioid withdrawal or overdose symptoms (pharmacodynamics) were assessed with validated instruments including the short opiate withdrawal scale, desire for drugs questionnaire, and pupillometry measurements throughout the study.

For subjects on methadone maintenance therapy, dose-normalized $C_{max}$, $AUC_{24}$, and $C_{24}$ for R- and S-methadone were unaffected by coadministration with Compound 1 and Compound 2 at steady-state (≤5% change). For subjects on buprenorphine/naloxone maintenance therapy, dose-normalized $C_{max}$, $AUC_{24}$, and $C_{24}$ were slightly increased for buprenorphine (8%, 17%, and 24%, respectively) and norbuprenorphine (25%, 30%, and 21%, respectively) when coadministered with Compound 1 and Compound 2 at steady-state; naloxone dose-normalized $C_{max}$ and $AUC_t$ were minimally affected (≤12% change). Pharmacodynamics of the methadone or buprenorphine/naloxone regimens were not significantly impacted by coadministration with Compound 1 or Compound 2 for either regimen. Compound 1 and Compound 2 exposures following coadministration with methadone or buprenorphine/naloxone were similar to the observed values in previous studies.

Subjects experienced adverse events of mild intensity, with the most common (reported in >5 subjects) being abdominal pain, constipation, and headache; all subjects completed the study. There were no clinically relevant abnormal laboratory abnormalities, ECG or vital sign findings.

No dose adjustments should be required for coadministration of Compound 1 and Compound 2 with methadone or buprenorphine/naloxone. No pharmacodynamic interaction is expected.

Example 8. Pharmacokinetics of Coadministration of Pan-Genotypic, Direct Acting Antiviral Agents, Compound 1 and Compound 2, with or without Ribavirin for 12 Weeks in HCV Infected Subjects without Cirrhosis Pharmacokinetics of Compound 1 and Compound 2 with or without ribavirin (RBV) were evaluated. Two open-label, multicenter studies were conducted to evaluate the efficacy, safety, and pharmacokinetics of co-administration of Compound 1 (200 or 300 mg QD) and Compound 2 (40 or 120 mg QD) with or without RBV in GT1-, GT2- or GT3-infected subjects. Blood samples for pharmacokinetic analysis were collected throughout the study treatment period. Compound 1 and Compound 2 pharmacokinetics following a single dose (Day 1) and at steady state (Week 4) were assessed by non-compartmental methods.

A total of 274 subjects received Compound 1 and Compound 2 with or without RBV. Both Compound 1 and Compound 2 showed rapid absorption with Tmax ranging from 2 to 4 hours. Steady state Compound 1 exposure (area under the curve from 0 to 4 hour) following 300 mg was 2570 ng·h/mL, approximately 3.7-fold of the exposure following 200 mg administration. Coadministration of either 40 mg or 120 mg Compound 2 each with 200 mg Compound 1 resulted in Compound 2 exposure of 157 or 372 ng·h/mL, respectively. Compound 1 300 mg increased 120 mg Compound 2 exposure by an additional 20% to 30%. Minimal accumulation in Compound 1 or Compound 2 exposure was observed at Week 4 compared to Day 1. Compound 2 had minimal impact on Compound 1 exposures, however, Compound 1 200 mg and 300 mg increased 120 mg Compound 2 exposures to 3- to 4-fold of Compound 2 exposures when administered alone. HCV genotype and RBV coadministration had no impact on Compound 1 or Compound 2 exposures.

Compound 1 exhibited non-linear pharmacokinetics with more than dose-proportional increase in exposures with increasing doses, while Compound 2 exposures increased in an approximately dose-proportional manner when coadministered with Compound 1. Compound 2 had minimal impact on Compound 1, while Compound 1 increased Compound 2 exposures, with the increase in Compound 2 exposure being dependent on Compound 1 dose. Compound 1 or Compound 2 had minimal accumulation in exposures following multiple dosing in HCV-infected subjects.

Example 9. Drug-Drug Interactions Between Compound 1/Compound 2 and Sofosbuvir A Phase 1 study was conducted to evaluate any potential interactions during co-administration of Compound 1+Compound 2 with sofosbuvir. This was an open label, randomized, multiple-dose, non-fasting study in 16 healthy subjects who were assigned 1:1 to one of two cohorts to receive either Compound 1 400 mg QD+Compound 2 120 mg QD or sofosbuvir 400 mg QD for 7 days (Period 1), followed by the combination of Compound 1 400 mg QD+Compound 2 120 mg QD with sofosbuvir 400 mg QD for 7 additional days (Period 2). Intensive pharmacokinetic assessments were performed on Study Days 1 and 7 in each period. Pharmacokinetic interaction between Compound 1+Compound 2 and sofosbuvir were assessed by a repeated-measures analysis using SAS. Safety was evaluated through assessment of adverse events, vital signs, ECGs and clinical laboratory tests.

Coadministration with steady-state Compound 1 and Compound 2 increased sofosbuvir $C_{max}$ and $AUC_{24}$ by 66% and 125%, respectively; $C_{max}$ and $AUC_{24}$ for the major circulating sofosbuvir metabolite GS-331007 were minimally affected (≤21% difference) and $C_{24}$ was increased by 85%. Compound 1 and Compound 2 exposures were minimally affected by sofosbuvir (≤16% difference). There were no patterns to the adverse events reported, and no new safety issues were identified.

This study showed that no dose adjustments are needed for coadministration of Compound 1 and Compound 2 with sofosbuvir.

Example 10. Pharmacokinetics, Tolerability and Safety of Compound 2 Following Single and Multiple Doses in Healthy Subjects The study's objectives were to determine the pharmacokinetics (PK), safety, and tolerability of Compound 2 following single ascending doses (SAD) and multiple ascending doses (MAD) and effect of food on Compound 2 PK in healthy adults. This was a blinded, randomized, placebo-controlled Phase 1 study. Seven Compound 2 doses ranging from 1.5 mg to 600 mg were evaluated in the SAD portion (n=53, 3:1 active to placebo ratio). Compound 2 doses of 30 mg to 600 mg QD were evaluated in MAD portion for 10 days (n=39, 4:1 active to placebo ratio). The effect of food on Compound 2 120 mg was assessed in a crossover fashion in 12 healthy subjects. The PK parameters of Compound 2 were estimated using non-compartmental methods. Safety and tolerability were assessed throughout the study.

Compound 2 exposures increased in a greater than dose proportional manner across the 1.5 mg to 120 mg dose range, while PK was linear across the 120 mg to 600 mg dose range. Compound 2 plasma concentration reached $T_{max}$ at 3 to 5 hours. Following Compound 2 QD dosing for 10 days, the Compound 2 steady state exposures were 53% higher compared to exposures after the first dose. Compound 2 half-lives ranged from 20 to 22 hours. Steady state of Compound 2 was attained by Study Day 5. Food had minimal effect on the bioavailability of Compound 2 (<14%). All adverse events were assessed as mild. No clinically significant vital signs or laboratory measurements were observed during the course of the study.

This study showed that Compound 2 PK support QD dosing and administration without regard to food. All dose levels were well tolerated and a maximum tolerated dose was not reached in the SAD and MAD portions of the study.

Example 11. High SVR in HCV Genotype 1 Non-Cirrhotic Treatment-Naïve or -Experienced Patients with the Combination of Compound 1 and Compound 2 for 8 Weeks Compound 1 and Compound 2 co-administered for 12 weeks showed high sustained virologic response (SVR) rates and was well tolerated in non-cirrhotic patients with HCV genotype 1 (GT1) infection. This Example shows the efficacy and safety data of the combination of Compound 1 and Compound 2 administered for 8 weeks in non-cirrhotic patients with GT1 infection.

Treatment-naïve or pegylated interferon treatment-experienced patients received once-daily Compound 1 300 mg+Compound 2 120 mg for 8 weeks. SVR at post-treatment week 4 ($SVR_4$; HCV RNA measured using COBAS TaqMan® RT-PCR [lower limit of detection of 15 IU/mL and lower limit of quantitation of 25 IU/mL]) and safety data were determined.

34 patients were enrolled: 56% male, 97% white, 71% GT1a, 68% non-CC IL28B, 15% had an F3 fibrosis stage at baseline, and 15% were treatment experienced. The median (range) HCV RNA $log_{10}$ IU/mL was 6.5 (2.9-7.5) at baseline, and 38% of patients had HCV RNA ≥6,000,000 IU/mL. After 8-week treatment, all 34 (100%) patients achieved $SVR_4$ and 97% of the patients achieved SVR12. One patient did not achieve SVR12 after achieving SVR4 due to death from advanced cancer not related to study drugs. There were no additional serious or severe AEs reported. The most frequent AEs observed in >10% of patients were fatigue (21%) and diarrhea (12%).

This study showed that the combination of Compound 1 and Compound 2 was well tolerated and achieved high SVR rate in all treatment-naïve or -experienced patients with GT1 infection who completed 8 weeks of treatment, regardless of baseline viral load, baseline viral load, prior treatment history, or presence of baseline NS3 and/or NS5A variants.

Example 12. High SVR Rates with the Combination of Compound 1+Compound 2 for 8 Weeks in Non-Cirrhotic Patients with HCV Genotype 2 Infection Compound 1+Compound 2 for 12 weeks was well tolerated and achieved sustained virologic response (SVR) rates between 97-100% in non-cirrhotic patients with HCV genotype (GT) 1 or 2 infection. In this Example, Compound 1+Compound 2 was co-administered to HCV GT2 patients for a shorter duration of 8 weeks.

Non-cirrhotic treatment-naïve patients or pegylated interferon/ribavirin treatment-experienced non-responders received once-daily Compound 1 300 mg+Compound 2 120 mg for 8 weeks. HCV RNA <25 IU/mL at post-treatment weeks 4 (SVR4) and safety were evaluated.

54 patients with GT2 infection (70% GT2b; 59% non-CC IL28B genotype; 13% treatment-experienced) were enrolled, respectively. Mean baseline HCV RNA $log_{10}$ IU/mL±standard deviation was 6.6±0.8 for these GT2-infected patients, with 57% of patients who had baseline levels ≥6M IU/mL. SVR4 was achieved by 98% (53/54) of GT2-infected patients. The GT2-infected patient without SVR4 was lost to follow up after week 6, where HCV RNA was not detected. There were no other discontinuations due to AEs. AEs were mostly mild (Grade 1), with the most common AEs being fatigue and headache.

This study showed that the combination of Compound 1 and Compound 2 administered for 8 weeks in non-cirrhotic patients with HCV GT2 infection was well tolerated and achieved high SVR, regardless of baseline viral load or prior treatment history.

Example 13. High SVR Rates with Compound 1+Compound 2 Co-Administered for 8 Weeks in Non-Cirrhotic Patients with HCV Genotype 3 Infection Treatment-naïve HCV GT3-infected patients without cirrhosis received once-daily Compound 1 300 mg+Compound 2 120 mg for 8 weeks. SVR4 (HCV RNA below the lower limit of quantitation [25 IU/mL] at post-treatment week 4) and safety were assessed.

29 patients were enrolled: 52% male, 90% white, 86% GT3a, and 62% non-CC IL28B. The median (range) HCV RNA $\log_{10}$ IU/mL was 6.3 (5.0-7.5) and 24% of patients had HCV RNA ≥6M IU/mL at baseline. SVR4 was achieved by 97% (28/29) of patients. No patients experienced virologic failure to date. One patient discontinued the study after treatment week 6 (HCV RNA undetectable at this visit) due to intolerance of blood draws. No patients discontinued due to adverse events (AEs) or experienced serious AEs. The majority of AEs were mild in severity, with the most common AEs (>10% of patients) reported for patients being headache and fatigue.

This study showed that the combination of Compound 1 and Compound 2, co-administered for 8 weeks in treatment-naïve, non-cirrhotic patients with HCV GT3 infection was well-tolerated and achieved high SVR rates.

Example 14. Antiviral Activity of Compound 2 in Combination with Paritaprevir/Ritonavir and Ribavirin Against Hepatitis C Virus Genotype 3 Infection Efficacy, pharmacokinetics, and safety of Compound 2 co-administered with paritaprevir/ritonavir and ribavirin were evaluated in this phase 2, open-label, multicenter study in treatment-naïve non-cirrhotic patients with HCV genotype 3 infection. Ten patients, all genotype 3a, received 120 mg Compound 2 and 150/100 mg paritaprevir/ritonavir once daily with weight-based ribavirin for 12 weeks. A total daily dose of 1000 mg ribavirin if the patient's body weight was <75 kg or 1200 mg if body weight was ≥75 kg was divided twice daily (BID).

Nine (90%) patients achieved sustained virologic response at post-treatment weeks 12 and 24. One patient experienced virologic failure at treatment week 6. Sequence analyses for HCV variants in samples from this patient identified A166S in NS3 at baseline and after breakthrough, as well as A30K at baseline and linked S24F+M28K+A30K variants in NS5A after breakthrough. Neither NS3 A166S nor NS5A A30K variant confers any resistance to paritaprevir or Compound 2, respectively. However, NS5A S24F+M28K+A30K linked variant confers a >5000-fold increase in Compound 2 $EC_{50}$ relative to that of the wild-type replicon. This patient's Compound 2 exposure was comparable to the cohort, while paritaprevir and ritonavir exposures were the lowest of all patients. No serious or severe adverse events and adverse events leading to early discontinuation were reported.

The study confirmed that Compound 2 in combination with paritaprevir/ritonavir and ribavirin is effective against HCV genotype 3 infection.

Example 15. 100% SVR4 and Favorable Safety of Compound 1+Compound 2 Administered for 12 Weeks in Non-Cirrhotic Patients with Genotypes 4, 5, or 6 Infection This study evaluated the efficacy and safety of Compound 1 and Compound 2 co-administered for 12 weeks in non-cirrhotic patients with HCV genotypes 4, 5, or 6 infection. Treatment-naïve or pegylated interferon/ribavirin treatment-experienced patients received once-daily Compound 1 300 mg+Compound 2 120 mg for 12 weeks. Sustained virologic response at post-treatment week 4 (SVR4; HCV RNA measured using COBAS TaqMan® RT-PCR [lower limit of detection of 15 IU/mL and lower limit of quantitation of 25 IU/mL]) and safety data was assessed.

A total of 34 patients with genotype 4 (n=22; 65%), 5 (n=1; 3%), or 6 (n=11; 32%) infection were enrolled: 53% male, 59% white, 62% had non-CC IL28B, and 15% were treatment-experienced. The median (range) HCV RNA $\log_{10}$ IU/mL was 6.4 (4.6-7.4) at baseline, and 35% of patients had HCV RNA ≥6,000,000 IU/mL. SVR4 was achieved by all 34 (100%) patients with genotypes 4, 5, or 6 infection. Adverse events (AEs) reported were deemed mostly Grade 1 (mild) in severity, with common AEs in >5% of all patients being headache (24%), diarrhea (15%), fatigue (12%), nausea (9%), arthralgia (6%), dizziness (6%), dry mouth (6%), and flatulence (6%). No severe AEs, serious AEs, premature discontinuations due to AEs were reported. While receiving therapy, no liver function or other laboratory abnormalities were observed.

This study showed that the combination of Compound 1 and Compound 2 was well tolerated and demonstrated 100% SVR4 in non-cirrhotic patients with genotype 4, 5, or 6 infection. These results along with previously reported promising efficacy in GT1, 2, and 3 infection establish potent clinical pangenotypic activity of this RBV-free once daily Compound 1+Compound 2 regimen.

Example 16. High Efficacy and Favorable Safety of Compound 1 and Compound 2 Co-Administration for 12 Weeks in HCV Genotype 1-Infected Patients with Cirrhosis This study evaluated the safety and efficacy of Compound 1 and Compound 2 administered for 12 weeks in HCV GT1-infected patients with compensated cirrhosis. Treatment-naïve or pegylated interferon/ribavirin treatment-experienced patients received Compound 1 200 mg+Compound 2 120 mg once daily for 12 weeks. Cirrhosis was determined by either liver biopsy (Metavir F4), Fibroscan (liver stiffness >14.6 KPa) or serum markers (Fibrotest score ≥0.75 and an APRI >2). SVR at post-treatment week 12 (SVR12; HCV RNA levels determined using Roche COBAS TaqMan® RT-PCR assay [lower limit of detection of 15 IU/mL and lower limit of quantification of 25 IU/mL]) and safety were assessed.

A total of 27 patients were enrolled and the population was 74% male, 89% white, 74% GT1a, 85% non-CC IL28B, 26% HCV treatment-experienced, and all reported fibrosis scores of F4 at baseline (1 missing). The median (range) HCV RNA $\log_{10}$ IU/mL was 6.7 (5.6-7.3), and 93% had HCV RNA ≥6,000,000 IU/mL at baseline. Efficacy data shows 26 out of 27 (96%) of patients achieved SVR12, with one patient experiencing relapse at post-treatment week 4. Most adverse events (AEs) were deemed Grade 1 (mild) or Grade 2 (moderate) in severity, with no patients reporting severe or serious AEs considered related to study drugs. No patients discontinued treatment prematurely due to AEs and the most frequent AEs reported in >10% of patients were fatigue (11%) and headache (11%). While on-treatment, no clinically meaningful abnormal liver function or other laboratory results were observed.

The study showed that treatment with the IFN- and ribavirin-free combination of Compound 1 and Compound 2 was well-tolerated and achieved high SVR12 rates of 96% following a 12-week treatment regimen in GT1-infected patients with compensated cirrhosis regardless of baseline viral load or prior treatment history.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A method of curing hepatitis C virus (HCV) infection in a treatment naive patient infected with HCV genotype 1, 2, 3, 4, 5 or 6, the method comprising:
   orally administering a combination of two direct acting antiviral agents (DAAs) once daily for 8 weeks to said patient,
   wherein said combination of two DAAs comprises:
   (1) 300 mg Compound

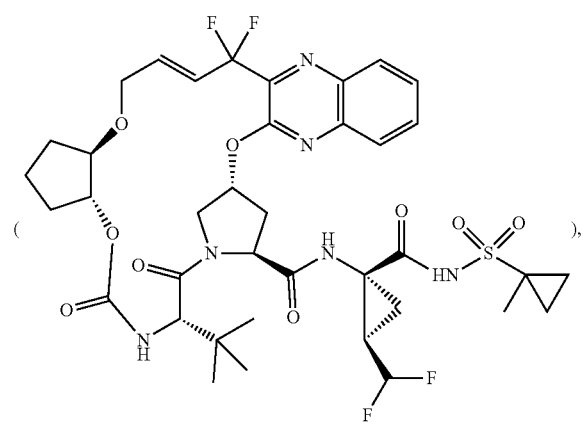

and
   (2) 120 mg Compound 2

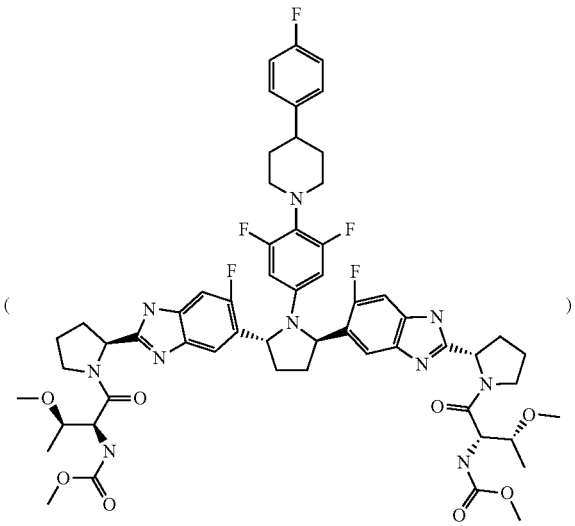

Compound 2

2. A method of curing hepatitis C virus (HCV) infection in a treatment experienced patient infected with HCV genotype 1, 2, 4, 5 or 6, the method comprising:
   orally administering a combination of two direct acting antiviral agents (DAAs) once daily for 12 weeks to said patient,
   wherein said combination of two DAAs comprises:
   (1) 300 mg Compound 1

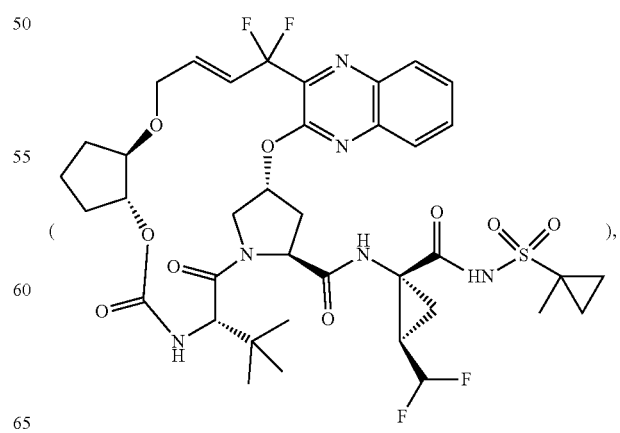

and (2) 120 mg Compound 2

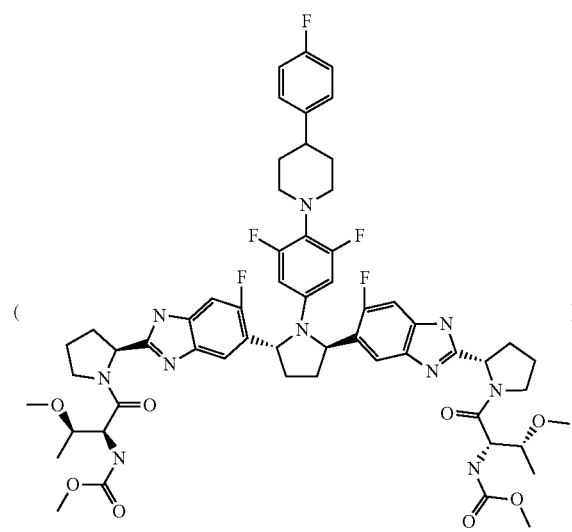

(   ).

3. A method of curing hepatitis C virus (HCV) infection in a treatment experienced patient infected with HCV genotype 1 or 3, the method comprising:

orally administering a combination of two direct acting antiviral agents (DAAs) once daily for 16 weeks to said patient, wherein said combination of two DAAs comprises:

(1) 300 mg Compound 1

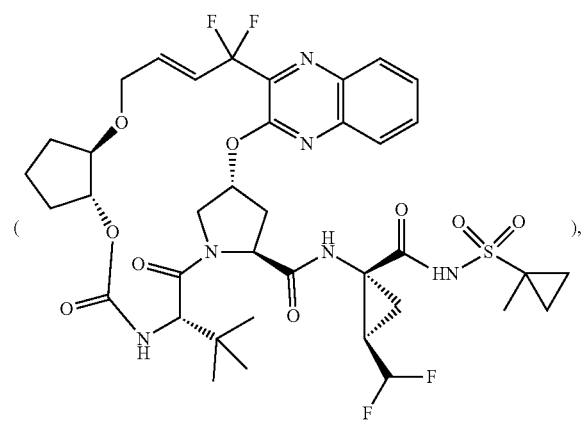

and (2) 120 mg Compound 2

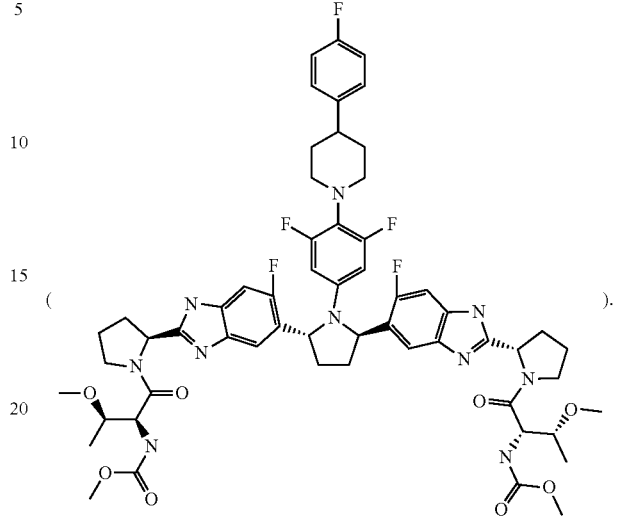

(   ).

4. A method of curing hepatitis C virus (HCV) infection in a treatment experienced patient without cirrhosis infected with HCV genotype 1, 2, 4, 5 or 6, the method comprising:

orally administering a combination of two direct acting antiviral agents (DAAs) once daily for 8 weeks to said patient, wherein said combination of two DAAs comprises:

300 mg Compound

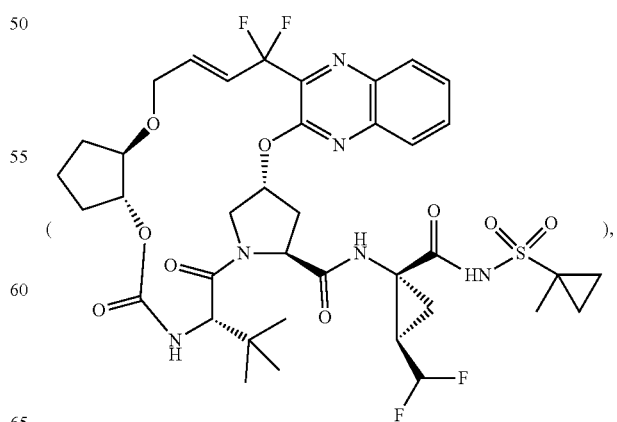

and (2) 120 mg Compound 2

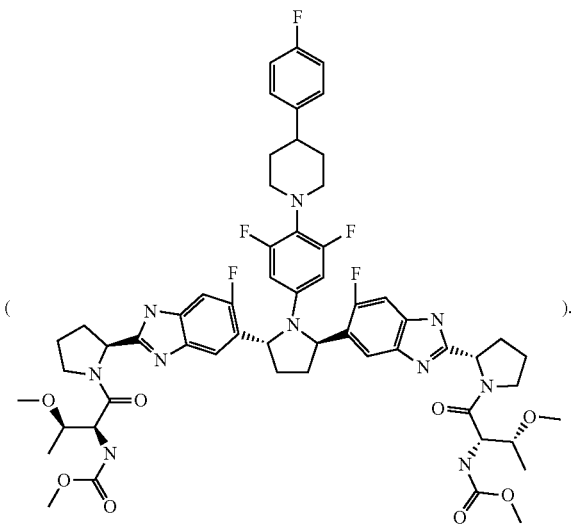

(                                                      ).

5. The method of claim 2, wherein said patient is infected with HCV genotype 1 and is without cirrhosis.

6. The method of claim 5, wherein said patient was previously treated with an NS3 or NS4A inhibitor.

7. The method of claim 2, wherein said patient is infected with HCV genotype 1 and is with compensated cirrhosis.

8. The method of claim 7, wherein said patient was previously treated with an NS3 or NS4A inhibitor.

9. The method of claim 2, wherein said patient is infected with HCV genotype 1, 2, 4, 5 or 6 and is with compensated cirrhosis.

10. The method of claim 9, wherein said patient was previously treated with pegylated interferon/ribavirin.

11. The method of claim 3, wherein said patient is infected with HCV genotype 1 and is without cirrhosis.

12. The method of claim 11, wherein said patient was previously treated with an NS5A inhibitor.

13. The method of claim 3, wherein said patient is infected with HCV genotype 1 and is with compensated cirrhosis.

14. The method of claim 13, wherein said patient was previously treated with an NS5A inhibitor.

15. The method of claim 3, wherein said patient is infected with HCV genotype 3 and is without cirrhosis.

16. The method of claim 15, wherein said patient was previously treated with pegylated interferon/ribavirin 17. The method of claim 3, wherein said patient is infected with HCV genotype 3 and is with compensated cirrhosis.

18. The method of claim 17, wherein said patient was previously treated with pegylated interferon/ribavirin.

19. The method of claim 4, wherein said patient was previously treated with pegylated interferon/ribavirin.

20. The method of claim 1, wherein the patient achieves a sustained virologic response at 24 weeks post-treatment (SVR24).

21. The method of claim 2, wherein the patient achieves a sustained virologic response at 24 weeks post-treatment (SVR24).

22. The method of claim 3, wherein the patient achieves a sustained virologic response at 24 weeks post-treatment (SVR24).

23. The method of claim 4, wherein the patient achieves a sustained virologic response at 24 weeks post-treatment (SVR24).

* * * * *

UNITED STATES PATENT AND TRADEMARK OFFICE
CERTIFICATE OF CORRECTION

PATENT NO. : 11,484,534 B2
APPLICATION NO. : 15/431906
DATED : November 1, 2022
INVENTOR(S) : Walid M. Awni et al.

Page 1 of 1

It is certified that error appears in the above-identified patent and that said Letters Patent is hereby corrected as shown below:

On the Title Page

Item (60), Lines 6-7, delete "Apr. 24, 2014," and insert -- Apr. 02, 2014, --, therefor.

In the Claims

In Column 114, Claim 4, Line 43, delete "300 mg" and insert -- (1) 300 mg --, therefor.

In Column 114, Claim 4, Line 43, delete "Compound" and insert -- Compound 1 --, therefor.

Signed and Sealed this
Twenty-second Day of August, 2023

*Katherine Kelly Vidal*

Katherine Kelly Vidal
*Director of the United States Patent and Trademark Office*